US008586307B2

(12) United States Patent
Skinner

(10) Patent No.: US 8,586,307 B2
(45) Date of Patent: Nov. 19, 2013

(54) METHODS FOR DIAGNOSING EPIGENETIC, TRANSGENERATIONAL EFFECTS OF ENVIRONMENTAL TOXICANTS ON MAMMALIAN GERM-LINES AND TREATING ASSOCIATED DISEASES

(76) Inventor: Michael K. Skinner, Pullman, WA (US)

( * ) Notice: Subject to any disclaimer, the term of this patent is extended or adjusted under 35 U.S.C. 154(b) by 1653 days.

(21) Appl. No.: 11/438,752

(22) Filed: May 22, 2006

(65) Prior Publication Data
US 2006/0286585 A1 Dec. 21, 2006

Related U.S. Application Data

(60) Provisional application No. 60/683,134, filed on May 20, 2005.

(51) Int. Cl.
*C12Q 1/68* (2006.01)
(52) U.S. Cl.
USPC .......................................... 435/6.11; 435/6.1
(58) Field of Classification Search
USPC ................................................ 435/6.1, 6.11
See application file for complete search history.

(56) References Cited

PUBLICATIONS

Nicolopoulou-Stamati et al., 2001, Human Reproduction Update, vol. 7(3), pp. 323-330.*
Rogan et al., 2003, Pediatrics, vol. 112(1), pp. 247-252.*
Cupp et al., 2003, J. of Andrology, vol. 24(5), pp. 736-745.*
Bastepe et al., 2001, Human Molecular Genetics, vol. 10(12), pp. 1231-1241.*
Cheng et al., 2004, Molecular Carcinogenesis, vol. 40, pp. 1-11.*
MacPhee DG, 1998, Mutation Res., vol. 400, pp. 369-379.*
Earl Gray Jr. et al., IDS Feb. 20, 2007.*
Alworth et al.,IDC Feb. 20, 2007.*
Roemer et al., 1997, Current Biology, vol. 7, pp. 277-280.*
Barber et al. (2002, PNAS, vol. 99(10), pp. 6877-6882).*
Dulioust et al. (1989, J. Andrology, vol. 10(4), pp. 296-303).*
Cheng et al. (2004, Molecular Carcinogenesis, vol. 40, pp. 1-11).*
Skinner, 2002, Final Review of Grant, 4 page PDF printout.*
Akingbemi, Benson T. et al., "A Metabolite of Methoxychlor, 2,2-Bis(*p*-Hydroxyphenyl)-1,1,1-Trichloroethane, Reduces Testosterone Biosynthesis in Rat Leydig Cells Through Suppression of Steady-State Messenger Ribonucleic Acid Levels of the Cholesterol Side-Chain Cleavage Enzyme," *Biology of Reproduction*, 2000, 62:571-8 (Exhibit 1).
Akingbemi, Benson T. and Matthew P. Hardy, "Oestrogenic and antiandrogenic chemicals in the environment: effects on male reproductive health," *Ann Med*, 2001, 33:391-403 (Exhibit 2).
Allegrucci, Cinzia et al., "Epigenetics and the germline," *Reproduction*, 2005, 129:137-49 (Exhibit 3).
Alworth, L. C. et al., "Uterine Responsiveness to Estradiol and DNA Methylation are Altered by Fetal Exposure to Diethylstilbestrol and Methoxychlor in CD-1 Mice: Effects of Low Versus High Doses," *Toxicology and Applied Pharmacology*, 2002, 183:10-22 (Exhibit 4).

Anway, Matthew D. et al., "Endocrine Disruptor Vinclozolin Induced Epigenetic Transgenerational Adult-Onset Disease," *Endocrinology*, 2006, 147:5515-23 (Exhibit 5).
Atanassova, N. et al., "Permanent Effects of Neonatal Estrogen Exposure in Rats on Reproductive Hormone Levels, Sertoli Cell Number, and the Efficiency of Spermatogenesis in Adulthood," *Endocrinology*, 1999, 140:5364-73 (Exhibit 6).
Barber, Ruth et al., "Elevated mutation rates in the germ line of first- and second-generation offspring of irradiated male mice," PNAS, 2002, 99:6877-82 (Exhibit 7).
Bartolomei, Marisa S. et al., "Parental imprinting of the mouse H19 gene," *Nature*, 1991, 351:153-5 (Exhibit 8).
Bertram, L. et al., "Paternal age is a risk factor for Alzheimer disease in the absence of a major gene," *Neurogenetics*, 1998, 1:277-80 (Exhibit 9).
Blanchard, Marie-Genevieve and Nathalie Josso, "Source of the Anti-müllerian Hormone Synthesized by the Fetal Testis: Müllerian-inhibiting Activity of Fetal Bovine Sertoli Cells in Tissue Culture," *Pediat. Res.*, 1974, 8:968-71 (Exhibit 10).
Bloch, Eric et al., "Studies on the Inhibition of Fetal Androgen Formation. Inhibition of Testosterone Synthesis in Rat and Rabbit Fetal Testes with Observations on Reproductive Tract Development," *Endocrinology*, 1971, 89:16-31 (Exhibit 11).
Borgeest, C. et al., "Methoxychlor May Cause Ovarian Follicular Atresia and Proliferation of the Ovarian Epithelium in the Mouse," *Toxicological Sciences*, 2002, 68:473-8 (Exhibit 12).
Brandenberger, Alfred W. et al., "Tissue Distribution of Estrogen Receptors Alpha (ER-$\alpha$) and Beta (ER-$\beta$) mRNA in the Midgestational Human Fetus," *Journal of Clinical Endocrinology and Metabolism*, 1997, 82:3509-12 (Exhibit 13).
Brucker-Davis, F. et al., "Update on cryptorchidism: Endocrine, environmental and therapeutic aspects," *Journal of Endocrinological Investigation*, 2003, 26:575-87 (Exhibit 14).
Buehr, Mia et al., "Mesonephric contribution to testis differentiation in the fetal mouse," Development, 1993, 117:273-281 (Exhibit 15).
Bulger, William H. and David Kupfer, "Estrogenic Activity of Pesticides and Other Xenobiotics on the Uterus and Male Reproductive Tract," *Endocrine Toxicology*, John A. Thomas et al., eds., Raven Press: NewYork, 1985, pp. 1-33 (Exhibit 16).
Carlsen, Elisabeth et al., "Evidence for decreasing quality of semen during past 50 years," *BMJ*, 1992, 305:609-13 (Exhibit 17).
Chao, Wei et al., "Fas-associated death-domain protein inhibits TNF-$\alpha$ mediated NF-$\kappa$B activation in cardiomyocytes," *Am J Physiol Heart Circ Physiol*, 2005, 289:H2073-80 (Exhibit 18).
Chapin, R. E. et al., "The Effects of Perinatal/Juvenile Methoxychlor Exposure on Adult Rat Nervous, Immune, and Reproductive System Function," *Fundamental and Applied Toxicology*, 1997, 40:138-57 (Exhibit 19).
Chen, Danhua et al., "Analysis of internal ($n$-1)mer deletion sequences in synthetic oligodeoxyribonucleotides by hybridization to an immobilized probe array," *Nucleic Acids Research*, 1999, 27:389-95 (Exhibit 20).
Cheng, Robert Y-S. et al., "Epigenetic and Gene Expression Changes Related to Transgenerational Carcinogenesis," *Molecular Carcinogenesis*, 2004, 40:1-11 (Exhibit 21).

(Continued)

*Primary Examiner* — Peter Paras, Jr.
*Assistant Examiner* — David A Montanari
(74) *Attorney, Agent, or Firm* — Adriano & Associates

(57) ABSTRACT

The present invention provides methods for detecting epigenetic, multigenerational DNA alterations caused by toxicants such as endocrine disruptor agents in a subject. The practice of the present invention can be used to diagnose and/or treat a subject having the identified DNA alterations by developing therapeutics, to prevent or delay the onset of associated diseases and/or dysfunctions.

6 Claims, 23 Drawing Sheets

(56) References Cited

PUBLICATIONS

Clark, S. J. and M. Frommer, "Bisulphite Genomic Sequencing of Methylated Cytosines," *Laboratory Methods for the Detection of Mutations and Polymorphisms in DNA*, Graham R. Taylor, ed., CRC Press, Inc: Boca Raton, FL, 1997, pp. 151-162 (Exhibit 22).

Clayton-Smith, J. and L. Laan, "Angelman syndrome: a review of the clinical and genetic aspects," *J Med Genet*, 2003, 40:87-95 (Exhibit 23).

Confaloni, Annamaria et al., "Nicastrin gene in familial and sporadic Alzheimer's disease," *Neuroscience Letters*, 2003, 353:61-5 (Exhibit 24).

Cooke, Paul S. and Victor P. Eroschenko, "Inhibitory Effects of Technical Grade Methoxychlor on Development of Neonatal Male Mouse Reproductive Organs," *Biology of Reproduction*, 1990, 42:585-96 (Exhibit 25).

Couse, J. F. et al., "Postnatal Sex Reversal of the Ovaries in Mice Lacking Estrogen Receptors α and β," *Science*, 1999, 286:2328-31 (Exhibit 26).

Cummings, Audrey M., "Methoxychlor as a Model for Environmental Estrogens," *Critical Reviews in Toxicology*, 1997, 27:367-79 (Exhibit 27).

Cupp, Andrea S. and Michael K. Skinner, "Actions of the endocrine disruptor methoxychlor and its estrogenic metabolite on in vitro embryonic rat seminiferous cord formation and perinatal testis growth," *Reproductive Toxicology*, 2001, 15:317-26 (Exhibit 28).

Cupp, Andrea S. et al., "Testis Developmental Phenotypes in Neurotropin Receptor *trkA* and *trkC* Null Mutations: Role in Formation of Seminiferous Cords and Germ Cell Survival," Biology of Reproduction, 2002, 66:1838-45 (Exhibit 29).

Cupp, Andrea S. et al., "Effect of Transient Embryonic In Vivo Exposure to the Endocrine Disruptor Methoxychlor on Embryonic and Postnatal Testis Development," *Journal of Andrology*, 2003, 24:736-45 (Exhibit 30).

Danzo, Benjamin J., "Environmental Xenobiotics May Disrupt Normal Endocrine Function by Interfering with the Binding of Physiological Ligands to Steroid Receptors and Binding Proteins," *Environmental Health Perspectives*, 1997, 105:294-301 (Exhibit 31).

De Strooper, Bart, "Nicastrin: Gatekeeper of the γ-Secretase Complex," *Cell*, 2005, 122:318-20 (Exhibit 32).

Deak, Kristen L. et al., "SNPs in the neural cell adhesion molecule 1 gene (*NCAM1*) may be associated with human neural tube defects," *Hum Genet*, 2005, 117:133-42 (Exhibit 33).

Dehal, Shangara S. and David Kupfer, "Metabolism of the Proesterogenic Pesticide Methoxychlor by Hepatic P450 Monooxygenases in Rats and Humans," *Drug Metabolism and Disposition*, 1994, 22:937-46 (Exhibit 34).

DeRosa, Christopher et al., "Environmental Exposures that Affect the Endocrine System: Public Health Implications," *Journal of Toxicology and Environmental Health*, 1998, 1:3-26 (Exhibit 35).

Desai, K. V. and P. Kondaiah, "Androgen ablation results in differential regulation of transforming growth factor-β isoforms in rat male accessory sex organs and epididymis," *Journal of Molecular Endocrinology*, 2000, 24:253-60 (Exhibit 36).

Dong, Huan et al., "Mutagenic Potential of Benzo[*a*]pyrene-Derived DNA Adducts Positioned in Codon 273 of the Human P53 Gene," *Biochemistry*, 2004, 43:15922-8 (Exhibit 37).

Dorrington, J. H. et al., "Control of Testicular Estrogen Synthesis," Biology of Reproduction, 1978, 18:55-64 (Exhibit 38).

Dubourg, Christèle et al., "Molecular Screening of SHH, ZIC2, S/X3, and TGIF Genes in Patients with Features of Holoprosencephaly Spectrum: Mutation Review and Genotype-Phenotype Correlations," *Human Mutation*, 2004, 24:43-51 (Exhibit 39).

Dubrova, Yuri E., "Radiation-induced transgenerational instability," *Oncogene*, 2003, 22:7087-93 (Exhibit 40).

Durcova-Hills, Gabriela et al., "Pluripotential stem cells derived from migrating primordial germ cells," *Differentiation*, 2001, 68:220-6 (Exhibit 41).

Ebling, Francis J. P. et al., "Estrogenic Induction of Spermatogenesis in the Hypogonadal Mouse," *Endocrinology*, 2000, 141:2861-9 (Exhibit 42).

Eddy, E. M. et al., "Targeted Disruption of the Estrogen Receptor Gene in Male Mice Causes Alteration of Spermatogenesis and Infertility," *Endocrinology*, 1996, 137:4796-805 (Exhibit 43).

Eilers, Helge et al., "Isolation of an mRNA binding protein homologue that is expressed in nociceptors," *European Journal of Neuroscience*, 2004, 20:2283-93 (Exhibit 44).

Eroschenko, Victor P. et al., "Neonatal Exposures to Technical Methoxychlor Alters Ovaries in Adult Mice," *Reproductive Toxicology*, 1995, 9:379-87 (Exhibit 45).

Eroschenko, Victor P. et al., "Estradiol or Methoxychlor Stimulates Estrogen Receptor (ER) Expression in Uteri," *Reproductive Toxicology*, 1996, 10:265-71 (Exhibit 46).

Facemire, Charles F. et al., "Reproductive Impairment in the Florida Panther: Nature or Nuture?," *Environmental Health Perspective Supplements*, 1995, 103:79-86 (Exhibit 47).

Fawcett, Don W., "Ultrastructure and function of the Sertoli cell," *Handbook of Physiology*, Roy O. Greep et al., eds., American Physiological Society, D.C., 1975, pp. 21-55 (Exhibit 48).

Fernebro, Josefin et al., "Gene expression profiles relate to SS18/SSX fusion type in synovial sarcoma," *Int. J. Cancer*, 2006, 118:1165-72 (Exhibit 49).

Fiorentino, F. et al., "Gene Symbol: WAS. Disease: Wiskott-Aldrich syndrome," *Hum Genet*, 2005, 116:539 (Exhibit 50).

Fisher, Jane S., "Environmental anti-androgens and male reproductive health: focus on phthalates and testicular dysgenesis syndrome," *Reproduction*, 2004, 127:305-15 (Exhibit 51).

Foran, Christy M. et al., "Transgenerational and Developmental Exposure of Japanese Medaka (*Oryzias latipes*) to Ethinylestradiol Results in Endocrine and Reproductive Differences in the Response to Ethinylestradiol as Adults," *Toxicological Sciences*, 2002, 68:389-402 (Exhibit 52).

Fraga, Mario F. et al., "Epigenetic differences arise during the lifetime of monozygotic twins," *PNAS*, 2005, 102:10604-9 (Exhibit 53).

Fridmacher, Valérie et al., "Switch in the expression of the K19/K18 keratin genes as a very early evidence of testicular differentiation in the rat," *Mechanisms of Development*, 1995, 52:199-207 (Exhibit 54).

Fröjdman, Kim et al., "Intermediate filaments and epithelial differentiation of male rat embryonic gonad," *Differentiation*, 1992, 50:113-23 (Exhibit 55).

Frommer, Marianne et al., "A genomic sequencing protocol that yields a positive display of 5-methlycytosine residues in individual DNA strands," *PNAS*, 1992, 89:1827-31 (Exhibit 56).

Fujii, Tomoko, "Transgenerational effects of maternal exposure to chemicals on the functional development of the brain in the offspring," *Cancer Causes and Control*, 1997, 8:524-8 (Exhibit 57).

Gaido, Kevin W. et al., "Differential Interaction of the Methoxychlor Metabolite 2,2-Bis-(*p*-Hydroxyphenyl)-1,1,1-Trichloroethane with Estrogen Receptors α and β," *Endocrinology*, 1999, 140:5746-53 (Exhibit 58).

Gaido, Kevin W. et al., "Interaction of Methoxychlor and Related Compounds with Estrogen Receptor α and β, and Androgen Receptor: Structure-Activity Studies," *Molecular Pharmacology*, 2000, 58:852-8 (Exhibit 59).

Gluckman, Peter D. and Mark A. Hanson, "Developmental Origins of Disease Paradigm: A Mechanistic and Evolutionary Perspective," *Pediatric Research*, 2004, 56:311-7 (Exhibit 60).

Golub, Mari S. et al., "Effects of Exogenous Estrogenic Agents on Pubertal Growth and Reproductive System Maturation in Female Rhesus Monkeys," *Toxicological Sciences*, 2003, 74:103-13 (Exhibit 61).

Gong, Gordon et al., "Genetic dissection of myocilin glaucoma," *Human Molecular Genetics*, 2004, 13:R91-102 (Exhibit 62).

Gonzalgo, Mark L. et al., "Identification and Characterization of Differentially Methylated Regions of Genomic DNA by Methylation-sensitive Arbitrarily Primed PCR," *Cancer Research*, 1997, 57:594-9 (Exhibit 63).

Goyal, Hari O. et al., "Immunolocalization of Androgen Receptor and Estrogen Receptor in the Developing Testis and Excurrent Ducts of Goats," *The Anatomical Record*, 1997, 249:54-62 (Exhibit 64).

Gray, L. Earl Jr. et al., "Environmental antiandrogens: low doses of the fungicide vinclozolin alter sexual differentiation of the male rat," *Toxicology and Industrial Health*, 1999, 15:48-64 (Exhibit 65).

(56) References Cited

OTHER PUBLICATIONS

Gray, L. Earl Jr. et al., "Administration of potentially antiandrogenic pesticides (procymidone, linuron, iprodione, chlozolinate, p,p'-DDE, and ketoconazole) and toxid substances (dibutyl- and diethylhexyl phthalate, PCB 169, and ethane dimethane sulphonate) during sexual differentiation produces diverse profiles of reproductive malformations in the male rat," *Toxicology and Industrial Health*, 1999, 15:94-118 (Exhibit 66).

Greene, R. R., "Embryology of Sexual Structure and Hermaphroditism," *Journal of Clinical Endocrinology*, 1944, 4:335-48 (Exhibit 67).

Griswold, Michael D., "Protein Secretions of Sertoli Cells," *International Review of Cytology*, 1988, 110:133-56 (Exhibit 68).

Gupta, Chhanda et al., "The Role of EGF in Testosterone-Induced Reproductive Tract Differentiation," *Developmental Biology*, 1991, 146:106-16 (Exhibit 69).

Gupta, Chhanda, "The Role of Epidermal Growth Factor Receptor (EGFR) in Male Reproductive Tract Differentiation: Stimulation of EGFR Expression and Inhibition of Wolffian Duct Differentiation with Anti-EGFR Antibody," *Endocrinology*, 1996, 137:905-10 (Exhibit 70).

Gupta, Chhanda et al., "Activation of androgen receptor in epidermal growth factor modulation of fetal mouse sexual differentiation," *Molecular and Cellular Endocrinology*, 1996, 123:89-95 (Exhibit 71).

Hajkova, Petra et al., "Epigenetic reprogramming in mouse primordial germ cells," *Mechanisms of Development*, 2002, 117:15-23 (Exhibit 72).

Håkansson, Joakim et al., "Neural Cell Adhesion Molecule-Deficient β-Cell Tumorigenesis Results in Diminished Extracellular Matrix Molecule Expression and Tumour Cell-Matrix Adhesion," *TumorBiology*, 2005, 26:103-12 (Exhibit 73).

Heindel, Jerrold J., "The Fetal Basis of Adult Disease: Role of Environmental Exposures—Introduction," *Birth Defects Research, Part A: Clinical and Molecular Teratology*, 2005, 73:131-2 (Exhibit 74).

Hellwig, J. et al., "Pre- and Postnatal Oral Toxicity of Vinclozolin in Wistar and Long-Evans Rats," *Regulatory Toxicology and Pharmacology*, 2000, 32:42-50 (Exhibit 75).

Hof, D. et al., "Apoptotic modifications affect the autoreactivity of the U1 snRNP autoantigen," *Autoimmunity Reviews*, 2005, 4:380-8 (Exhibit 76).

Hoffman, Robert W. et al., "U1 RNA Induces Innate Immunity Signaling," *Arthritis & Rheumatism*, 2004, 50:2891-6 (Exhibit 77).

Hotchkiss, A. K. et al., "Androgens and Environmental Antiandrogens Affect Reproductive Development and Play Behavior in the Sprague-Dawley Rat," *Environmental Health Perspectives*, 2002, 110:435-9 (Exhibit 78).

Hoyes, Katharine P. et al., "Transgenerational Effects of Preconception Paternal Contamination with 55Fe," *Radiation Research*, 2001, 156:488-94 (Exhibit 79).

Jiang, Yong-hui et al., "Epigenetics and Human Disease," *Annu. Rev. Genomics Hum. Genet.*, 2004, 5:479-510 (Exhibit 80).

Jost, A. et al., "Early Stages of Testicular Differentiation in the Rat," *Human Genetics*, 1981, 58:59-63 (Exhibit 81).

Kanemura, Yonehiro et al., "First case of L1CAM gene mutation identified in MASA syndrome in Asia," *Congenital Anomalies*, 2005, 45:67-9 (Exhibit 82).

Kang, Ik Joon et al., "Effects of Bisphenol A on the Reproduction of Japanese Medaka (*Oryzias latipes*)," *Environmental Toxicology and Chemistry*, 2002, 21:2394-400 (Exhibit 83).

Kapoor, Inder P. et al., "Comparative Metabolism of Methoxychlor, Methiochlor, and DDT in Mouse, Insects, and in a Model Ecosystem," *Journal of Agricultural and Food Chemistry*, 1970, 18:1145-52 (Exhibit 84).

Kawamura, Shuji et al., "A Family of Hypokalemic Periodic Paralysis with CACNA1S Gene Mutation Showing Incomplete Penetrance in Women," *Internal Medicine*, 2004, 43:218-22 (Exhibit 85).

Kelce, William R. et al., "Environment Hormone Disruptors: Evidence that Vinclozolin Developmental Toxicity is Mediated by Antiandrogenic Metabolites," *Toxicology and Applied Pharmacology*, 1994, 126:276-85 (Exhibit 86).

Kelce, William R. et al., "Persistent DDT metabolite p,p'-DDE is a potent androgen receptor antagonist," *Nature*, 1995, 375:581-5 (Exhibit 87).

Kelce, William R. et al., "Vinclozolin and p,p'-DDE Alter Androgen-Dependent Gene Expression: In Vivo Confirmation of an Androgen Receptor-Mediated Mechanism," *Toxicology and Applied Pharmacology*, 1997, 142:192-200 (Exhibit 88).

Kelce, W. R. et al., "Antiandrogens as environmental endocrine disruptors," *Reproduction, Fertility and Development*, 1998, 10:105-11 (Exhibit 89).

Kierszenbaum, Abraham L., "Mammalian Spermatogenesis in Vivo and in Vitro: A Partnership of Spermatogenic and Somatic Cell Lineages," *Endocrine Reviews*, 1994, 15:116-34 (Exhibit 90).

Kimberly, W. Taylor and Michael S. Wolfe, "Identity and Function of γ-Secretase," *Journal of Neuroscience Research*, 2003, 74:353-60 (Exhibit 91).

Kupfer, David et al., "Metabolism of Methoxychlor by Hepatic P-450 Monooxygenases in Rat and Human. 1. Characterization of a Novel Catechol Metabolite," *Chemical Research in Toxicology*, 1990, 3:8-16 (Exhibit 92).

Kvist, Ulrik and Lars Björndahl, "Sperm Motility," *Manual on Basic Semen Analysis*, Rev. ed. ESHRE monographs, Germany: ESHRE and Oxford University Press, 2002, pp. 14-17 (Exhibit 93).

Lacroix, Martial et al., "Secretion of Plasminogen Activator by Sertoli Cell Enriched Cultures," *Molecular and Cellular Endocrinology*, 1977, 9:227-36 (Exhibit 94).

Laflamme, Cynthia et al., "The Homeotic Protein Six3 is a Coactivator of the Nuclear Receptor NOR-1 and a Corepressor of the Fusion Protein EWS/NOR-1 in Human Extraskeletal Myxoid Chondrosarcomas," *Cancer Research*, 2003, 63:449-54 (Exhibit 95).

Lamoureux, Carolejean H. and Vernon J. Feil, "Gas Chromatographic and Mass Spectrometric Characterization of Impurities in Technical Methoxychlor," *Journal of the Association of Official Analytical Chemists*, 1980, 63:1007-37 (Exhibit 96).

Lane, Natasha et al., "Resistance of IAPs to Methylation Reprogramming May Provide a Mechanism for Epigenetic Inheritance in the Mouse," *Genesis*, 2003, 35:88-93 (Exhibit 97).

Langley-Evans, Simon C., "Developmental programming of health and disease," *Proceedings of the Nutrition Society*, 2006, 65:97-105 (Exhibit 98).

Latchoumycandane, C. and P. P. Mathur, "Effect of methoxychlor on the antioxidant system in mitochondrial and microsome-rich fractions of rat testis," *Toxicology*, 2002, 176:67-75 (Exhibit 99).

Lazaro, Leila et al., "Phenotypic and Molecular Variability of the Holoprosencephalic Spectrum," *American Journal of Medical Genetics*, 2004, 129A:21-4 (Exhibit 100).

Lee, Jiyoung et al., "Erasing genomic imprinting memory in mouse clone embryos produced from day 11.5 primordial germ cells," *Development*, 2002, 129:1807-17 (Exhibit 101).

Lee, Ki-Ho et al., "Estrogen Receptor α has a Functional Role in the Mouse Rete Testis and Efferent Ductules," *Biology of Reproduction*, 2000, 63:1873-80 (Exhibit 102).

Levine, Elena et al., "Role of Neurotropins in Rat Embryonic Testis Morphogenesis (Cord Formation)," *Biology of Reproduction*, 2000, 62:132-42 (Exhibit 103).

Levine, Elena et al., "Role of Transforming Growth Factor-α and the Epidermal Growth Factor Receptor in Embryonic Rat Testis Development," *Biology of Reproduction*, 2000, 62:477-90 (Exhibit 104).

Li, En, "Chromatin Modification and Epigenetic Reprogramming in Mammalian Development," *Nature Reviews Genetics*, 2002, 3:662-73 (Exhibit 105).

Li, Hua et al., "Regulation of Rat Testis Gonocyte Proliferation by Platelet-Derived Growth Factor and Estradiol: Identification of Signaling Mechanisms Involved," *Endocrinology*, 1997, 138:1289-98 (Exhibit 106).

Li, Jing-Yu et al., "Timing of establishment of paternal methylation imprints in the mouse," *Genomics*, 2004, 84:952-60 (Exhibit 107).

Li, Long-Cheng and Rajvir Dahiya, "MethPrimer: designing primers for methylation PCRs," *Bioinformatics*, 2002, 18:1427-31 (Exhibit 108).

(56) References Cited

OTHER PUBLICATIONS

Li, Tong et al., "Nicastrin is Required for Assembly of Presenilin/γ-Secretase Complexes to Mediate Notch Signaling and for Processing and Trafficking of β-Amyloid Precursor Protein in Mammals," *Journal of Neuroscience*, 2003, 23:3272-7 (Exhibit 109).

Liang, Gangning et al., "DNA Methylation Differences Associated with Tumor Tissues Identified by Genome Scanning Analysis," *Genomics*, 1998, 53:260-8 (Exhibit 110).

Liu, Shujun et al., "Interplay of RUNX1/MTG8 and DNA Methyltransferase 1 in Acute Myeloid Leukemia," *Cancer Res*, 2005, 65:1277-84 (Exhibit 111).

Lu, Zhong-Ju et al., "Arrhythmia in Isolated Prenatal Hearts after Ablation of the $Ca_v 2.3$. ($\alpha 1E$) Subunit of Voltage-gated $Ca^2+$ Channels," *Cellular Physiology and Biochemistry*, 2004, 14:11-22 (Exhibit 112).

Lucifero, Diana et al., "Potential significance of genomic imprinting defects for reproduction and assisted reproductive technology," *Human Reproduction Update*, 2004, 10:3-18 (Exhibit 113).

Luedi, Philippe P. et al., "Genome-wide prediction of imprinted murine genes," *Genome Research*, 2005, 15:875-84 (Exhibit 114).

Magre, Solange and Alfred Jost, "The Initial Phases of Testicular Organogenesis in the Rat. An Electron Microscopy Study," *Archives D'Anatomie Microscopique et de Morphologie Experimentale*, 1980, 69:297-317 (Exhibit 115).

Magre, Solange and Alfred Jost, "Sertoli Cells and Testicular Differentiation in the Rat Fetus," *Journal of Electron Microscopy Technique*, 1991, 19:172-88 (Exhibit 116).

Majdic, G. et al., "Immunolocalisation of androgen receptor to interstitial cells in fetal rat testes and to mesenchymal and epithelial cells of associated ducts," *Journal of Endocrinology*, 1995, 147:285-293 (Exhibit 117).

Martin, Richard M. et al., "Parents' Growth in Childhood and the Birth Weight of Their Offspring," *Epidemiology*, 2004, 15:308-16 (Exhibit 118).

Masutomi, Naoya et al., "Impact of dietary exposure to methoxychlor, genistein, or diisononyl phthalate during the perinatal period on the development of the rat endocrine/reproductive systems in later life," *Toxicology*, 2003, 192:149-70 (Exhibit 119).

Matthews, Jason et al., "Differential estrogen receptor binding of estrogenic substances: a species comparison," *Journal of Steroid Biochemistry & Molecular Biology*, 2000, 74:223-34 (Exhibit 120).

McKinnell, C. et al., "Suppression of Androgen Action and the Induction of Gross Abnormalities of the Reproductive Tract in Male Rats Treated Neonatally with Diethylstilbestrol," *Journal of Andrology*, 2001, 22:323-38 (Exhibit 121).

McLaren, Anne, "Development of the Mammalian Gonad: The Fate of the Supporting Cell Lineage," *BioEssays*, 1991, 13:151-6 (Exhibit 122).

McLean, Derek J. et al., "Oligonucleotide Microarray Analysis of Gene Expression in Follicle-Stimulating Hormone-Treated Rat Sertoli Cells," *Molecular Endocrinology*, 2002, 16:2780-92 (Exhibit 123).

Mohr, U. et al., "Possible carcinogenic effects of X-rays in a transgenerational study with CBA mice," *Carcinogenesis*, 1999, 20:325-32 (Exhibit 124).

Monk, Marilyn and Ashreena Salpekar, "Expression of imprinted genes in human preimplantation development," *Molecular and Cellular Endocrinology*, 2001, 183:S35-40 (Exhibit 125).

Monosson, Emily et al., "Peripubertal exposure to the antiandrogenic fungicide, vinclozolin, delays puberty, inhibits the development of androgen-dependent tissues, and alters androgen receptor function in the male rat," *Toxicology and Industrial Health*, 1999, 15:65-79 (Exhibit 126).

Moorman, W. J. et al., "Male adolescent exposure to endocrine-disrupting pesticides: vinclozolin exposure in peripubertal rabbits," *Andrologia*, 2000, 32:285-93 (Exhibit 127).

Morgan, Hugh D. et al., "Epigenetic reprogramming in mammals," *Human Molecular Genetics*, 2005, 14:R47-58 (Exhibit 128).

Morison, Ian M. et al., "A census of mammalian imprinting," *Trends in Genetics*, 2005, 21:457-65 (Exhibit 129).

Nambu, Akihito and Yoshiaki Kumamoto, "Studies of Spermatogenic Damages Induced by Anti-Cancer Agent and Anti-Androgenic Agents in Rat Testes," *The Japanese Journal of Urology*, 1995, 86:1221-30 (Exhibit 130).

Nanni, Luisa et al., "Holoprosencephaly: Molecular Study of a California Population," *American Journal of Medical Genetics*, 2000, 90:315-9 (Exhibit 131).

Nekrep, Nada et al., "Analysis of Ankyrin Repeats Reveals How a Single Point Mutation in RFXANK Results in Bare Lymphocyte Syndrome," *Molecular and Cellular Biology*, 2001, 21:5566-76 (Exhibit 132).

Nicolopoulou-Stamati, P. and M. A. Pitsos, "The impact of endocrine disrupters on the female reproductive system," *Human Reproduction Update*, 2001, 7:323-30 (Exhibit 133).

Nielsen, M. et al., "Ontogeny of oestrogen receptor in gonads and sex ducts of fetal and newborn mice," *Journal of Reproduction and Fertility*, 2000, 118:195-204 (Exhibit 134).

Nomura, T. et al., "Transgenerational transmission of radiation- and chemically induced tumors and congenital anomalies in mice: studies of their possible relationship to induced chromosomal and molecular changes," *Cytogenetic and Genome Research*, 2004, 104:252-60 (Exhibit 135).

Olek, Alexander et al., "A modified and improved method for bisulphate based cytosine methylation analysis," *Nucleic Acids Research*, 1996, 24:5064-6 (Exhibit 136).

Orth, Joanne M. et al., "Environmental Stress Alters the Developmental Pattern of $^5$-3β-Hydroxysteroid Dehydrogenase Activity in Leydig Cells of Fetal Rats: A Quantitative Cytochemical Study," *Biology of Reproduction*, 1983, 28:625-31 (Exhibit 137).

Palanza, P. et al., "Prenatal exposure to endocrine disrupting chemicals: effects on behavioral development," *Neuroscience and Biobehavioral Reviews*, 1999, 23:1011-27 (Exhibit 138).

Parks, Louise G. et al., "The Plasticizer Diethylhexyl Phthalate Induces Malformations by Decreasing Fetal Testosterone Synthesis during Sexual Differentiation in the Male Rat," *Toxicological Sciences*, 2000, 58:339-49 (Exhibit 139).

Pembrey, Marcus E. et al., "Sex-specific, male-line transgenerational responses in humans," *European Journal of Human Genetics*, 2006, 14:159-66 (Exhibit 140).

Pereverzev, Alexey et al., "Disturbances in Glucose-Tolerance, Insulin-Release, and Stress-Induced Hyperglycemia upon Disruption of the $Ca_v 2.3$ ($\alpha 1E$) Subunit of Voltage-Gated $Ca^2+$ Channels," *Molecular Endocrinology*, 2002, 16:884-95 (Exhibit 141).

Pettersson, Katarina and Jan-Åke Gustafsson, "Role of Estrogen Receptor Beta in Estrogen Action," *Annu. Rev. Physiol.*, 2001, 63:165-92 (Exhibit 142).

Pfeifer, Karl, "Mechanisms of Genomic Imprinting," *Am. J. Hum. Genet.*, 2000, 67:777-87 (Exhibit 143).

Plappert, Claudia F. et al., "Neural cell adhesion molecule-null mice are not deficient in prepulse inhibition of the startle response," *NeuroReport*, 2005, 16:1009-12 (Exhibit 144).

Pothuluri, Jairaj V. et al., "Biotransformation of Vinclozolin by the Fungus *Cunninghamella elegans*," *Journal of Agricultural and Food Chemistry*, 2000, 48:6138-48 (Exhibit 145).

Prins, Gail S. and Lynn Birch, "The Developmental Pattern of Androgen Receptor Expression in Rat Prostate Lobes is Altered After Neonatal Exposure to Estrogen," *Endocrinology*, 1995, 136:1303-1314 (Exhibit 146).

Rakyan, Vardhman K. et al., "Transgenerational inheritance of epigenetic states at the murine $Axin^{Fu}$ allele occurs after maternal and paternal transmission," *PNAS*, 2003, 100:2538-43 (Exhibit 147).

Rakyan, Vardhman and Emma Whitelaw, "Transgenerational epigenetic inheritance," *Curr Biol*, 2003, 13:R6 (Exhibit 148).

Robinson, Ranga and Irving B. Fritz, "Metabolism of Glucose by Sertoli Cells in Culture," *Biology of Reproduction*, 1981, 24:1032-41 (Exhibit 149).

Roemer, Irmgard et al., "Epigenetic inheritance in the mouse," *Current Biology*, 1997, 7:277-80 (Exhibit 150).

Russell, Lonnie D. et al., "Three-dimensional Reconstruction of a Rat Stage V Sertoli Cell: III. A Study of Specific Cellular Relationships," *The American Journal of Anatomy*, 1983, 167:181-92 (Exhibit 151).

(56) References Cited

OTHER PUBLICATIONS

Sakata, Yu et al., "Ca$_v$2.3 ($\alpha_{1E}$) Ca$^2$ + channel participates in the control of sperm function," *FEBS Letters*, 2002, 516:229-33 (Exhibit 152).

Sarfarazi, Mansoor and Tayebeh Rezaie, "Optineurin in primary open angle glaucoma," *Ophthalmology Clinics of North America*, 2003, 16:529-41 (Exhibit 153).

Sato, Shun et al., "Erasure of Methylation Imprinting of *Igf2r* During Mouse Primordial Germ-Cell Development," *Molecular Reproduction and Development*, 2003, 65:41-50 (Exhibit 154).

Saunders, P. T. K. et al., "Expression of oestrogen receptor beta (ERβ) in multiple rat tissues visualized by immunohistochemistry," *Journal of Endocrinology*, 1997, 154:R13-6 (Exhibit 155).

Scarano, Maria Irene et al., "DNA Methylation 40 Years Later: Its Role in Human Health and Disease," *Journal of Cellular Physiology*, 2005, 204:21-35 (Exhibit 156).

Schumacher, Axel et al., "Microarray-based DNA methylation profiling: technology and applications," *Nucleic Acids Research*, 2006, 34:528-42 (Exhibit 157).

Schwaiger, J. et al., "How estrogenic is nonylphenol? A transgenerational study using rainbow trout (*Oncorhynchus mykiss*) as a test organism," *Aquatic Toxicology*, 2002, 59:177-89 (Exhibit 158).

Sertoli, Enrico, "On the existence of special branched cells in the seminiferous tubule of the human testes," *Il Morgangni*, 1865, 7:31-9 (Exhibit 159).

Setchell, B. P. and G. M. H. Waites, "The blood-testis barrier," *Handbook of Physiology*, Roy O. Greep et al., eds., American Physiological Society, D.C., 1975, pp. 143-172 (Exhibit 160).

Sharpe, Richard M. et al., "Gestational and Lactational Exposure of Rats to Xenoestrogens Results in Reduced Testicular Size and Sperm Production," *Environmental Health Perspectives*, 1995, 103:1136-43 (Exhibit 161).

Shima, James E. et al., "The Murine Testicular Transcriptome: Characterizing Gene Expression in the Testis During the Progression of Spermatogenesis," *Biology of Reproduction*, 2004, 71:319-30 (Exhibit 162).

Shimada, Atsuko and Akihiro Shima, "Transgenerational genomic instability as revealed by a somatic mutation assay using the medaka fish," *Mutation Research*, 2004, 552:119-24 (Exhibit 163).

Shono, T. et al., "The Effect of a Prenatal Androgen Disruptor, Vinclozolin, on Gubernacular Migration and Testicular Descent in Rats," *Journal of Pediatric Surgery*, 2004, 39:213-6 (Exhibit 164).

Shu, Tianzhi et al., "Abnormal Development of Forebrain Midline Glia and Commissural Projections in *Nfia* Knock-Out Mice," *Journal of Neuroscience*, 2003, 23:203-12 (Exhibit 165).

Silversides, David W. et al., "Effects of short-term exposure to hydroxyflutamide in utero on the development of the reproductive tract in male mice," *Can. J. Physio. Pharmacol.*, 1995, 73:1582-8 (Exhibit 166).

Skinner, Michael K. and Michael D. Griswold, "Sertoli Cells Synthesize and Secrete Transferrin-like Protein," *Journal of Biological Chemistry*, 1980, 255:9523-5 (Exhibit 167).

Skinner, Michael K. and Michael D. Griswold, "Sertoli Cells Synthesize and Secrete a Ceruloplasmin-Like Protein," *Biology of Reproduction*, 1983, 28:1225-9 (Exhibit 168).

Skinner, Michael K. et al., "Purification and characterization of testicular transferrin secreted by rat Sertoli cells," *Biochem J*, 1984, 218:313-20 (Exhibit 169).

Skinner, Michael K., "Cell-Cell Interactions in the Testis," *Endocrine Reviews*, 1991, 12:45-77 (Exhibit 170).

Smith, Eric P. et al., "Estrogen Resistance Caused by a Mutation in the Estrogen-Receptor Gene in a Man," *The New England Journal of Medicine*, 1994, 331:1056-61 (Exhibit 171).

Stoker, Tammy E. et al., "Perinatal exposure to estrogenic compounds and the subsequent effects on the prostate of the adult rat: evaluation of inflammation in the ventral and lateral lobes," *Reproductive Toxicology*, 1999, 13:463-472 (Exhibit 172).

Suzuki, Masatoshi et al., "Effects of Methoxychlor Exposure during Perinatal Period on Reproductive Function after Maturation in Rats," *Journal of Reproduction and Development*, 2004, 50:455-61 (Exhibit 173).

Swartz, William J. and Michele Corkern, "Effects of Methoxychlor Treatment of Pregnant Mice on Female Offspring of the Treated and Subsequent Pregnancies," *Reproductive Toxicology*, 1992, 6:431-7 (Exhibit 174).

Swartz, William J. and Victor P. Eroschenko, "Neonatal Exposure to Technical Methoxychlor Alters Pregnancy Outcome in Female Mice," *Reproductive Toxicology*, 1998, 12:565-73 (Exhibit 175).

Takeuchi, Toru et al., "Positive Relationship between Androgen and the Endocrine Disruptor, Bisphenol A, in Normal Women and Women with Ovarian Dysfunction," *Endocrine Journal*, 2004, 51:165-9 (Exhibit 176).

Takeuchi, Yukiko et al., "Thymic atrophy induced by methoxychlor in rat pups," *Toxicology Letters*, 2002, 135:199-207 (Exhibit 177).

Taylor, G. T. et al., "Copulation induces an acute increase in epididymal sperm numbers in rats," *Journal of Reproduction & Fertility*, 1985, 73:323-7 (Exhibit 178).

Tena-Sempere, M. et al., "Neonatal exposure to estrogen differentially alters estrogen receptor α and β mRNA expression in rat testis during postnatal development," *Journal of Endocrinology*, 2000, 165:345-57 (Exhibit 179).

Tena-Sempere, Manuel et al., "Neonatal Imprinting and Regulation of Estrogen Receptor Alpha and Beta mRNA Expression by Estrogen in the Pituitary and Hypothalamus of the Male Rat," *Neuroendocrinology*, 2001, 73:12-25 (Exhibit 180).

Todaro, Laura et al., "Neural cell adhesion molecule in human serum. Increased levels in dementia of the Alzheimer type," *Neurobiology of Disease*, 2004, 15:387-93 (Exhibit 181).

Tokumura, Akira, "Metabolic Pathways and Physiological and Pathological Significances of Lysolipid Phosphate Mediators," *Journal of Cellular Biochemistry*, 2004, 92:869-81 (Exhibit 182).

Tsui, Martin T. K. and Wen-Xiong Wang, "Maternal Transfer Efficiency and Transgenerational Toxicity of Methylmercury in *Daphnia Magna*," *Environmental Toxicology and Chemistry*, 2004, 23:1504-11 (Exhibit 183).

Tung, Pierre S. et al., "Fibronectin Synthesis is a Marker for Peritubular Cell Contaminants in Sertoli Cell-Enriched Cultures," *Biology of Reproduction*, 1984, 30:199-211 (Exhibit 184).

Turner, Katie J. et al., "Effects of in Utero Exposure to the Organophosphate Insecticide Fenitrothion on Androgen-Dependent Reproductive Development in the Crl:CD(SD)BR Rat," *Toxicological Sciences*, 2002, 68:174-83 (Exhibit 185).

Uzumcu, Mehmet et al., "Effect of the anti-androgenic endocrine disruptor vinclozolin on embryonic testis cord formation and postnatal testis development and function," *Reproductive Toxicology*, 2004, 18:765-74 (Exhibit 186).

Valkova, Nelly et al., "Nek8 Mutation Causes Overexpression of Galectin-1, Sorcin, and Vimentin and Accumulation of the Major Urinary Protein in Renal Cysts of *jck* Mice," *Molecular & Cellular Proteomics*, 2005, 4:1009-18 (Exhibit 187).

Vissing, John et al., "Effect of Fuels on Exercise Capacity in Muscle Phosphoglycerate Mutase Deficiency," *Arch Neurol.*, 2005, 62:1440-3 (Exhibit 188).

Waites, G. M. H. and R. T. Gladwell, "Physiological Significance of Fluid Secretion in the Testis and Blood-Testis Barrier," *Physiological Reviews*, 1982, 62:624-71 (Exhibit 189).

Wang, Jiandong et al., "Downregulation of EphA7 by hypermethylation in colorectal cancer," *Oncogene*, 2005, 24:5637-47 (Exhibit 190).

Weksberg, Rosanna et al., "Beckwith-Wiedemann Syndrome," *American Journal of Medical Genetics Part C (Semis. Med. Genet.)*, 2005, 137:12-23 (Exhibit 191).

West, Paul R. et al., "High Performance Liquid Chromatographic Analysis of Impurities and Degradation Products of Methoxychlor," *Journal of the Association of Official Analytical Chemists*, 1982, 65:1457-70 (Exhibit 192).

Wilson, Carol M. and Michael J. McPhaul, "A and B forms of the androgen receptor are expressed in a variety of human tissues," *Molecular and Cellular Endocrinology*, 1996, 120:51-7 (Exhibit 193).

(56) References Cited

OTHER PUBLICATIONS

Wolf, Cynthia J. et al., "Characterization of the Period of Sensitivity of Fetal Male Sexual Development to Vinclozolin," *Toxicological Sciences*, 2000, 55:152-61 (Exhibit 194).

Wolf, Cynthia J. et al., "Interactive Effects of Vinclozolin and Testosterone Propionate on Pregnancy and Sexual Differentiation of the Male and Female SD Rat," *Toxicological Sciences*, 2004, 78:135-43 (Exhibit 195).

Wu, Yun-Ping et al., "Apoptosis accompanied by up-regulation of TNF-death pathway genes in the brain of Niemann-Pick type C disease," *Molecular Genetics and Metabolism*, 2005, 84:9-17 (Exhibit 196).

Yamazaki, Yukiko et al., "Reprogramming of primordial germ cells begins before migration into the genital ridge, making these cells inadequate donors for reproductive cloning," *PNAS*, 2003, 100:12207-12 (Exhibit 197).

Yu, Wook Joon. et al., "Reproductive Disorders in Pubertal and Adult Phase of the Male Rats Exposed to Vinclozolin during Puberty," *J. Vet. Med. Sci.*, 2004, 66:847-53 (Exhibit 198).

Zambrano, E. et al., "Sex differences in transgenerational alterations of growth and metabolism in progeny (F 2) of female offspring (F1 of rats fed a low protein diet during pregnancy and lactation," *Journal of Physiology*, 2005, 566:225-36 (Exhibit 199).

Zhang, Yun-wu et al., "Nicastrin is Critical for Stability and Trafficking but Not Association of Other Presenilin/γ-Secretase Components," *The Journal of Biological Chemistry*, 2005, 280:17020-6 (Exhibit 200).

Zhong, Cathy Xiaoyan and Marc J. Mass, "Both hypomethylation and hypermethylation of DNA associated with arsenite exposure in cultures of human cells identified by methylation-sensitive arbitrarily-primed PCR," *Toxicology Letters*, 2001, 122:223-34 (Exhibit 201).

* cited by examiner

A.
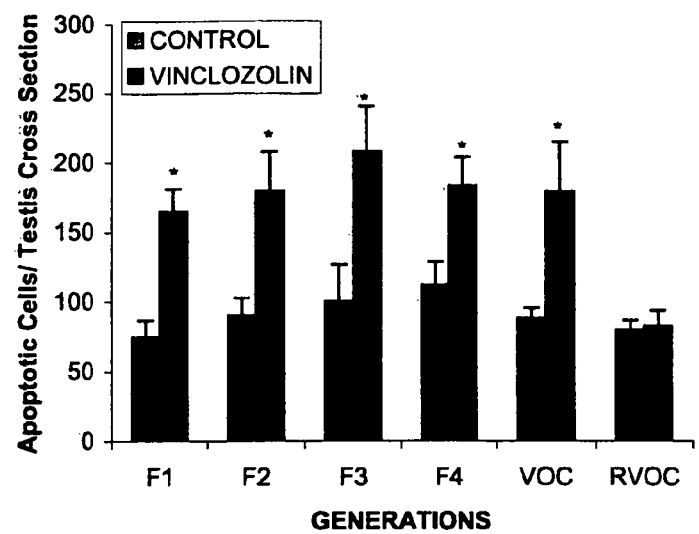
B.
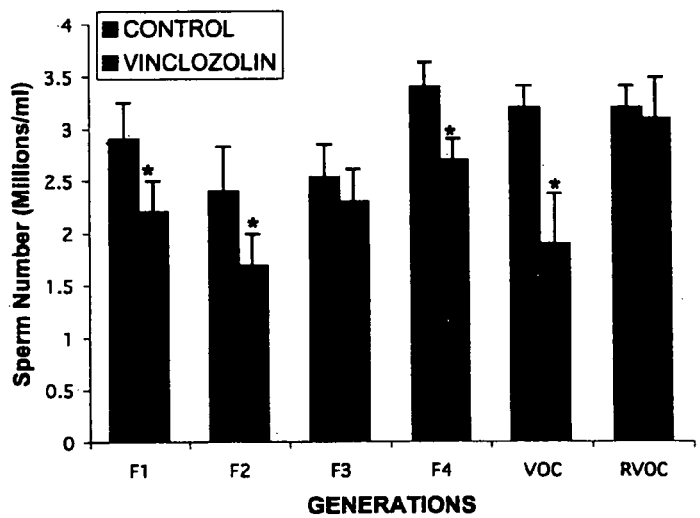
C.
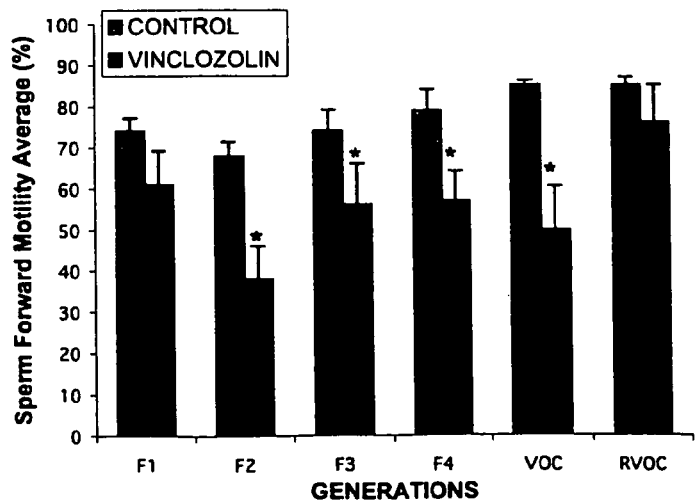
Figure 1

A.
B.
Figure 2

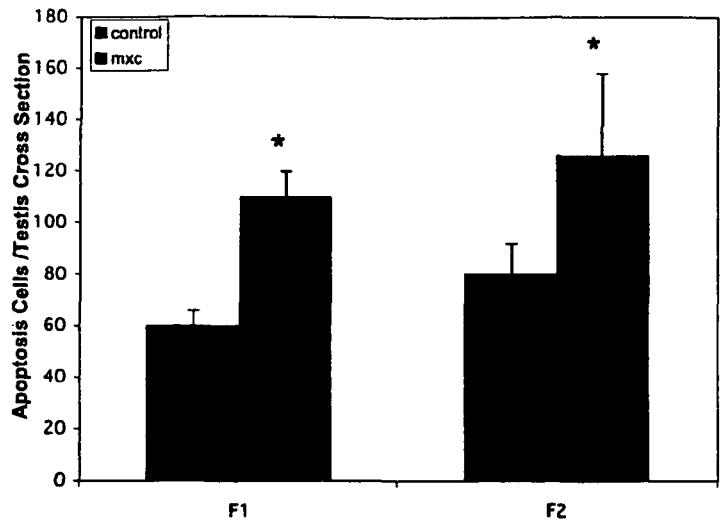
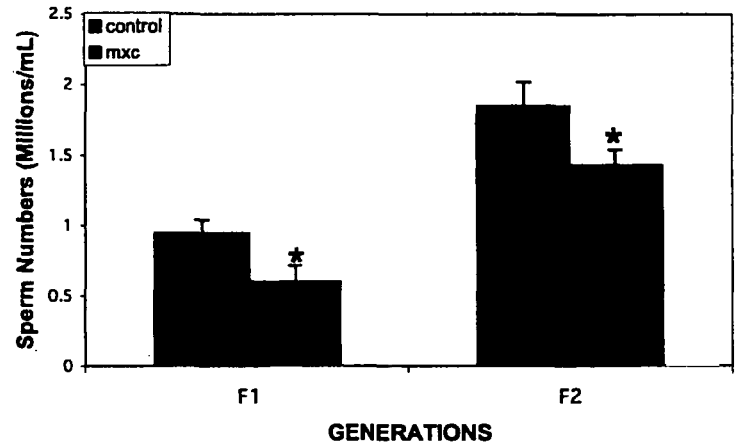
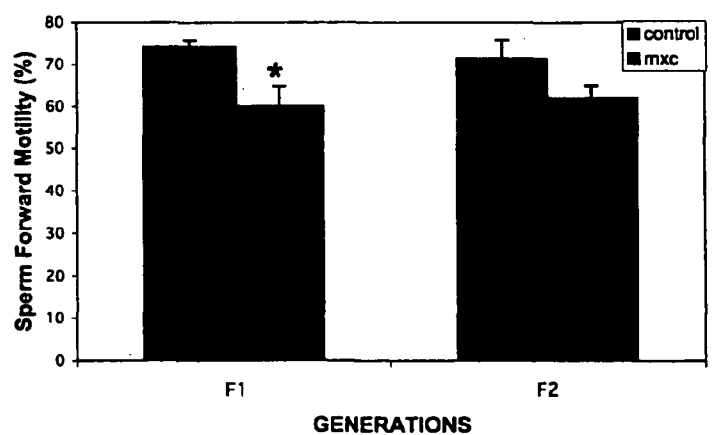
Figure 4

GGCACATACAGAGGAAGGTAGGCAGGCGAGGGACCCAGCAGGTTCTTGACA
GCTTCTCCCCGTGCCCCTCCCCCACTCCCAGGCTGGCATCAAGGGCGGACA
GCGAAGGCCTGCGGGCGTGGTGGCAGGCTGGGGCTGACCTAGGGACAGC
CGGACTATGATGGACACTGTGCCCTGCAAGTAGTGAGTGCCTGCCTCCTGGA
GGTCCTCA

Figure 6

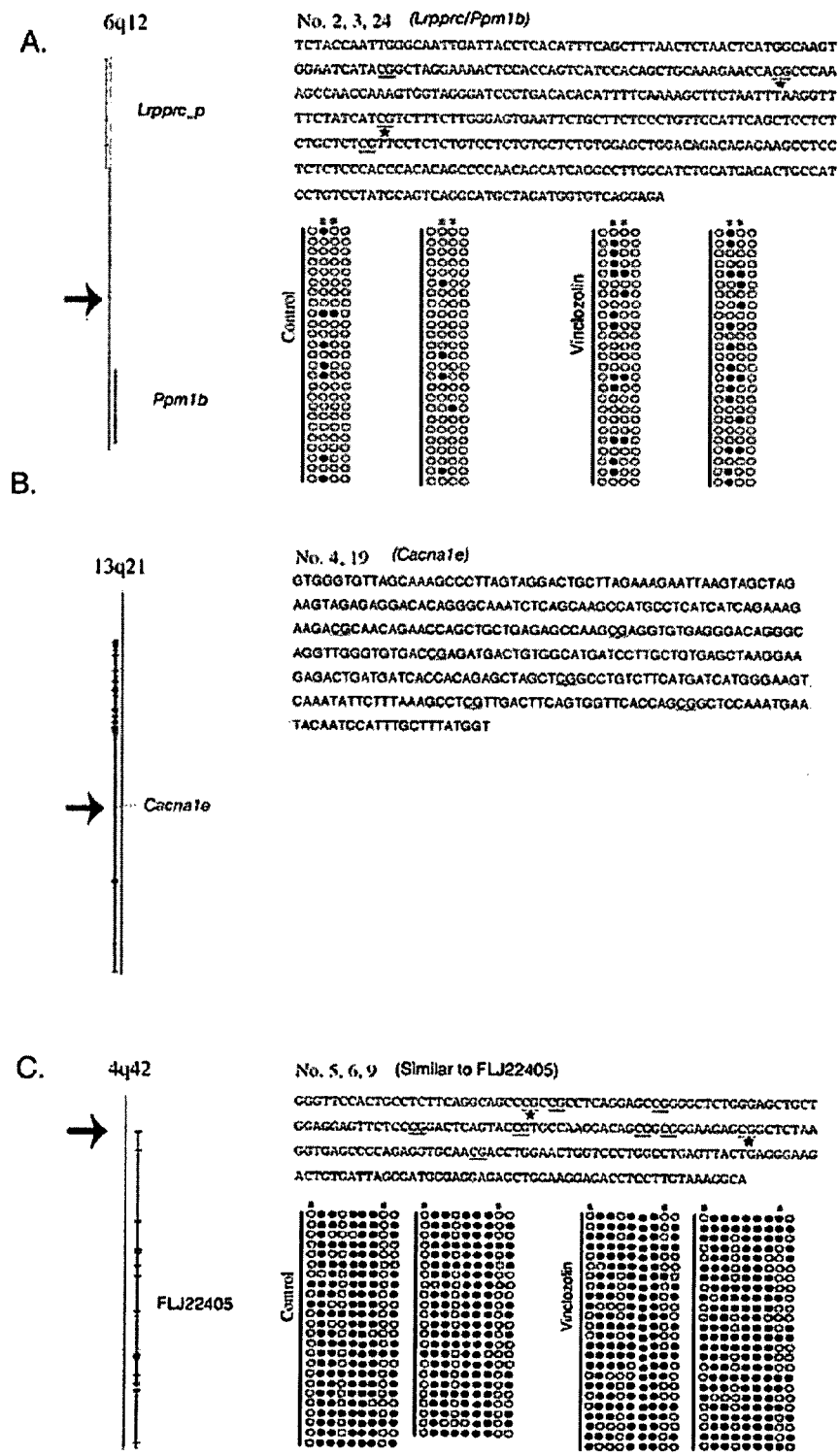
Figure 10 (Part 1)

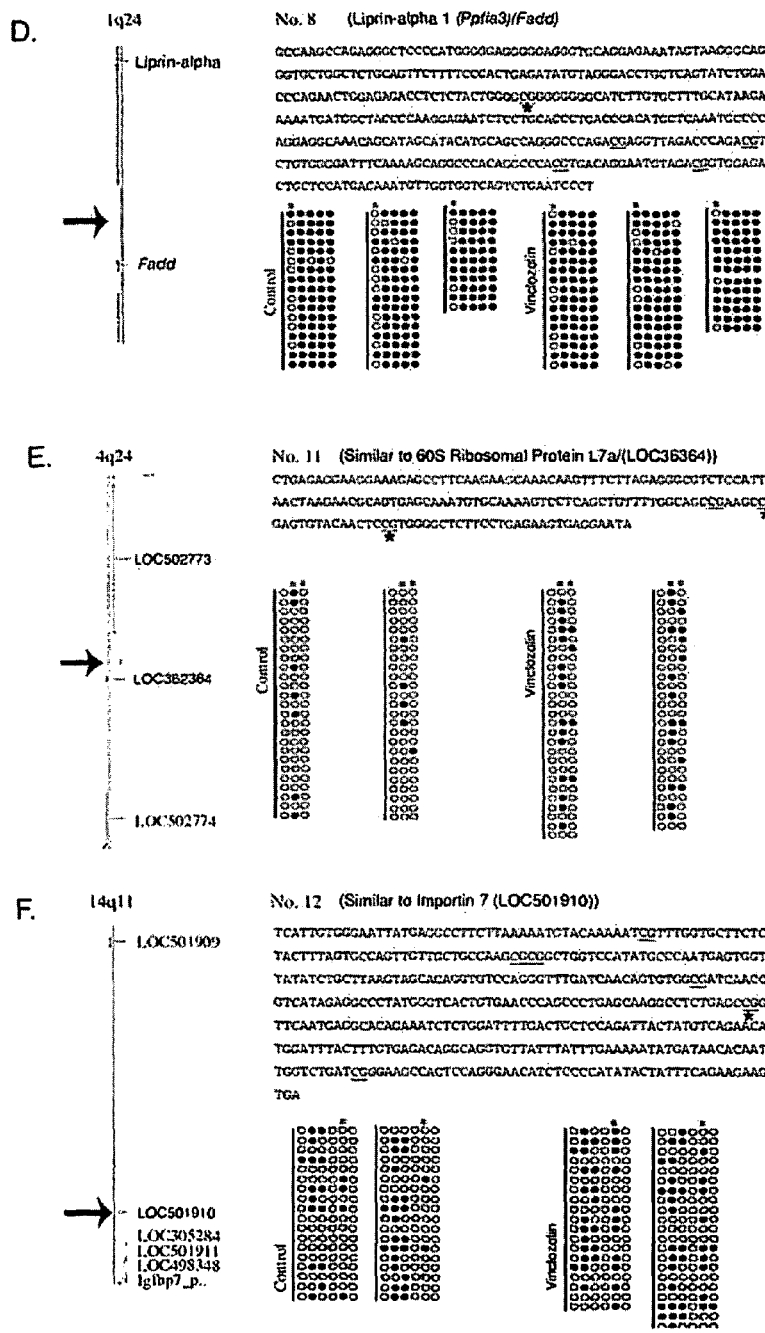
Figure 10 (Part 2)

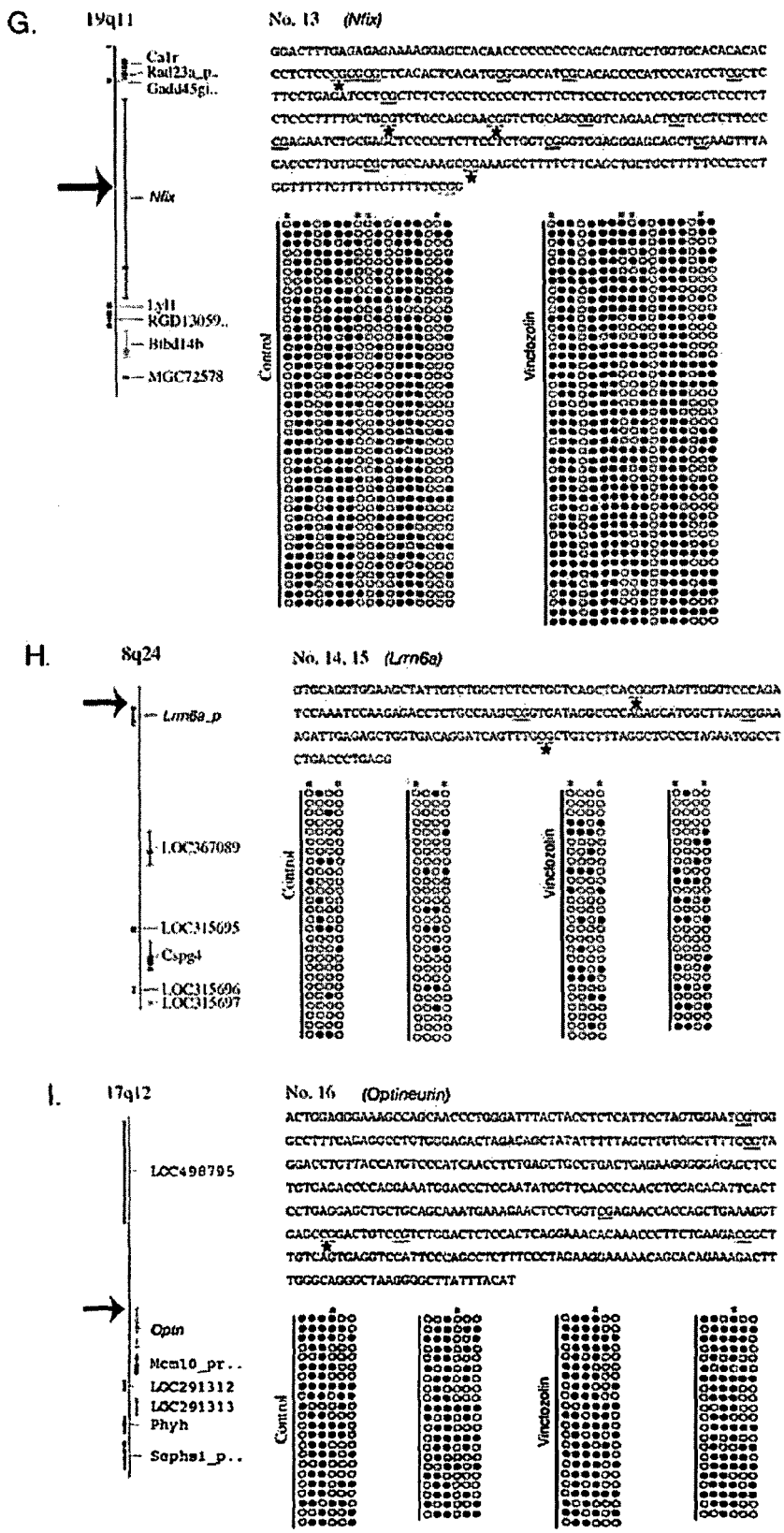
Figure 10 (Part 3)

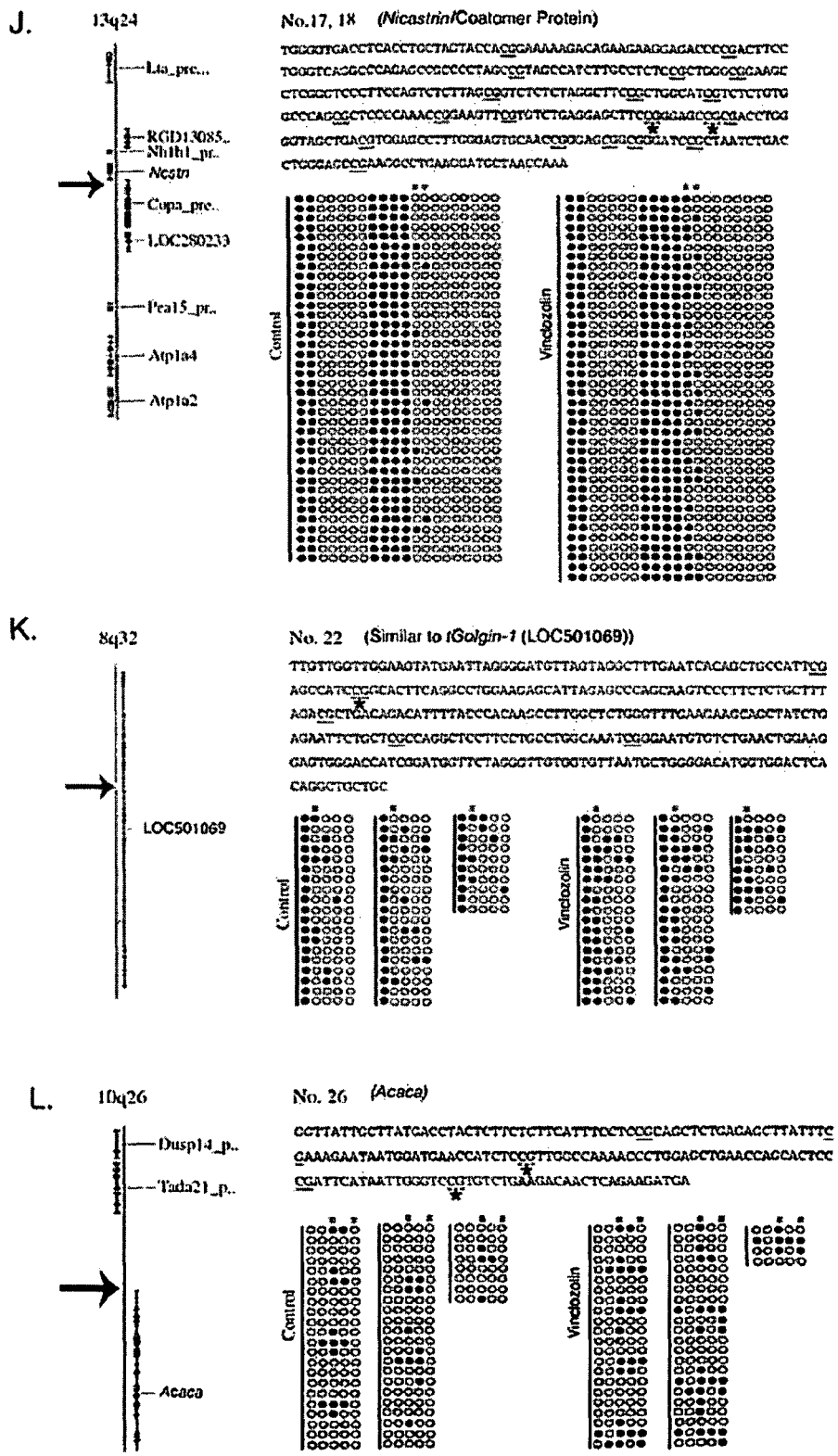
Figure 10 (Part 4)

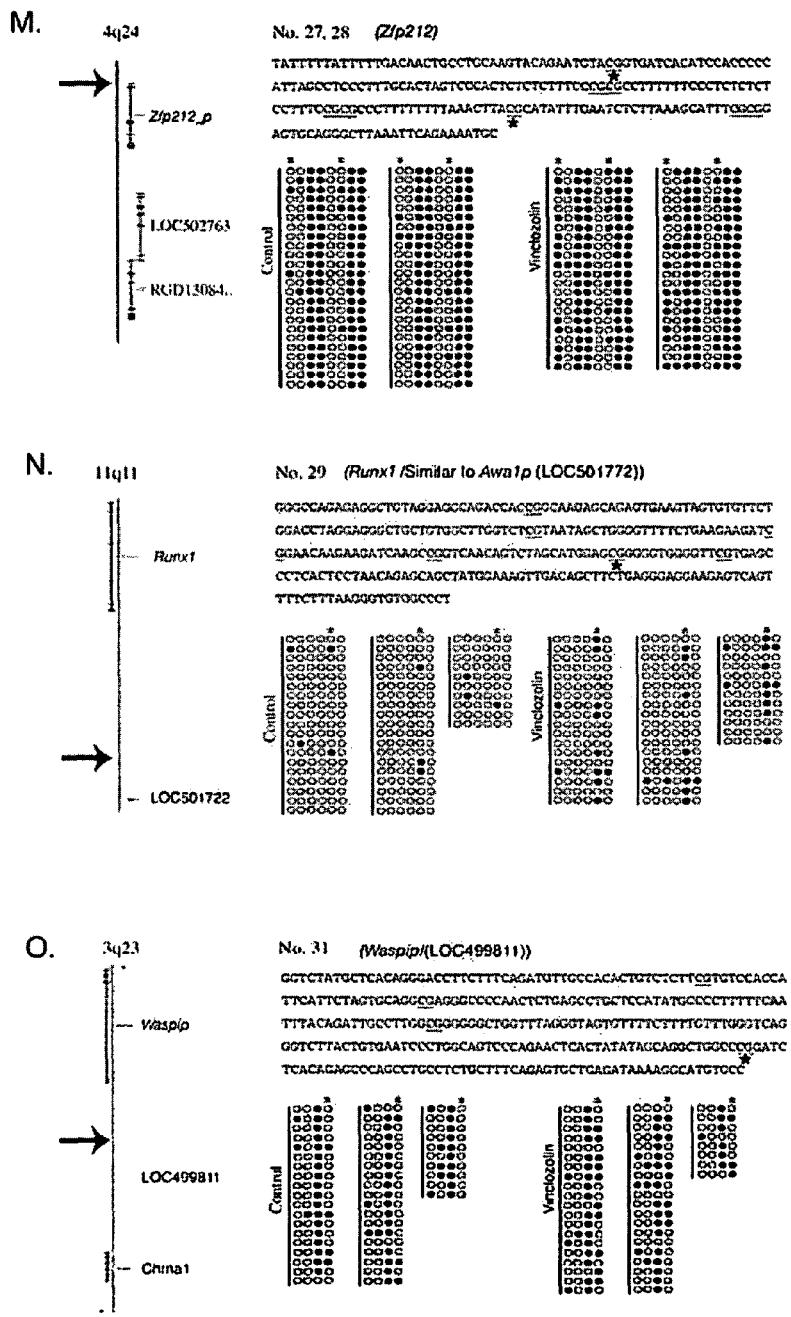
Figure 10(Part 5)

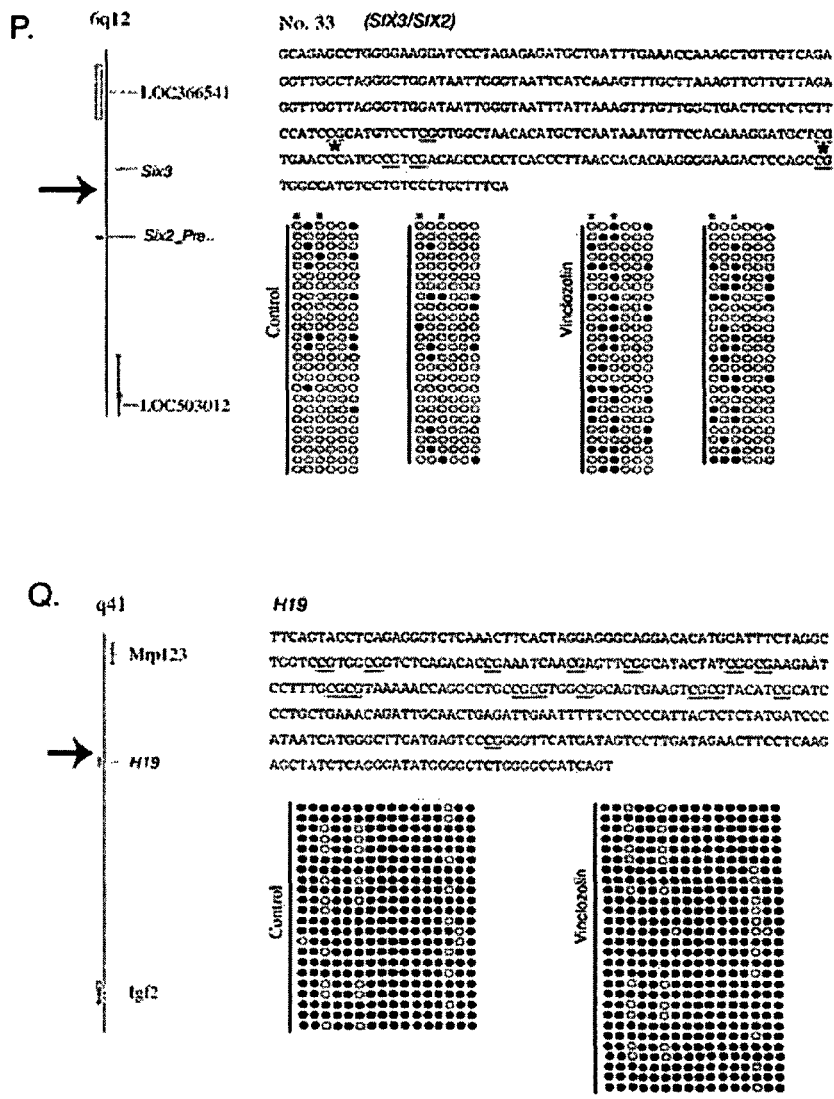
Figure 10 (Part 6)

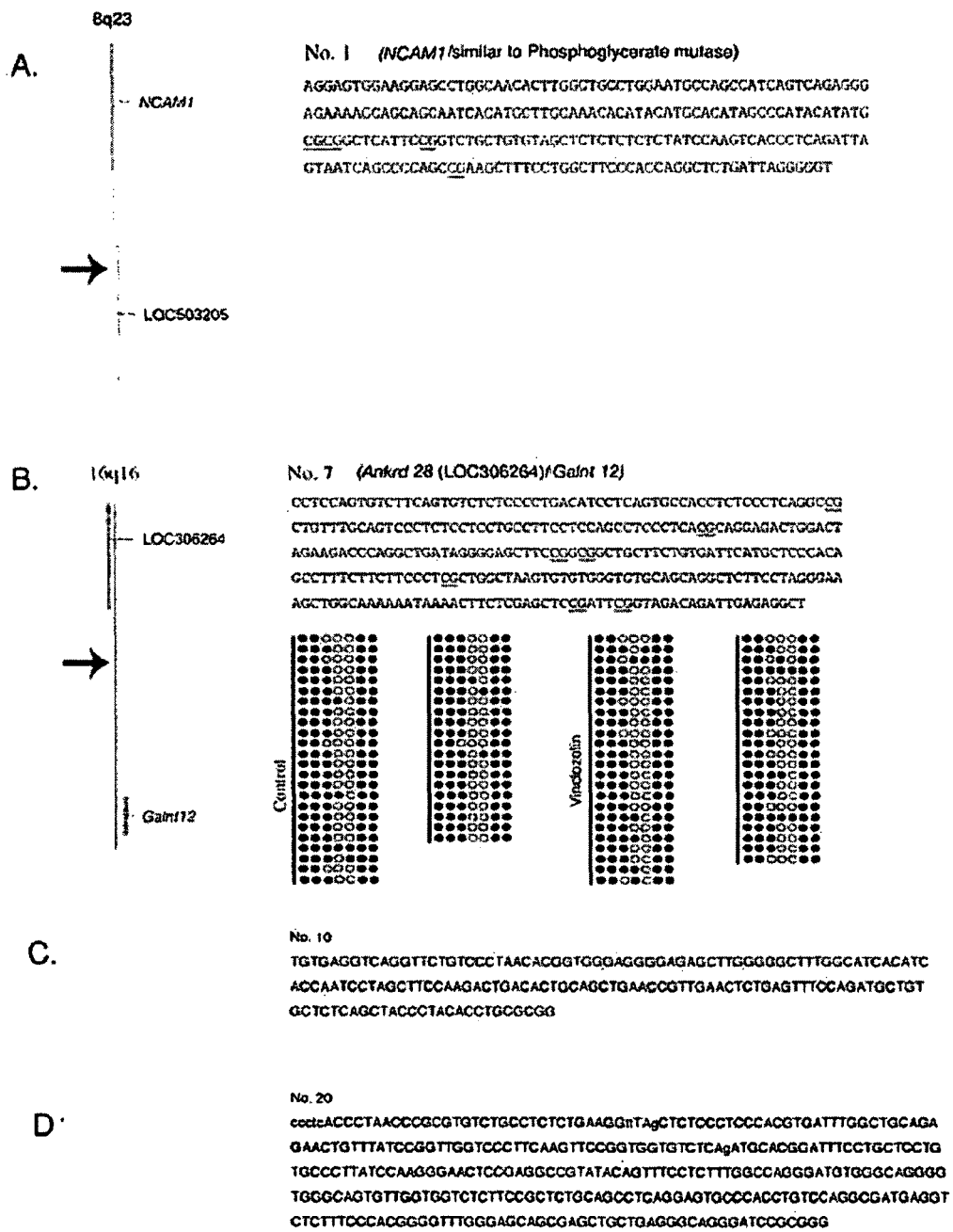
Figure 11 (Part 1)

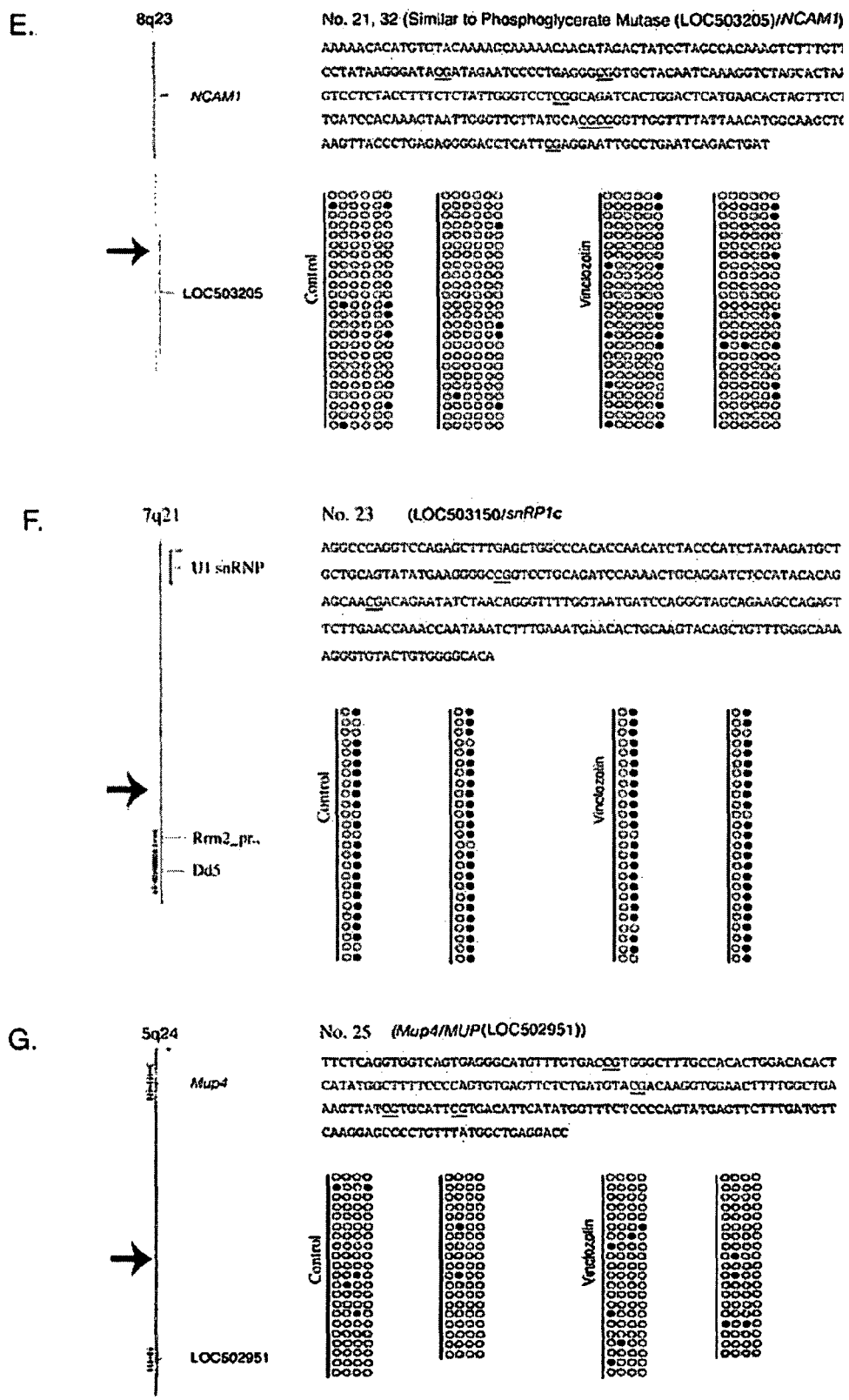
Figure 11 (Part 2)

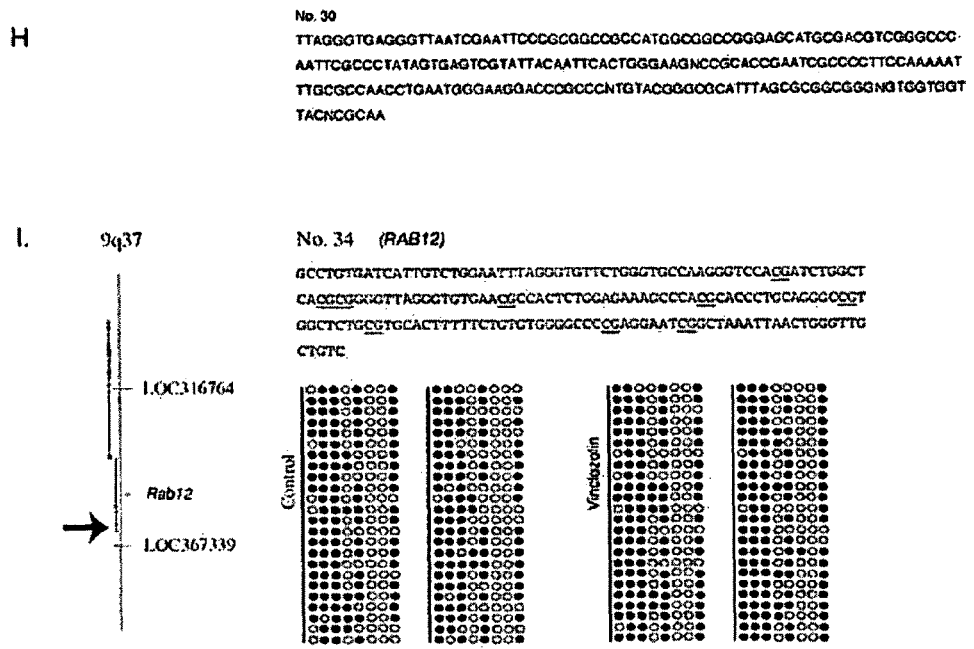
Figure 11 (Part 3), Methylation states of candidates with bisulfite sequencing with the physical chromosome map with alignment (arrow), DNA sequence of interest, and bisulfite results presented.

| | | | | | | | | | | | |
|---|---|---|---|---|---|---|---|---|---|---|---|
| No. 2, 3, 24 | Control | 0 | 22 | 4 | 0 | | | | | | |
| | Vinclozolin | 0 | 46 | 20 | 0 | | | | | | |
| No. 4, 19 | Control | | | | | | | | | | |
| | Vinclozolin | | | | | | | | | | |
| No. 5, 6, 9 | Control | 6 | 96 | 89 | 28 | 96 | 100 | 94 | 6 | 53 | |
| | Vinclozolin | 50 | 86 | 89 | 40 | 96 | 100 | 96 | 35 | 38 | |
| No. 8 | Control | 44 | 98 | 96 | 98 | 98 | | | | | |
| | Vinclozolin | 65 | 100 | 96 | 98 | 98 | | | | | |
| No. 11 | Control | 0 | 22 | 2 | | | | | | | |
| | Vinclozolin | 0 | 49 | 21 | | | | | | | |
| No. 12 | Control | 8 | 55 | 42 | 0 | 17 | 0 | | | | |
| | Vinclozolin | 15 | 63 | 35 | 0 | 50 | 5 | | | | |
| No. 13 | Control | 24 | 93 | 93 | 5 | 95 | 95 | 97 | 17 | 2 | |
| | Vinclozolin | 53 | 100 | 98 | 14 | 100 | 98 | 100 | 60 | 58 | |
| | | 88 | 5 | 97 | 88 | 88 | 2 | 10 | 32 | | |
| | | 95 | 2 | 100 | 100 | 93 | 16 | 51 | 44 | | |
| No. 14, 15 | Control | 2 | 19 | 21 | 6 | | | | | | |
| | Vinclozolin | 27 | 27 | 18 | 27 | | | | | | |
| No. 16 | Control | 30 | 79 | 88 | 28 | 42 | 33 | | | | |
| | Vinclozolin | 33 | 88 | 79 | 79 | 42 | 33 | | | | |
| No. 17, 18 | Control | 100 | 100 | 0 | 0 | 0 | 0 | 0 | 100 | 100 | 100 | 100 |
| | Vinclozolin | 100 | 100 | 0 | 0 | 0 | 0 | 0 | 100 | 100 | 100 | 100 |
| | | 16 | 8 | 0 | 0 | 0 | 0 | 0 | 0 | 0 | | |
| | | 55 | 30 | 0 | 0 | 0 | 0 | 0 | 0 | 0 | | |
| No. 22 | Control | 100 | 17 | 21 | 8 | 8 | | | | | |
| | Vinclozolin | 100 | 67 | 23 | 14 | 19 | | | | | |
| No. 26 | Control | 0 | 6 | 31 | 19 | 0 | | | | | |
| | Vinclozolin | 12 | 6 | 50 | 22 | 28 | | | | | |
| No. 27, 28 | Control | 8 | 10 | 100 | 100 | 0 | 15 | 100 | 100 | | |
| | Vinclozolin | 48 | 14 | 100 | 100 | 2 | 45 | 100 | 100 | | |
| No. 29 | Control | 2 | 6 | 0 | 0 | 13 | 0 | | | | |
| | Vinclozolin | 10 | 0 | 2 | 0 | 48 | 8 | | | | |
| No. 31 | Control | 15 | 10 | 94 | 15 | | | | | | |
| | Vinclozolin | 15 | 8 | 81 | 42 | | | | | | |
| No. 33 | Control | 2 | 24 | 8 | 0 | 0 | 20 | | | | |
| | Vinclozolin | 31 | 33 | 57 | 0 | 0 | 24 | | | | |

Figure 13  Summary of altered methylation changes by bisulfite sequencing analysis for each confirmed candidate. Shaded box are statistically ($p<0.05$) different changes with all methylation percentages for each site presented.

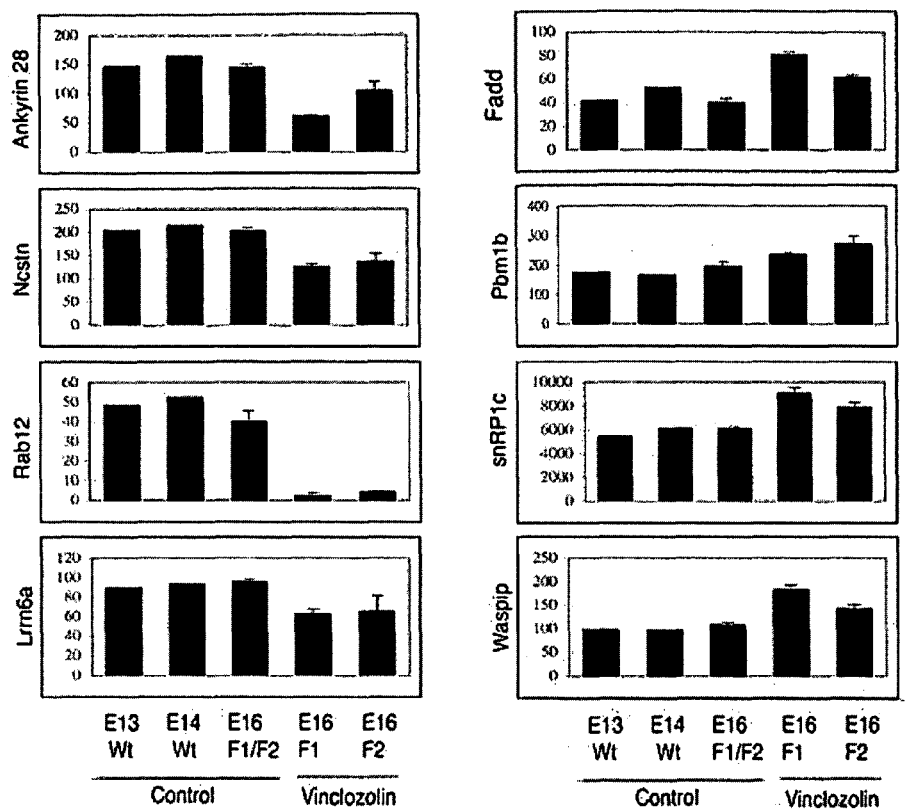
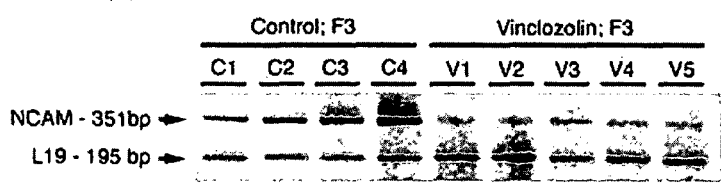
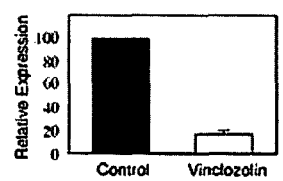
Figure 15

SEQUENCE LISTING

```
<160> NUMBER OF SEQ ID NOS: 116

<210> SEQ ID NO 1
<211> LENGTH: 26
<212> TYPE: DNA
<213> ORGANISM: Artificial
<220> FEATURE:
<223> OTHER INFORMATION: lysophospholipase PCR bisulfite analysis primer

<400> SEQUENCE: 1
ggtatatata gaggaaggta ggtagg                                        26

<210> SEQ ID NO 2
<211> LENGTH: 25
<212> TYPE: DNA
<213> ORGANISM: Artificial
<220> FEATURE:
<223> OTHER INFORMATION: lysophospholipase PCR bisulfite analysis primer

<400> SEQUENCE: 2
taaaaacctc caaaaaacaa acact                                         25

<210> SEQ ID NO 3
<211> LENGTH: 20
<212> TYPE: DNA
<213> ORGANISM: Artificial
<220> FEATURE:
<223> OTHER INFORMATION: Consensus MSRE-PCR Primer - MSAPPCR1

<400> SEQUENCE: 3
aaccctcacc ctaacccccgg                                              20

<210> SEQ ID NO 4
<211> LENGTH: 20
<212> TYPE: DNA
```

```
<213> ORGANISM: Artificial
<220> FEATURE:
<223> OTHER INFORMATION: Consensus MSRE-PCR Primer - MSAPPCR2

<400> SEQUENCE: 4
aaccctcacc ctaaccgcgg                                              20

<210> SEQ ID NO 5
<211> LENGTH: 20
<212> TYPE: DNA
<213> ORGANISM: Artificial
<220> FEATURE:
<223> OTHER INFORMATION: Consensus MSRE-PCR Primer - MSAPPCR3

<400> SEQUENCE: 5
aaccctcacc ctaacccgcg                                              20

<210> SEQ ID NO 6
<211> LENGTH: 20
<212> TYPE: DNA
<213> ORGANISM: Artificial
<220> FEATURE:
<223> OTHER INFORMATION: Consensus MSRE-PCR Primer - MSAPPCR3

<400> SEQUENCE: 6
aaccctcacc ctaaccggcc                                              20

<210> SEQ ID NO 7
<211> LENGTH: 25
<212> TYPE: DNA
<213> ORGANISM: Artificial
<220> FEATURE:
<223> OTHER INFORMATION: Bisulfite Analysis Primer - 01-bsF1

<400> SEQUENCE: 7
aggagtggaa ggagtttggt aatat                                        25

<210> SEQ ID NO 8
<211> LENGTH: 26
<212> TYPE: DNA
<213> ORGANISM: Artificial
<220> FEATURE:
<223> OTHER INFORMATION: Bisulfite Analysis Primer - 01-bsR1

<400> SEQUENCE: 8
taccccctaa tcaaaaccta ataaaa                                       26

<210> SEQ ID NO 9
<211> LENGTH: 24
<212> TYPE: DNA
<213> ORGANISM: Artificial
<220> FEATURE:
<223> OTHER INFORMATION: Bisulfite Analysis Primer - 01-bsF2

<400> SEQUENCE: 9
ggtaatattg gttgtttgga atgt                                         24

<210> SEQ ID NO 10
<211> LENGTH: 25
<212> TYPE: DNA
<213> ORGANISM: Artificial
<220> FEATURE:
<223> OTHER INFORMATION: Bisulfite Analysis Primer - 01-bsR2

<400> SEQUENCE: 10
accccctaat caaaacctaa taaaa                                        25
```

```
<210> SEQ ID NO 11
<211> LENGTH: 30
<212> TYPE: DNA
<213> ORGANISM: Artificial
<220> FEATURE:
<223> OTHER INFORMATION: Bisulfite Analysis Primer - 02-bsF1

<400> SEQUENCE: 11
tttaaatttt agtatttatt aattgggtaa                                    30

<210> SEQ ID NO 12
<211> LENGTH: 25
<212> TYPE: DNA
<213> ORGANISM: Artificial
<220> FEATURE:
<223> OTHER INFORMATION: Bisulfite Analysis Primer - 02-bsF2

<400> SEQUENCE: 12
ttattaattg ggtaattgat tattt                                         25

<210> SEQ ID NO 13
<211> LENGTH: 28
<212> TYPE: DNA
<213> ORGANISM: Artificial
<220> FEATURE:
<223> OTHER INFORMATION: Bisulfite Analysis Primer - 02-bsR1&2

<400> SEQUENCE: 13
tctcctaaca ccatctaaca tacctaac                                      28

<210> SEQ ID NO 14
<211> LENGTH: 30
<212> TYPE: DNA
<213> ORGANISM: Artificial
<220> FEATURE:
<223> OTHER INFORMATION: Bisulfite Analysis Primer - 04-bsF1

<400> SEQUENCE: 14
gtatttatta attgggtaat tgattatttt                                    30

<210> SEQ ID NO 15
<211> LENGTH: 28
<212> TYPE: DNA
<213> ORGANISM: Artificial
<220> FEATURE:
<223> OTHER INFORMATION: Bisulfite Analysis Primer - 04-bsR1

<400> SEQUENCE: 15
tctcctaaca ccatctaaca tacctaac                                      28

<210> SEQ ID NO 16
<211> LENGTH: 30
<212> TYPE: DNA
<213> ORGANISM: Artificial
<220> FEATURE:
<223> OTHER INFORMATION: Bisulfite Analysis Primer - 04-bsF2

<400> SEQUENCE: 16
attaattggg taattgatta ttttatattt                                    30

<210> SEQ ID NO 17
<211> LENGTH: 25
<212> TYPE: DNA
<213> ORGANISM: Artificial
<220> FEATURE:
<223> OTHER INFORMATION: Bisulfite Analysis Primer - 04-bsR2
```

-continued

<400> SEQUENCE: 17
accaaaacct aatactatta aaact				25

<210> SEQ ID NO 18
<211> LENGTH: 20
<212> TYPE: DNA
<213> ORGANISM: Artificial
<220> FEATURE:
<223> OTHER INFORMATION: Bisulfite Analysis Primer - 05-bsF1

<400> SEQUENCE: 18
tttgagggga tttgaggttg				20

<210> SEQ ID NO 19
<211> LENGTH: 26
<212> TYPE: DNA
<213> ORGANISM: Artificial
<220> FEATURE:
<223> OTHER INFORMATION: Bisulfite Analysis Primer - 05-bsF2

<400> SEQUENCE: 19
gggttttatt gttttttag gtagtt				26

<210> SEQ ID NO 20
<211> LENGTH: 25
<212> TYPE: DNA
<213> ORGANISM: Artificial
<220> FEATURE:
<223> OTHER INFORMATION: Bisulfite Analysis Primer - 05-bsR1&2

<400> SEQUENCE: 20
tacaaaaaaa tctccttcca actct				25

<210> SEQ ID NO 21
<211> LENGTH: 26
<212> TYPE: DNA
<213> ORGANISM: Artificial
<220> FEATURE:
<223> OTHER INFORMATION: Bisulfite Analysis Primer - 07-bsF1

<400> SEQUENCE: 21
ttattttagt ttttttgtt tttttt				26

<210> SEQ ID NO 22
<211> LENGTH: 27
<212> TYPE: DNA
<213> ORGANISM: Artificial
<220> FEATURE:
<223> OTHER INFORMATION: Bisulfite Analysis Primer - 07-bsR1

<400> SEQUENCE: 22
ttaatcttaa aatacccct ttatatc				27

<210> SEQ ID NO 23
<211> LENGTH: 26
<212> TYPE: DNA
<213> ORGANISM: Artificial
<220> FEATURE:
<223> OTHER INFORMATION: Bisulfite Analysis Primer - 07-bsF2

<400> SEQUENCE: 23
tttttagtgt tttagtgtt tttttt				26

<210> SEQ ID NO 24
<211> LENGTH: 26
<212> TYPE: DNA

<213> ORGANISM: Artificial
<220> FEATURE:
<223> OTHER INFORMATION: Bisulfite Analysis Primer - 07-bsR2

<400> SEQUENCE: 24
ctatacaacc tctcaatcta tctacc                                          26

<210> SEQ ID NO 25
<211> LENGTH: 25
<212> TYPE: DNA
<213> ORGANISM: Artificial
<220> FEATURE:
<223> OTHER INFORMATION: Bisulfite Analysis Primer - 08-bsF1

<400> SEQUENCE: 25
aatagtaagg gtagggtgtt ggttt                                           25

<210> SEQ ID NO 26
<211> LENGTH: 25
<212> TYPE: DNA
<213> ORGANISM: Artificial
<220> FEATURE:
<223> OTHER INFORMATION: Bisulfite Analysis Primer - 08-bsF2

<400> SEQUENCE: 26
gttaagttag agggtttttt atggg                                           25

<210> SEQ ID NO 27
<211> LENGTH: 25
<212> TYPE: DNA
<213> ORGANISM: Artificial
<220> FEATURE:
<223> OTHER INFORMATION: Bisulfite Analysis Primer - 08-bsR1&2

<400> SEQUENCE: 27
aaaattcaaa ctaaccacca acatt                                           25

<210> SEQ ID NO 28
<211> LENGTH: 29
<212> TYPE: DNA
<213> ORGANISM: Artificial
<220> FEATURE:
<223> OTHER INFORMATION: Bisulfite Analysis Primer - 11-bsF1

<400> SEQUENCE: 28
tgataaaata agattaagaa ggttgagag                                       29

<210> SEQ ID NO 29
<211> LENGTH: 26
<212> TYPE: DNA
<213> ORGANISM: Artificial
<220> FEATURE:
<223> OTHER INFORMATION: Bisulfite Analysis Primer - 11-bsF2

<400> SEQUENCE: 29
ttgagaggaa ggaaagagtt tttaag                                          26

<210> SEQ ID NO 30
<211> LENGTH: 25
<212> TYPE: DNA
<213> ORGANISM: Artificial
<220> FEATURE:
<223> OTHER INFORMATION: Bisulfite Analysis Primer - 11-bsR1&2

<400> SEQUENCE: 30
tattcctcac ttctcaaaaa aaacc                                           25

```
<210> SEQ ID NO 31
<211> LENGTH: 25
<212> TYPE: DNA
<213> ORGANISM: Artificial
<220> FEATURE:
<223> OTHER INFORMATION: Bisulfite Analysis Primer - 12-bsF1&2

<400> SEQUENCE: 31
ttattgtggg aattatgagg ttttt                                   25

<210> SEQ ID NO 32
<211> LENGTH: 28
<212> TYPE: DNA
<213> ORGANISM: Artificial
<220> FEATURE:
<223> OTHER INFORMATION: Bisulfite Analysis Primer - 12-bsR1

<400> SEQUENCE: 32
tcaatcttct tctaaaataa tatataaa                                28

<210> SEQ ID NO 33
<211> LENGTH: 30
<212> TYPE: DNA
<213> ORGANISM: Artificial
<220> FEATURE:
<223> OTHER INFORMATION: Bisulfite Analysis Primer - 12-bsR2

<400> SEQUENCE: 33
ttaaactata ccctattaac tcaaataaat                              30

<210> SEQ ID NO 34
<211> LENGTH: 28
<212> TYPE: DNA
<213> ORGANISM: Artificial
<220> FEATURE:
<223> OTHER INFORMATION: Bisulfite Analysis Primer - 13-bsF1&2

<400> SEQUENCE: 34
ggattttgag agagaaaagg agttataa                                28

<210> SEQ ID NO 35
<211> LENGTH: 25
<212> TYPE: DNA
<213> ORGANISM: Artificial
<220> FEATURE:
<223> OTHER INFORMATION: Bisulfite Analysis Primer - 13-bsR1&2

<400> SEQUENCE: 35
aaacaaaaac aaaaaccaaa aaaaa                                   25

<210> SEQ ID NO 36
<211> LENGTH: 25
<212> TYPE: DNA
<213> ORGANISM: Artificial
<220> FEATURE:
<223> OTHER INFORMATION: Bisulfite Analysis Primer - 14-bsF1&2

<400> SEQUENCE: 36
gtgtaggtgg aagttattgt ttggt                                   25

<210> SEQ ID NO 37
<211> LENGTH: 24
<212> TYPE: DNA
<213> ORGANISM: Artificial
<220> FEATURE:
<223> OTHER INFORMATION: Bisulfite Analysis Primer - 14-bsR1
```

```
<400> SEQUENCE: 37
tcctcaaaat caaaaaccat tcta                                          24

<210> SEQ ID NO 38
<211> LENGTH: 25
<212> TYPE: DNA
<213> ORGANISM: Artificial
<220> FEATURE:
<223> OTHER INFORMATION: Bisulfite Analysis Primer - 14-bsR2

<400> SEQUENCE: 38
cctcaaaatc aaaaaccatt ctaaa                                         25

<210> SEQ ID NO 39
<211> LENGTH: 25
<212> TYPE: DNA
<213> ORGANISM: Artificial
<220> FEATURE:
<223> OTHER INFORMATION: Bisulfite Analysis Primer - 16-bsF1&2

<400> SEQUENCE: 39
attggaggga aagttagtaa ttttg                                         25

<210> SEQ ID NO 40
<211> LENGTH: 25
<212> TYPE: DNA
<213> ORGANISM: Artificial
<220> FEATURE:
<223> OTHER INFORMATION: Bisulfite Analysis Primer - 16-bsR1

<400> SEQUENCE: 40
aaaatacaac cctacaccat catac                                         25

<210> SEQ ID NO 41
<211> LENGTH: 25
<212> TYPE: DNA
<213> ORGANISM: Artificial
<220> FEATURE:
<223> OTHER INFORMATION: Bisulfite Analysis Primer - 16-bsR2

<400> SEQUENCE: 41
tataaataaa ccccttaacc ctacc                                         25

<210> SEQ ID NO 42
<211> LENGTH: 25
<212> TYPE: DNA
<213> ORGANISM: Artificial
<220> FEATURE:
<223> OTHER INFORMATION: Bisulfite Analysis Primer - 17-bsF1&2

<400> SEQUENCE: 42
ggggtgattt tatttgttag tatta                                         25

<210> SEQ ID NO 43
<211> LENGTH: 25
<212> TYPE: DNA
<213> ORGANISM: Artificial
<220> FEATURE:
<223> OTHER INFORMATION: Bisulfite Analysis Primer - 17-bsR1

<400> SEQUENCE: 43
taaactcttc caataaaccc aattc                                         25

<210> SEQ ID NO 44
<211> LENGTH: 25
<212> TYPE: DNA
```

```
<213> ORGANISM: Artificial
<220> FEATURE:
<223> OTHER INFORMATION: Bisulfite Analysis Primer - 17-bsR2

<400> SEQUENCE: 44
tttaattaac atccttcaaa ccttc                                      25

<210> SEQ ID NO 45
<211> LENGTH: 30
<212> TYPE: DNA
<213> ORGANISM: Artificial
<220> FEATURE:
<223> OTHER INFORMATION: Bisulfite Analysis Primer - 21-bsF1&2

<400> SEQUENCE: 45
aaaaatatat gtgtataaaa gtaaaaataa                                 30

<210> SEQ ID NO 46
<211> LENGTH: 25
<212> TYPE: DNA
<213> ORGANISM: Artificial
<220> FEATURE:
<223> OTHER INFORMATION: Bisulfite Analysis Primer - 21-bsR1&2

<400> SEQUENCE: 46
atcaatctaa ttcaaacaat tcctc                                      25

<210> SEQ ID NO 47
<211> LENGTH: 26
<212> TYPE: DNA
<213> ORGANISM: Artificial
<220> FEATURE:
<223> OTHER INFORMATION: Bisulfite Analysis Primer - 22-bsF1

<400> SEQUENCE: 47
atttgttggt tggaagtatg aattag                                     26

<210> SEQ ID NO 48
<211> LENGTH: 26
<212> TYPE: DNA
<213> ORGANISM: Artificial
<220> FEATURE:
<223> OTHER INFORMATION: Bisulfite Analysis Primer - 22-bsF2

<400> SEQUENCE: 48
atttgttggt tggaagtatg aattag                                     26

<210> SEQ ID NO 49
<211> LENGTH: 26
<212> TYPE: DNA
<213> ORGANISM: Artificial
<220> FEATURE:
<223> OTHER INFORMATION: Bisulfite Analysis Primer - 22-bsR1&2

<400> SEQUENCE: 49
acaacaacct ataaatccac catatc                                     26

<210> SEQ ID NO 50
<211> LENGTH: 25
<212> TYPE: DNA
<213> ORGANISM: Artificial
<220> FEATURE:
<223> OTHER INFORMATION: Bisulfite Analysis Primer - 23-bsF1

<400> SEQUENCE: 50
gggtagtgta ggagagatgg tttta                                      25
```

```
<210> SEQ ID NO 51
<211> LENGTH: 26
<212> TYPE: DNA
<213> ORGANISM: Artificial
<220> FEATURE:
<223> OTHER INFORMATION: Bisulfite Analysis Primer - 23-bsF2

<400> SEQUENCE: 51
aggtttaggt ttagagtttt gagttg                                          26

<210> SEQ ID NO 52
<211> LENGTH: 25
<212> TYPE: DNA
<213> ORGANISM: Artificial
<220> FEATURE:
<223> OTHER INFORMATION: Bisulfite Analysis Primer - 23-bsR1&2

<400> SEQUENCE: 52 tatacccac aatacaccct tttac                                            25

<210> SEQ ID NO 53
<211> LENGTH: 25
<212> TYPE: DNA
<213> ORGANISM: Artificial
<220> FEATURE:
<223> OTHER INFORMATION: Bisulfite Analysis Primer - 25-bsF1&2

<400> SEQUENCE: 53
tttttaggtg gttagtgagg gtatg                                           25

<210> SEQ ID NO 54
<211> LENGTH: 25
<212> TYPE: DNA
<213> ORGANISM: Artificial
<220> FEATURE:
<223> OTHER INFORMATION: Bisulfite Analysis Primer - 25-bsR1

<400> SEQUENCE: 54
aaaaaatcct caaccataaa caaaa                                           25

<210> SEQ ID NO 55
<211> LENGTH: 25
<212> TYPE: DNA
<213> ORGANISM: Artificial
<220> FEATURE:
<223> OTHER INFORMATION: Bisulfite Analysis Primer - 25-bsR2

<400> SEQUENCE: 55
aatcctcaac cataaacaaa aactc                                           25

<210> SEQ ID NO 56
<211> LENGTH: 27
<212> TYPE: DNA
<213> ORGANISM: Artificial
<220> FEATURE:
<223> OTHER INFORMATION: Bisulfite Analysis Primer - 26-bsF1

<400> SEQUENCE: 56
ggttattgtt tatgatttat ttttttt                                         27

<210> SEQ ID NO 57
<211> LENGTH: 25
<212> TYPE: DNA
<213> ORGANISM: Artificial
<220> FEATURE:
<223> OTHER INFORMATION: Bisulfite Analysis Primer - 26-bsR1
```

```
<400> SEQUENCE: 57
tctcctctaa atccaacttt accaa                                    25

<210> SEQ ID NO 58
<211> LENGTH: 26
<212> TYPE: DNA
<213> ORGANISM: Artificial
<220> FEATURE:
<223> OTHER INFORMATION: Bisulfite Analysis Primer - 26-bsR2

<400> SEQUENCE: 58
tcatcttcta aattatcttc aaacac                                   26

<210> SEQ ID NO 59
<211> LENGTH: 30
<212> TYPE: DNA
<213> ORGANISM: Artificial
<220> FEATURE:
<223> OTHER INFORMATION: Bisulfite Analysis Primer - 27-bsF1

<400> SEQUENCE: 59
tatttttatt tttgataatt gtttgtaagt                               30

<210> SEQ ID NO 60
<211> LENGTH: 27
<212> TYPE: DNA
<213> ORGANISM: Artificial
<220> FEATURE:
<223> OTHER INFORMATION: Bisulfite Analysis Primer - 27-bsR1

<400> SEQUENCE: 60
aaaacaacaa cctaaaaatt caatcat                                  27

<210> SEQ ID NO 61
<211> LENGTH: 30
<212> TYPE: DNA
<213> ORGANISM: Artificial
<220> FEATURE:
<223> OTHER INFORMATION: Bisulfite Analysis Primer - 27-bsF2

<400> SEQUENCE: 61 attttttattt ttgataattg tttgtaagta                              30

<210> SEQ ID NO 62
<211> LENGTH: 28
<212> TYPE: DNA
<213> ORGANISM: Artificial
<220> FEATURE:
<223> OTHER INFORMATION: Bisulfite Analysis Primer - 27-bsR2

<400> SEQUENCE: 62
acattttcta aatttaaacc ctacactc                                 28

<210> SEQ ID NO 63
<211> LENGTH: 25
<212> TYPE: DNA
<213> ORGANISM: Artificial
<220> FEATURE:
<223> OTHER INFORMATION: Bisulfite Analysis Primer - 29-bsF1

<400> SEQUENCE: 63
gggttagaga ggttgtagga ggtag                                    25

<210> SEQ ID NO 64
<211> LENGTH: 26
<212> TYPE: DNA
```

-continued

<213> ORGANISM: Artificial
<220> FEATURE:
<223> OTHER INFORMATION: Bisulfite Analysis Primer - 29-bsR1

<400> SEQUENCE: 64
aaaaccacac ccttaaaaaa aactaa                                          26

<210> SEQ ID NO 65
<211> LENGTH: 27
<212> TYPE: DNA
<213> ORGANISM: Artificial
<220> FEATURE:
<223> OTHER INFORMATION: Bisulfite Analysis Primer - 31-bsF1

<400> SEQUENCE: 65
tggtttatgt ttatagggat tttttt                                          27

<210> SEQ ID NO 66
<211> LENGTH: 26
<212> TYPE: DNA
<213> ORGANISM: Artificial
<220> FEATURE:
<223> OTHER INFORMATION: Bisulfite Analysis Primer - 31-bsF2

<400> SEQUENCE: 66
ggtttatgtt tatagggatt tttttt                                          26

<210> SEQ ID NO 67
<211> LENGTH: 29
<212> TYPE: DNA
<213> ORGANISM: Artificial
<220> FEATURE:
<223> OTHER INFORMATION: Bisulfite Analysis Primer - 31-bsR1&2

<400> SEQUENCE: 67
aacacatacc ttttatctca acactctaa                                       29

<210> SEQ ID NO 68
<211> LENGTH: 25
<212> TYPE: DNA
<213> ORGANISM: Artificial
<220> FEATURE:
<223> OTHER INFORMATION: Bisulfite Analysis Primer - 33-bsF1&2

<400> SEQUENCE: 68
gtagagtttg gggaaggatt tttag                                           25

<210> SEQ ID NO 69
<211> LENGTH: 25
<212> TYPE: DNA
<213> ORGANISM: Artificial
<220> FEATURE:
<223> OTHER INFORMATION: Bisulfite Analysis Primer - 33-bsR1

<400> SEQUENCE: 69
acccaaaaat aaaaacaaaa acaaa                                           25

<210> SEQ ID NO 70
<211> LENGTH: 25
<212> TYPE: DNA
<213> ORGANISM: Artificial
<220> FEATURE:
<223> OTHER INFORMATION: Bisulfite Analysis Primer - 33-bsR2

<400> SEQUENCE: 70
aaaaacaaaa acaaaacata accac                                           25

```
<210> SEQ ID NO 71
<211> LENGTH: 26
<212> TYPE: DNA
<213> ORGANISM: Artificial
<220> FEATURE:
<223> OTHER INFORMATION: Bisulfite Analysis Primer - 34-bsF1&2

<400> SEQUENCE: 71
gtttgtgatt attgtttgga atttag                                          26

<210> SEQ ID NO 72
<211> LENGTH: 25
<212> TYPE: DNA
<213> ORGANISM: Artificial
<220> FEATURE:
<223> OTHER INFORMATION: Bisulfite Analysis Primer - 34-bsR1

<400> SEQUENCE: 72
caaaaatcta aaaaaacaa caacc                                            25

<210> SEQ ID NO 73
<211> LENGTH: 24
<212> TYPE: DNA
<213> ORGANISM: Artificial
<220> FEATURE:
<223> OTHER INFORMATION: Bisulfite Analysis Primer - 34-bsR2

<400> SEQUENCE: 73
aacaacaacc caattaattt aacc                                            24

<210> SEQ ID NO 74
<211> LENGTH: 26
<212> TYPE: DNA
<213> ORGANISM: Artificial
<220> FEATURE:
<223> OTHER INFORMATION: Bisulfite Analysis Primer - H19-bsF1

<400> SEQUENCE: 74
aggatatatg tattttagg ttggtt                                           26

<210> SEQ ID NO 75
<211> LENGTH: 24
<212> TYPE: DNA
<213> ORGANISM: Artificial
<220> FEATURE:
<223> OTHER INFORMATION: Bisulfite Analysis Primer - H19-bsR1

<400> SEQUENCE: 75
actaataacc ccaaaacccc atat                                            24

<210> SEQ ID NO 76
<211> LENGTH: 20
<212> TYPE: DNA
<213> ORGANISM: Artificial
<220> FEATURE:
<223> OTHER INFORMATION: Gene Specific MSRE-PCR Primer - 01-GRF1

<400> SEQUENCE: 76
agccatcagt cagagggaga                                                 20

<210> SEQ ID NO 77
<211> LENGTH: 20
<212> TYPE: DNA
<213> ORGANISM: Artificial
<220> FEATURE:
<223> OTHER INFORMATION: Gene Specific MSRE-PCR Primer - 01-GRR1
```

<210> SEQ ID NO 77

```
<400> SEQUENCE: 77
gccattgatt cccagaagtc                                              20
```

```
<210> SEQ ID NO 78
<211> LENGTH: 20
<212> TYPE: DNA
<213> ORGANISM: Artificial
<220> FEATURE:
<223> OTHER INFORMATION: Gene Specific MSRE-PCR Primer - 14-GRF1

<400> SEQUENCE: 78
ctccctctct ccctttttgct                                             20
```

```
<210> SEQ ID NO 79
<211> LENGTH: 20
<212> TYPE: DNA
<213> ORGANISM: Artificial
<220> FEATURE:
<223> OTHER INFORMATION: Gene Specific MSRE-PCR Primer - 14-GRR1

<400> SEQUENCE: 79
tgacagaggg ctggtctctc                                              20
```

```
<210> SEQ ID NO 80
<211> LENGTH: 22
<212> TYPE: DNA
<213> ORGANISM: Artificial
<220> FEATURE:
<223> OTHER INFORMATION: Gene Specific MSRE-PCR Primer - 17-GRF1

<400> SEQUENCE: 80
gggtcccttc cagtctctta gc                                           22
```

```
<210> SEQ ID NO 81
<211> LENGTH: 22
<212> TYPE: DNA
<213> ORGANISM: Artificial
<220> FEATURE:
<223> OTHER INFORMATION: Gene Specific MSRE-PCR Primer - 17-GRR1

<400> SEQUENCE: 81
agtgactgac tccggaaaaa gc                                           22
```

```
<210> SEQ ID NO 82
<211> LENGTH: 22
<212> TYPE: DNA
<213> ORGANISM: Artificial
<220> FEATURE:
<223> OTHER INFORMATION: Gene Specific MSRE-PCR Primer - 27-GRF1

<400> SEQUENCE: 82
atccctgcat gaggactacg tt                                           22
```

```
<210> SEQ ID NO 83
<211> LENGTH: 22
<212> TYPE: DNA
<213> ORGANISM: Artificial
<220> FEATURE:
<223> OTHER INFORMATION: Gene Specific MSRE-PCR Primer - 27-GRR1

<400> SEQUENCE: 83
ccgtgttgat acaaggtgca tt                                           22
```

```
<210> SEQ ID NO 84
<211> LENGTH: 20
<212> TYPE: DNA
```

-continued

<210> SEQ ID NO 84
<211> LENGTH: 20
<212> TYPE: DNA
<213> ORGANISM: Artificial
<220> FEATURE:
<223> OTHER INFORMATION: Gene Specific MSRE-PCR Primer - 33-GRF1

<400> SEQUENCE: 84
ttgtcagagg ttggctaggg                                              20

<210> SEQ ID NO 85
<211> LENGTH: 20
<212> TYPE: DNA
<213> ORGANISM: Artificial
<220> FEATURE:
<223> OTHER INFORMATION: Gene Specific MSRE-PCR Primer - 33-GRR1

<400> SEQUENCE: 85
cgccacagca tgagtaaaga                                              20

<210> SEQ ID NO 86
<211> LENGTH: 20
<212> TYPE: DNA
<213> ORGANISM: Artificial
<220> FEATURE:
<223> OTHER INFORMATION: RT PCR Primer - Ncam1F

<400> SEQUENCE: 86
gtctgtcacc ctggtgtgtg                                              20

<210> SEQ ID NO 87
<211> LENGTH: 20
<212> TYPE: DNA
<213> ORGANISM: Artificial
<220> FEATURE:
<223> OTHER INFORMATION: RT PCR Primer - Ncam1R

<400> SEQUENCE: 87
gtggacgttc tccaggtgat                                              20

<210> SEQ ID NO 88
<211> LENGTH: 21
<212> TYPE: DNA
<213> ORGANISM: Artificial
<220> FEATURE:
<223> OTHER INFORMATION: RT PCR Primer - L19F

<400> SEQUENCE: 88
ctgaaggtca aagggaatgt g                                            21

<210> SEQ ID NO 89
<211> LENGTH: 21
<212> TYPE: DNA
<213> ORGANISM: Artificial
<220> FEATURE:
<223> OTHER INFORMATION: RT PCR Primer - L19R

<400> SEQUENCE: 89
ggacagagtc ttgatgatct c                                            21

<210> SEQ ID NO 90
<211> LENGTH: 211
<212> TYPE: DNA
<213> ORGANISM: Rattus norvegicus

<400> SEQUENCE: 90
ggcacataca gaggaaggta ggcaggcgag ggacccagca ggttcttgac agcttctccc    60 cgtgccccctc ccccactccc aggctggcat caagggcgga cagcgaaggc ctgcgggcgt  120

```
ggtggcaggc tggggctgac ctagggacag ccggactatg atggacactg tgccctgcaa      180
gtagtgagtg cctgcctcct ggaggtcctc a                                     211

<210> SEQ ID NO 91
<211> LENGTH: 401
<212> TYPE: DNA
<213> ORGANISM: Rattus norvegicus

<400> SEQUENCE: 91
tctaccaatt gggcaattga ttacctcaca tttcagcttt aactctaact catggcaagt      60
ggaatcatac ggctaggaaa actccaccag tcatccacag ctgcaaagaa ccacgcccaa     120
agccaaccaa agtggtaggg atccctgaca cacattttca aaagcttcta atttaaggtt     180
ttctatcatc gtctttcttg ggagtgaatt ctgcttctcc ctgttccatt cagctcctct     240
ctgctctcgt tcctctctgt cctctgtgct ctgtggagct ggacagacag agaagcctcc     300
tctctcccac ccacacagcc ccaacagcat caggccttgg catctgcatg agactgccat     360
cctgtcctat gcagtcaggc atgctagatg gtgtcaggag a                         401

<210> SEQ ID NO 92
<211> LENGTH: 348
<212> TYPE: DNA
<213> ORGANISM: Rattus norvegicus

<400> SEQUENCE: 92
gtgggtgtta gcaaagccct tagtaggact gcttagaaag aattaagtag ctagaagtag      60
agaggacaca gggcaaatct cagcaagcca tgcctcatca tcagaaagaa gacgcaacag     120
aaccagctgc tgagagccaa gcgaggtgtg agggacaggg caggttgggt gtgaccgaga     180
tgactgtggc atgatccttg ctgtgagcta aggaagagac tgatgatcac cacagagcta     240
gctcggcctg tcttcatgat catgggaagt caaatattct ttaaagcctc gttgacttca     300
gtggttcacc agcggctcca aatgaataca atccatttgc tttatggt                  348

<210> SEQ ID NO 93
<211> LENGTH: 232
<212> TYPE: DNA
<213> ORGANISM: Rattus norvegicus

<400> SEQUENCE: 93
gggttccact gcctcttcag gcagcccgcc gcctcaggag ccggggctct gggagctgct      60
ggaggagttc tcccggactc agtaccgtgc caaggacagc ggcgggaaga gcggctctaa     120
ggtgagcccc agaggtgcaa cgacctggaa ctggtccctg gcctgagtta ctgagggaag     180
actgtgatta gggatgggag gagagctgga aggagacctc cttgtaaagg ca             232

<210> SEQ ID NO 94
<211> LENGTH: 399
<212> TYPE: DNA
<213> ORGANISM: Rattus norvegicus

<400> SEQUENCE: 94
gccaagccag agggctcccc atgggggagg gggagggtgc aggagaaata gtaagggcag      60
ggtgctggct ctgcagttct tttcccactg agatatgtag ggacctgctc agtatctgga     120
cccagaactg gagagacctc tctactgggg cggggggggc atcttgtgct ttgcataaga     180 aaatgatgg ctaccccaag gagaatctcc tgcaccctga cccacatgct caaatgcccc      240
aggaggcaaa cagcatagca tacatgcagc cagggcccag acgaggttag acccagacgt     300
```

| | |
|---|---|
| ctgtggggat tcaaaagca ggcccacagg cccacgtgac aggaatgtag acggtggaga | 360 |
| ctgctccatg acaaatgttg gtggtcagtc tgaatccct | 399 |

<210> SEQ ID NO 95
<211> LENGTH: 163
<212> TYPE: DNA
<213> ORGANISM: Rattus norvegicus

<400> SEQUENCE: 95

| | |
|---|---|
| ctgagaggaa ggaaagagcc ttcaagaagc aaacaagttt cttagagggc gtctccattc | 60 |
| aactaagaac gcagtgagca aatgtgcaaa agtcctcagc tgttttggca gccgaagccg | 120 |
| gagtgtacaa ctccgtgggg ctcttcctga aagtgagga ata | 163 |

<210> SEQ ID NO 96
<211> LENGTH: 423
<212> TYPE: DNA
<213> ORGANISM: Rattus norvegicus

<400> SEQUENCE: 96

| | |
|---|---|
| tcattgtggg aattatgagg ccttcttaaa aatgtacaaa atcgtttgg tgcttctctt | 60 |
| tactttagtg ccagttgttg ctgccaagcg cggctggtcc atatgcccaa tgagtggtgc | 120 |
| tatatctgct taagtagcac aggtgtccag ggtttgatca acagtgtggc gatcaaccct | 180 |
| gtcatagagg ccctatgggt cactgtgaac ccagccctga gcaaggcctc tgagccggag | 240 |
| ttcaatgagg cacagaaatc tctggatttt gactgctcca gattactatg tcagaacaac | 300 |
| tggatttact ttgtgagaca ggcaggtgtt atttatttga aaaatatgat aacacaatat | 360 |
| tggtctgatc gggaagccac tccagggaac atctccccat atactatttc agaagaagac | 420 |
| tga | 423 |

<210> SEQ ID NO 97
<211> LENGTH: 383
<212> TYPE: DNA
<213> ORGANISM: Rattus norvegicus

<400> SEQUENCE: 97

| | |
|---|---|
| ggactttgag agagaaaagg agccacaacc cccccccag cagtgctggt gcacacacac | 60 |
| cctctcccgc gcgctcacac tcacatgcgc accatcgcac accccatccc atcctcgctc | 120 |
| ttcctgagat cctcgctctc tccctccccc tcttccttcc ctccctccct ggctccctct | 180 |
| ctcccttttg ctgcgtctgc cagcaacggt ctgcagccgg tcagaactcg tcctcttccc | 240 |
| cgagaatctg cgagctcccc ctcttcctct ggtcgggtgg agggagcagc tcgaagttta | 300 |
| cacccttgtg ccgctgccaa agccgaaagc ctttcttca gctgctgctt tttccctcct | 360 |
| ggttttgtt tttgtttttc cgg | 383 |

<210> SEQ ID NO 98
<211> LENGTH: 192
<212> TYPE: DNA
<213> ORGANISM: Rattus norvegicus

<400> SEQUENCE: 98

| | |
|---|---|
| gtgcaggtgg aagctattgt ctggctctcc tggtcagctc acgggtagtt gggtcccaga | 60 |
| tccaaatcca agagacctct gccaagccgg tgataggccc cagagcatgg cttagcggaa | 120 |
| agattgagag ctggtgacag gatcagtttg cgctgtcttt aggctgccct agaatggcct | 180 |
| ctgaccctga gg | 192 |

<210> SEQ ID NO 99
<211> LENGTH: 448
<212> TYPE: DNA
<213> ORGANISM: Rattus norvegicus

<400> SEQUENCE: 99

```
actggaggga aagccagcaa ccctgggatt tactacctct cattcctagt ggaatcgtgg      60
gcctttcaga ggcctgtggg agactagaca gctatatttt tagcttgtgg cttttccgta     120
ggacctgtta ccatgtccca tcaacctctg agctgcctga ctgagaaggg ggacagctcc     180
tgtgagaccc caggaaatgg accctccaat atggttcacc ccaacctgga cacattcact     240
cctgaggagc tgctgcagca aatgaaagaa ctcctggtcg agaaccacca gctgaaaggt     300
gagccggact gtccgtctgg actctccact caggaaacac aaacccttct gaagacggct     360
tgtcagtgag gtccattccc agcctctttc cctagaagga aaaacagcac agaaagactt     420
tgggcagggc taagggg ctt atttacat                                        448
```

<210> SEQ ID NO 100
<211> LENGTH: 334
<212> TYPE: DNA
<213> ORGANISM: Rattus norvegicus

<400> SEQUENCE: 100

```
tggggtgacc tcacctgcta gtaccacgga aaaagacaga agaaggagac cccgacttcc      60
tgggtcaggc ccagagccgc ccctagccgt agccatcttg cctctccgct gggcggaagc     120
ctcgggtccc ttccagtctc ttagcggtct ctctaggctt ccgctggcat cgtctctgtg     180
gcccagcgct ccccaaaccg gaagttcgtg tctgaggagc ttccgggagc gcgacctgg      240
ggtagctgac gtggagcctt tgggagtgca accgggagcg gcgggatccg ctaatctgac     300
ctgggagccg aaggcctgaa ggatgctaac caaa                                 334
```

<210> SEQ ID NO 101
<211> LENGTH: 316
<212> TYPE: DNA
<213> ORGANISM: Rattus norvegicus

<400> SEQUENCE: 101

```
ttgttggttg gaagtatgaa ttaggggatg ttagtaggct ttgaatcaca gctgccattc      60
gagccatccg gcacttcagg cctggaagag cattagagcc cagcaagtcc cttctctgct     120
ttagacgctg acagacattt tacccacaag ccttggctct gggtttgaag aagcagctat     180
ctgagaattc tgctcgccag gctccttcct gcctggcaaa tcgggaatgt gtctgaactg     240
gaaggagtgg gaccatcgga tggttctagg gttgtggtgt taatgctggg gacatggtgg     300
actcacaggc tgctgc                                                     316
```

<210> SEQ ID NO 102
<211> LENGTH: 164
<212> TYPE: DNA
<213> ORGANISM: Rattus norvegicus

<400> SEQUENCE: 102

```
ggttattgct tatgacctac tcttctcttc atttcctccg cagctctgag agcttatttc      60
gaaagaataa tggatgaacc atctccgttg gccaaaaccc tggagctgaa ccagcactcc     120
cgattcataa ttgggtccgt gtctgaagac aactcagaag atga                      164
```

<210> SEQ ID NO 103

<211> LENGTH: 207
<212> TYPE: DNA
<213> ORGANISM: Rattus norvegicus

<400> SEQUENCE: 103

```
tatttttatt tttgacaact gcctgcaagt acagaatgta cggtgatcac atccaccccc      60
attagcctcc cttttgcacta gtcccactct ctctttcccg cgccttttttt ccctctctct   120
cctttccgcg ccctttttttt taaacttacg catatttgaa tctcttaaag catttcgcgg    180
agtgcagggc ttaaattcag aaaatgc                                         207
```

<210> SEQ ID NO 104
<211> LENGTH: 261
<212> TYPE: DNA
<213> ORGANISM: Rattus norvegicus

<400> SEQUENCE: 104

```
gggccagaga ggctgtagga ggcagaccac cggcaagagc agagtgaagt agtgtgttct      60
ggacctagga gggctgctgt ggcttggtct cgtaatagct ggggttttct gaagaagatc    120
ggaacaagaa gatcaagccg gtcaacagtc tagcatggag cggggggtggg gttcgtgagc   180
cctcactcct aacagagcag ctatggaaag ttgacagctt ctgagggagg aagagtcagt    240
tttcttaag ggtgtggccc t                                               261
```

<210> SEQ ID NO 105
<211> LENGTH: 295
<212> TYPE: DNA
<213> ORGANISM: Rattus norvegicus

<400> SEQUENCE: 105

```
ggtctatgct cacagggacc ttctttcaga tgttgccaca ctgtctcttc gtgtccacca      60
ttcattctag tgcaggcgag ggccccaact ctgagcctgc tccatatgcc ccttttcaa     120
tttacagatt gccttggcgg ggggctggtt tagggtagtg ttttcttttg tttgggtcag    180
ggtcttactg tgaatccctg gcagtcccag aactcactat atagcaggct ggcccggatc    240
tcacagagcc cagcctgcct ctgctttcag agtgctgaga taaaaggcat gtgcc          295
```

<210> SEQ ID NO 106
<211> LENGTH: 325
<212> TYPE: DNA
<213> ORGANISM: Rattus norvegicus

<400> SEQUENCE: 106

```
gcagagcctg gggaaggatc cctagagaga tgctgatttg aaaccaaagc tgttgtcaga      60
ggttggctag ggctggataa ttgggtaatt catcaaagtt tgcttaaagt tgttgttaga    120
ggttggttag ggttggataa ttgggtaatt tattaaagtt tgttggctga ctcctctctt    180
ccatccgcat gtcctcggtg gctaacacat gctcaataaa tgttccacaa aggatgctcg    240
tgaacccatg ccgtcgacag ccacctcacc cttaaccaca caaggggaag actccagccg    300
tggccatgtc ctgtccctgc tttca                                          325
```

<210> SEQ ID NO 107
<211> LENGTH: 337
<212> TYPE: DNA
<213> ORGANISM: Rattus norvegicus

<400> SEQUENCE: 107

```
ttcagtacct cagagggtct caaacttcac taggagggca ggacacatgc atttctaggc      60
```

```
tggtccgtgg cggtctcaga caccgaaatc aacgagttcg gcatactatc ggcgaagaat    120
cctttgcgcg taaaaaccag gcctgccgcg tggcggcagt gaagtcgcgt acatcgcatc    180
cctgctgaaa cagattgcaa ctgagattga attttctcc ccattactct ctatgatccc     240
ataatcatgg gcttcatgag tcccggggtt catgatagtc cttgatagaa cttcctcaag    300
agctatctca gggatatggg gctctggggc catcagt                             337

<210> SEQ ID NO 108
<211> LENGTH: 236
<212> TYPE: DNA
<213> ORGANISM: Rattus norvegicus

<400> SEQUENCE: 108
aggagtggaa ggagcctggc aacacttggc tgcctggaat gccagccatc agtcagaggg     60
agaaaagcag cagcaatcac atgcttgcaa acacatacat gcacatagcc catacatatg    120
cgcggctcat tccggtctgc tgtgtagctc tctctctcta ccaagtcac cctcagatta    180 gtaatcagcc ccagccgaag cttcctggc ttcccaccag gctctgatta ggggt          236

<210> SEQ ID NO 109
<211> LENGTH: 296
<212> TYPE: DNA
<213> ORGANISM: Rattus norvegicus

<400> SEQUENCE: 109
cctccagtgt cttcagtgtc tctcccctga catcctcagt gccacctctc cctcaggccg     60
ctgtttgcag tccctctcct cctgccttcc tccagcctcc ctcacgcagg agactggact    120
agaagaccca ggctgatagg ggagcttccg gcggctgctt ctgtgattca tgctcccaca    180
gcctttcttc ttccctcgct ggctaagtgt gtgggtgtgc agcaggctct tcctagggaa    240
agctggcaaa aaataaaact tctcgagctc cgattcggta gacagattga gaggct         296

<210> SEQ ID NO 110
<211> LENGTH: 158
<212> TYPE: DNA
<213> ORGANISM: Rattus norvegicus

<400> SEQUENCE: 110
tgtgaggtca ggttctgtcc ctaacacggt gggaggggag agcttggggg ctttggcatc     60
acatcaccaa tcctagcttc caagactgac actgcagctg aaccgttgaa ctctgagttt    120
ccagatgctg tgctctcagc taccctacac ctgcgcgg                             158

<210> SEQ ID NO 111
<211> LENGTH: 326
<212> TYPE: DNA
<213> ORGANISM: Rattus norvegicus

<400> SEQUENCE: 111
ccctcaccct aacccgcgtg tctgcctctc tgaaggttta gctctccctc ccacgtgatt     60
tggctgcaga gaactgttta tccgttggt cccttcaagt tccggtggtg tctcagatgc    120
acggatttcc tgctcctgtg cccttatcca agggaactcc gaggccgtat acagtttcct    180
ctttggccag ggatgtgggc aggggtgggc agtgttggtg gtctcttccg ctctgcagcc    240
tcaggagtgc ccacctgtcc aggcgatgag gtctctttcc cacggggttt gggagcagcg    300
agctgctgag ggcagggatc cgcggg                                         326

<210> SEQ ID NO 112
```

```
<211> LENGTH: 296
<212> TYPE: DNA
<213> ORGANISM: Rattus norvegicus

<400> SEQUENCE: 112
aaaaacacat gtgtacaaaa gcaaaaacaa catagactat cctagccaca aagtctttgt      60
tcctataagg gatacgatag aatcccctga gggcggtgct acaatcaaag gtctagcact     120
aagtcctcta cctttctcta ttgggtcctc ggcagatcac tggactcatg aacactagtt     180
tcttgatcca caaagtaatt gggttgttat gcacgcgggt tggttttatt aacatggcaa     240
gctcaagtta ccctgagagg ggacctcatt cgaggaattg cctgaatcag actgat         296

<210> SEQ ID NO 113
<211> LENGTH: 260
<212> TYPE: DNA
<213> ORGANISM: Rattus norvegicus

<400> SEQUENCE: 113
aggcccaggt ccagagcttt gagctggccc acaccaacat ctacccatct ataagatgct      60
gctgcagtat atgaaggggc cggtcctgca gatccaaaac tgcaggatct ccatacacag     120
agcaacgaca gaatatctaa cagggttttg gtaatgatcc agggtagcag aagccagagt     180
tcttgaacca aaccaataaa tctttgaaat gaacactgca agtacagctg tttgggcaaa     240
agggtgtact gtggggcaca                                                 260

<210> SEQ ID NO 114
<211> LENGTH: 209
<212> TYPE: DNA
<213> ORGANISM: Rattus norvegicus

<400> SEQUENCE: 114
ttctcaggtg gtcagtgagg gcatgttgt gaccgtgggc tttgccacac tggacacact      60
catatggctt ttccccagtg tgagttctct gatgtacgac aaggtggaac ttttggctga     120
aagttatcgt gcattcgtga cattcatatg gtttctcccc agtatgagtt ctttgatgtt     180
caaggagccc ctgtttatgg ctgaggacc                                       209

<210> SEQ ID NO 115
<211> LENGTH: 211
<212> TYPE: DNA
<213> ORGANISM: Rattus norvegicus
<220> FEATURE:
<221> NAME/KEY: misc_feature
<222> LOCATION: (108)..(108)
<223> OTHER INFORMATION: n is a, c, g, or t
<220> FEATURE:
<221> NAME/KEY: misc_feature
<222> LOCATION: (167)..(167)
<223> OTHER INFORMATION: n is a, c, g, or t
<220> FEATURE:
<221> NAME/KEY: misc_feature
<222> LOCATION: (194)..(194)
<223> OTHER INFORMATION: n is a, c, g, or t
<220> FEATURE:
<221> NAME/KEY: misc_feature
<222> LOCATION: (206)..(206)
<223> OTHER INFORMATION: n is a, c, g, or t

<400> SEQUENCE: 115
ttagggtgag ggttaatcga attcccgcgg ccgccatggc ggccgggagc atgcgacgtc      60
gggcccaatt cgccctatag tgagtcgtat tacaattcac tggaagncc gcaccgaatc     120 gccccttcca aaaatttgcg ccaacctgaa tgggaaggac ccgcccntgt acgggcgcat     180
```

-continued

```
ttagcgcggc gggngtggtg gttacncgca a                          211
```

<210> SEQ ID NO 116
<211> LENGTH: 185
<212> TYPE: DNA
<213> ORGANISM: Rattus norvegicus

<400> SEQUENCE: 116

```
gcctgtgatc attgtctgga atttagggtg ttctgggtgc caagggtcca cgatctggct    60
cacgcggggt tagggtgtga acgccactct ggagaaagcc cacgcaccct gcagggccgt   120
ggctctgcgt gcactttttc tgtgtggggc cccgaggaat cggctaaatt aactgggttg   180
ctgtc                                                              185
```

METHODS FOR DIAGNOSING EPIGENETIC, TRANSGENERATIONAL EFFECTS OF ENVIRONMENTAL TOXICANTS ON MAMMALIAN GERM-LINES AND TREATING ASSOCIATED DISEASES

This application claims priority to provisional patent application, U.S. Ser. No. 60/683,134, filed May 20, 2005, the contents of which are hereby incorporated by reference in their entirety herein.

The work described here was supported, at least in part, by grants from USA Environmental Protection Agency (EPA) Grant No.: 99-NCERQA-D2 (#R827405-02-0). The United States government may, therefore, have certain rights in the invention.

Throughout this application various publications are referenced within parentheses. The disclosures of these publications in their entireties are hereby incorporated by reference into this application in order to more fully describe the state of the art to which this invention pertains.

FIELD OF INVENTION

The present invention relates to the epigenetic, transgenerational effects of environmental toxicants on the mammalian germ line, and more specifically to the diagnosis of the effects of endocrine disruptors on germ lines, and treatment of associated diseases.

BACKGROUND OF THE INVENTION

Embryonic or early postnatal exposure to environmental compounds such as endocrine disruptors have been shown to promote abnormal development and disease in a variety of species, including humans [135, 136, 137, 138]. Although a large number of environmental factors, such as smoking and caloric restriction [139, 140], and synthetic compounds ranging from plastics to pesticides [141, 142], can promote adult onset disease and abnormalities, the mechanisms of action of these factors are largely unknown.

"Genetic imprinting", suggests that some genes "remember" the sex of the parent they came from and that this "parental memory" regulates their activity. This regulation can take different forms, but usually one allele is silenced so that only one parental copy is active. For some imprinted genes only the paternal allele is active, while for other imprinted genes only the maternal allele is active. This differential gene activity dependent on the sex of the parent that transmitted the copy of the gene is called "genetic imprinting." In order for genetic imprinting to occur, some kind of molecular mark must exist to distinguish a maternal allele from a paternal allele. This molecular marker is "epigenetic," meaning that it does not directly modify the DNA nucleotide sequence but causes a heritable change of gene activity. Epigenetic modifications act like the "font" of the primary basesequence "text," strongly affecting the genetic message.

A number of human diseases are the result of abnormal epigenetic (i.e. DNA methylation) programming including Angelman's syndrome, Beckwin-Wiedemann syndrome and Prader-Willi syndrome [143, 144, 145]. Alterations in the DNA methylation patterns of imprinted genes have also been shown to promote the development of disease [146]. Potential epigenetic abnormalities in children from in vitro fertilization (i.e. intracytoplasmic sperm injection) have been identified [147]. A study of monozygotic twins suggested environmental epigenetic effects on disease [148]. Therefore, numerous studies and clinical conditions suggest epigenetics may be a critical factor in disease etiology.

Transgenerational effects of irradiation, chemical treatments (e.g. chemotherapy) and environmental toxicants such as endocrine disruptors have been observed over the past decade. The majority of transgenerational observations are simply the effects of the agent on the gestating mother and subsequent actions on the offspring associated with the F1 generation [1-3]. Transgenerational effects for multiple generations have not been as thoroughly studied and require transmission through the germ-line. The ability of an external agent to induce a transgenerational effect may be through an epigenetic phenomenon involving DNA methylation or stable chromosomal alterations [4-7]. Transgenerational effects of irradiation were the first to be identified and some have been shown to be transmitted through the germ-line to multiple generations [4-6]. These are often associated with mutagenesis and tumor formations in subsequent generations. The treatment of cancers with chemotherapeutics also has been shown to cause transgenerational effects [8-10], but the impact on multiple generations has not been thoroughly investigated. Recently, nutritional effects on the F1 generation have been observed [11], but none have been shown to be transgenerational. Environmental toxicants such as endocrine disruptors have also been shown to influence the F1 generation after parental exposure [9, 12-14], but few studies have demonstrated transgenerational effects on multiple generations. However, the potential impact of such transgenerational effects of endocrine disruptors has been discussed [15].

Epigenetic alterations that lead to transgenerational transmission of specific genetic traits or molecular events (e.g. imprinting) have recently been identified [16-19]. These observations have lead to the conclusion that a re-programming through altered methylation state of the germ-line is responsible. The impact this has on human health and evolutionary importance is significant [16, 17]. Recent investigations of the methylation state of the primordial germ cells (PGC) has indicated that as PGC migrate down the genital ridge a de-methylation (i.e. erasure of methylation) starts, and upon colonization in the early gonad a complete de-methylation is achieved [20-22]. This has been primarily observed through the analysis of specific imprinted genes [23]. During the period of sex determination in the gonad the germ cells undergo a re-methylation involving a sex specific determination of the germ cells. Although the de-methylation may not require the gonad somatic cells [21], the re-methylation of the germ-line appears to be dependent on association with the somatic cells in the gonads [20, 22].

Many reports have suggested that environmental endocrine disruptors, which act to mimic estrogens or act as anti-estrogens or anti-androgens, are detrimental to reproduction, and may be the factors responsible for abnormalities, such as a decrease in sperm count, an increase in testicular cancer [24, 25], and an increase in abnormalities in sex determination in many species [26]. Examples of the environmental endocrine disruptors that have been targeted for adverse effects on reproductive systems in humans and other animals are pesticides (e.g. methoxychlor), fungicides (e.g. vinclozolin), a range of xenoestrogens and certain phthalates. Most of these chemicals are ubiquitous in the environment and both humans and other animals are exposed to them daily. Many of these compounds and endocrine disruptors can be metabolized into both estrogenic and anti-androgenic activities [27]. In the current study, methoxychlor and vinclozolin are used as model endocrine disruptors [28] and has both estrogenic and anti-androgenic metabolites [27].

Many environmental endocrine disruptors are weakly estrogenic and elicit their actions through the estrogen receptors. The two mammalian receptors for estrogen (ER-α and ER-β) are widely distributed throughout the reproductive tract and during fetal gonad development [29, 30]. ER-β is present in higher concentrations within the fetal testis and ovary while ER-α is present mainly within the uterus [31, 32]. During fetal testis development ER-β is first expressed in Sertoli and myoid cells after seminiferous cord formation [33]. In rats ER-β has also been localized to pre-spermatogonia, which may explain the proliferative actions of estrogen on early postnatal gonocyte cultures [34]. The importance of ER-α was further delineated when knockout mice [35] and human males [36] lacking expression of this gene were found to be sterile. Fetal development of the testis in these experiments was not altered. Early embryonic testis morphology in a double knockout remains to be examined [37]. Neonatal exposure to estrogen alters the ERα and ER-β expression during postnatal testis and hypothalamic/pituitary development [38, 39]. Interestingly, the neonatal exposure to the estrogenic compound diethylstilbestrol promotes abnormal testis and male reproductive tract development. Therefore, actions of estrogenic endocrine disruptors on estrogen receptors may impair normal fetal gonadal development or stimulate inappropriate differentiation of cells leading to infertility. Although the estrogen receptors are thought to have a role in testis development [40-42], the specific functions remain to be elucidated. Treatment of males with estrogens during early fetal life may alter responsiveness to androgens by changing androgen receptor (AR) expression patterns [43, 44].

Anti-androgenic endocrine disruptors can also influence fetal gonad development. AR expression is very similar to ER-β expression in the developing testis [32, 45]. However, AR is stage dependent while ER-β expression appears to be more constitutively expressed [32]. AR is detected in Sertoli, myoid, and pre-spermatogonial cells just after cord formation [46]. AR also can be detected in interstitial cells late in development. It is proposed that AR is present in cells that migrate from the mesonephros and enables cord formation to occur [46]. Therefore, inappropriate expression or actions of AR through treatment by endocrine disruptors may effect the process of morphological sex differentiation (cord formation). Anti-androgens such as flutamide [47] or cyproterone acetate (CPA) [48] administered to pregnant rats at different ages of gestation impair fertility in male offspring. Both flutamide and CPA block the ability of androgens and epidermal growth factor (EGF) to stabilize the Wolffian duct [49]. Testosterone has been demonstrated to increase the expression of EGF receptor in the developing testis [49]. Therefore, perturbation of AR may also cause inappropriate expression and action of growth factors in the testis. A commonly used anti-androgenic endocrine disrupter is vinclozolin, which is used as a fungicide in the wine industry [50, 51]. Vinclozolin has been shown to act as an environmental anti-androgen and influence gonad development and fertility.

Methoxychlor is a chlorinated hydrocarbon pesticide currently used in the United States as a replacement for DDT [52]. Methoxychlor can be metabolized by the liver into two demethylated compounds (i.e. mono-OH-M and bis-OH-M). The most active estrogenic metabolite is 2,2-bis-(p-hydroxyphenyl)-1,1,1-trichloroethane, (HPTE) [28, 53, 54]. Other methoxychlor metabolites appear to have anti-androgenic activity [27]. HPTE is weakly estrogenic [55-57] and stimulates the expression of estrogen receptors [58]. Recently it has been found that the estrogenic metabolite of methoxychlor HPTE has differential effects on ER-α and ER-β being an ER-α agonist and ER-β antagonist [59, 60]. Other methoxychlor metabolites also have differential effects on ER-α and ER-β [60]. Therefore in examining the actions of methoxychlor or HPTE the ER agonist and antagonist activity needs to be considered, as well as, anti-androgenic activities. Consideration of these differential activities is critical in elucidating the mechanisms of action of endocrine disruptors such as methoxychlor. Previously, methoxychlor metabolites have been shown to act differentially on the ER from different species [61]. The effects of methoxychlor at an embryonic or early postnatal period can influence reproductive functions at later adult periods [62-64]. Neonatal exposure to methoxychlor can influence pregnancy [65, 66], ovarian and hypothalamic function [67, 68], reproductive behavior [69], prostate development [70], thymus development [71], and testis development [72]. Therefore, transient embryonic exposure to an endocrine disruptor can reprogram and/or imprint effects that manifest in the adult on reproductive physiology. A study has shown that effects on a gestating mother may influence subsequent pregnancies as well [73].

Vinclozolin is an anti-androgenic compound that is metabolized into butenoic acid and enanilide derivatives termed M1 and M2, respectively [74]. The affinity of the metabolites for the androgen receptor are 10-15 times (i.e. Ki 10-100 µM) greater than the parent compound [75]. Exposure of neonates to anti-androgenic compounds causes abnormalities in sexual differentiation and gonad formation [75, 76]. Peripubertal exposure to anti-androgens delays puberty, inhibits development of androgen-dependent tissues, and alters androgen receptor function in the male rat [77-79]. Embryonic and early postnatal exposure can influence subsequent male sexual differentiation and fertility [80-83]. The embryonic exposure periods at the time of testis formation appears to be the most sensitive exposure period to the anti-androgens [84]. Evidence with a variety of toxic compounds has determined that metabolites of estrogenic substances such as p,p'DDE (metabolite of DDT) act as anti-androgens and inhibit the transcription of androgen regulated genes [85]. A recent report suggests antagonistic and synergistic interaction effects between vinclozolin and androgens [86].

Thus, the impact of toxic compounds has become more complicated, and their estrogenic and anti-androgenic effects on reproduction and gonadal development need to be investigated.

The adult testis is a complex organ that is composed of seminiferous tubules, which are enclosed by a surrounding interstitium. The seminiferous tubules are the site of spermatogenesis where germ cells develop into spermatozoa in close interaction with Sertoli cells. The Sertoli cells [87] form the seminiferous tubule and provide the cytoarchitectural arrangements for the developing germinal cells [88]. Tight junctional complexes between the Sertoli cells contribute to the maintenance of a blood-testis barrier [89] and create a unique environment within the tubule [90, 91]. The majority of Sertoli secretory products [92-97] are hormonally regulated and provides useful markers of Sertoli cell differentiation. Surrounding the Sertoli cells are a layer of peritubular myoid cells which function in contraction of the tubule. The peritubular cell surrounds and forms the exterior wall of the seminiferous tubule. Peritubular cells are mesenchymally derived cells that secrete fibronectin [98] and several extracellular matrix components [99]. Both the peritubular and the Sertoli cells form the basement membrane surrounding the seminiferous tubule and their interactions are important in germ cell development. The interstitial space around the seminiferous tubules contains another somatic cell type, the Leydig cell that is responsible for testosterone production. Leydig cells have a major influence on spermatogenesis through the actions of testosterone on both the seminiferous tubule and the pituitary. Although, the Leydig cell has numerous secretory products [100], the ability of the cell to produce androgen to act on the seminiferous tubules is the most significant secretory product of the cells. Leydig cell androgen production can be directly influenced by the actions of the endocrine disruptor methoxychlor and its metabolite HPTE [101]. Thus, interaction of all three somatic cells, Sertoli, peritubular and Leydig, are important for regulation of normal spermatogenic function in the testis [100]. The process of fetal testis formation occurs late in embryonic development (embryonic day 13 (E13) in the rat) and is initiated by migration of primordial germ cells, first from the yolk sac to the hindgut and then from the hindgut to the genital ridge. The gonad is bipotential after germ cells migration and morphologically can be distinguished from the adjoining mesonephros (E12 in rat), but cannot be identified as an ovary or a testis. Two events occur early on embryonic day 13 (E13) to alter the bipotential gonad. First, Sertoli cells, which are proposed to be the first cell in the testis that differentiates, aggregate around primordial germ cells [102, 103]. Secondly, migration of mesenchymal cells occurs from the adjoining mesonephros into the developing gonad to surround the Sertoli cell-germinal cell aggregates. The migrating population of cells is speculated to be pre-peritubular cells [104, 105]. The mechanism for this migration is due to a chemotactic signal from the testis to promote cell migration [106]. Therefore, during early testis development Sertoli-peritubular cell interactions promote cord formation to occur. The cords neonatally develop into seminiferous cords and at the onset of puberty develop into the seminiferous tubules. Seminiferous cords form as the Sertoli cell-primordial germ cell aggregates become more organized and are fully surrounded by the migrated mesonephros mesenchymal cells (i.e. pre-peritubular cells). The formation of the seminiferous cords (E14 in rat) is a critical event in the morphogenesis of the testis since this is the first indication of male sex differentiation. During the process of cord formation, the Sertoli cells undergo a number of morphological changes including: a change in expression of mesenchymal to epithelial cell markers (vimentin to cytokeratin), [107] a change in expression of cytokeratin 19 to cytokeratin 18 (cytokeratin 19 is expressed in ovary) [108], and expression of MIS which inhibits the development of the Müllerian duct, the precursor of the female uterus, cervix, fallopian tubes and upper vagina [109, 110]. Outside of the seminiferous cords the peritubular layer of cells become identifiable from the interstitium or Leydig cells at E15 [111] and 3βPHSD production is detected after E15 [112]. This is important since the production of testosterone and androgens by the Leydig cells has been demonstrated to stabilize the Wolffian duct derivatives for normal male duct development [113]. Therefore, appropriate differentiation of somatic cell types in the testis around the time of cord formation is crucial not only for the normal development of the testis, but also for the continued presence of the Wolffian duct.

Primordial germ cells form aggregates with Sertoli cells prior to cord formation [102, 103] and then are localized within the seminiferous cords as testis morphogenesis is initiated. The germ cells undergo a rapid mitosis until the late stages of embryonic development at which time they become quiescent. After birth in the rodent germ cell mitosis resumes and during the onset of puberty and formation of the seminiferous tubules spermatogenesis is initiated. Germ cells throughout development are in close association with the somatic cells (i.e. Sertoli cells). Alteration of somatic cell differentiation could indirectly effect germ cell development, as well as having direct effects on the germ cells.

The testis transcriptome (i.e. global gene expression profile) will change during testis development, due to the differentiation and growth of a variety of different cell types. These changes in the testis transcriptome reflect critical regulatory genes and gene families required to promote normal testis function and development. A variety of functionally related genes such as transcription factors, signal transduction genes, cell cycle genes, cell survival genes, and growth factors will be involved in testis development and part of the transcriptome. The ability of the endocrine disrupter to alter the testis transcriptome and specific genes and gene families is in part one of the mechanisms used to alter fetal and adult testis function and development. Examples of gene families shown to influence embryonic testis development include the epidermal growth factor (EGF) family [114-116], the transforming growth factor β (TGFβ) family [117] and neurotropin growth factor family [118, 119].

Previously it was demonstrated that a transient exposure to methoxychlor or vinclozolin of a gestating mother between embryonic days 8 to 15 (E8-E15) promoted in the adult F1 generation, reduced spermatogenic capacity, increased spermatogenic cell apoptosis and decreased sperm number and motility [120, 121]. The gestating mother rats were injected daily with an intraperitoneal injection of 100 or 200 mg/kg dose of the endocrine disruptor. These doses are similar to previous in vivo studies, and are within anticipated environmental exposure levels [27, 28, 52-72, 74-82, 84, 85, 121-123]. A similar transient exposure between embryonic days 15-20 (E15-E20), had no effect on the F1 generation testis [120, 121].

A number of human diseases are the result of abnormal epigenetic (i.e. DNA methylation) programming including Angelman's syndrome, Beckwin-Wiedemann syndrome and Prader-Willi syndrome [143-145]. Alterations in the DNA methylation patterns of imprinted genes have also been shown to promote the development of disease [146]. Potential epigenetic abnormalities in children from in vitro fertilization (i.e. intracytoplasmic sperm injection) have been identified [147]. A study of monozygotic twins suggested environmental epigenetic effects on disease [148]. Therefore, numerous studies and clinical conditions suggest epigenetics may be a critical factor in disease etiology.

The observation that an environmental toxicant (e.g. endocrine disruptor) can have an epigenetic effect on the germ-line of the gestating mother, and cause a transgenerational affect on male reproduction, significantly impacts our understanding of the hazards of these compounds to human health, as well as all other mammalian species. Elucidation of this phenomenon permits better understanding of the true hazards of environmental toxicants, permits identification of the specific causal agents, and allows the development of appropriate preventative and therapeutic approaches. Independent of the specific compound or agent of interest, the establishment of this potential mechanism of action is critical, and provides insight into the effects of environmental factors that influence embryonic mammalian development and adult reproduction.

SUMMARY OF THE INVENTION

The present invention is based on the discovery that environmental toxicants, such as endocrine disruptors, cause epigenetic, transgenerational effects on mammalian germlines in male progeny of an exposed female parental subject. These effects are associated with various diseases.

The invention provides methods to induce epigenetic, transgenerational alterations in the germline DNA of male neonatal progeny subjects, by exposing the gestating female parental subject to at least one endocrine disrupter agent. The female parental animal gives birth to a male progeny with the epigenetic, transgenerational alteration in its germline DNA.

The alteration involves the permanent reprogramming of the germline DNA through methylation of DNA. The alteration may be associated with a disease or dysfunction in the progeny subject. The disease or dysfunction can be pre-eclampsia in a female progeny subject, prostate disease in the male progeny subject, male infertility, immune cell activation, premature aging or cancer. The male progeny subject may have reduced fertility or sterility associated with abnormal testicular development, abnormal spermatogenesis, decreased sperm mobility or decreased forward sperm movement.

The invention includes methods of detecting an epigenetic, transgenerational alteration in the germline DNA of a male progeny subject exposed to an endocrine disruptor, by identifying abnormal methylated DNA in the germline of the male progeny subject.

Additional methods of the invention include a method to diagnose disease or dysfunction or the propensity to develop disease or dysfunction, resulting from contact of the germline DNA of a male progeny subject with an endocrine disruptor agent during gestation of the parental subject, by identifying a profile of methylated DNA in the male progeny subject and comparing to a profile previously associated with disease or dysfunction, such that the presence of a substantially similar methylated DNA profile in the progeny subject indicates the presence of disease or dysfunction, or indicates the propensity of the subject to develop that disease or dysfunction.

Further methods of the invention include methods of preventing disease or dysfunction associated with abnormal DNA methylation profiles in the germline of a subject, by identifying normal DNA methylation profiles in germlines of male subjects, and then detecting altered DNA methylation sites associated with disease or dysfunction in the germline of a male pubertal or adult subject, and modifying the altered DNA to restore the normal methylation profile, in order to prevent disease or dysfunction. In addition, genes containing altered methylated DNA sites associated with disease or dysfunction, in the germline of a male subject, can be used as diagnostic agents, to detect the likelihood the male will develop disease or dysfunction associated with the altered methylated DNA. In addition, therapeutic agents can be designed to inhibit the gene product or alter the expression of the gene, to treat the associated disease or dysfunction.

Another method of the invention is to determine whether a test agent induces an epigenetic, transgenerational reduction in male fertility, or sterility, using a testicular organ culture contacted with a test agent, under conditions suitable to inhibit cord formation in the testicular organ culture and detecting whether cord formation is inhibited. In addition, the methods include further determining whether a test agent inhibits the epigenetic, transgenerational reduction in male fertility or sterility caused by an endocrine disruptor agent, by using a testicular organ culture that has been contacted with a first endocrine disruptor agent that induces a reduction in male fertility or sterility, and then treated with another test agent that is proposed as an inhibitor of the activity of the first agent, and determining whether cord formation or DNA methylation or gene expression in the testicular organ culture is still altered.

The methods of the invention include identifying methylation defects in the progeny of the male subject exposed to an endocrine disruptor agent, by preparing DNA (i.e. sperm or testis) from the subject, and observing whether methylation is abnormal, or gene expression (levels of genes being expressed-microarray) is altered.

BRIEF DESCRIPTION OF THE FIGURES

FIG. 1 depicts the transgenerational phenotype after vinclozolin treatment of F0 gestating mothers, as described in Example 1, infra. (A) spermatogenic cell apoptosis, (B) epididymal sperm counts and (C) epididymal sperm motility in P60-180 control and vinclozolin Sprague-Dawley rats in the F1, F2, F3 and F4 generations, and F2 vinclozolin generation male outcross (VOC) to wild-type control females, and F2 vinclozolin generation female reverse outcross (RVOC) to wild-type control males. Statistically significantly differences between control and vinclozolin generation animals are indicated by (*) for $P<0.05$. The "n" value for each bar ranged between 10-30 for F1-F4, VOC and RVOC.

FIG. 2 shows the results of testis histology from a 100-day-old control (A) and vinclozolin (B) F3 generation animals, 200× magnification, as described in Example 1, infra. The F3 vinclozolin generation male, is a representative infertile male identified by the lack of spermatogenic cells in the tubule.

FIG. 4 shows the transgenerational phenotype after methoxychlor treatment. (A) spermatogenic cell apoptosis, (B) epididymal sperm counts and (C) epididymal sperm motility in P60-120 control and treated Fisher rats in F1 and F2 generations. Statistically significant differences between control and treated animals within a generation are indicated by (*) for $P<0.05$. The number of animals for each bar ranged between 6 to 12.

FIG. 6 shows the DNA sequence from the lysophospholipase (LPL) gene with altered methylation pattern (SEQ ID NO:90). The LPL genomic sequence (GENBANK accession No. NW_047762.1) from base pairs 32270685 to 32270889. Methylated cytosine residues (Bold CG) present in both control and vinclozolin generation animal sperm are marked with a closed circle (•), and those altered in vinclozolin F1-F4 generation sperm samples are marked with an open circle (°).

FIGS. 10A-10Q shows methylation status of the candidates with bisulfite sequencing. Each analysis provides the DNA sequence of interest, the physical chromosome map with alignment (arrow) and bisulfite sequence results (SEQ ID NOs:91-107). The potential methylated cytosine residues are marked with an underline and the asterisks denote the altered methylated CpG sites. The bisulfite sequencing is presented as a series of circles representing the CpG sites underlined with an open circle denoting non-methylation and closed circle methylation. Each series of circles represents individual cloned DNA sequences analyzed. The CpG with statistically significant altered methylation in the vinclozolin generation sperm DNA is marked with an asterisk (*).

FIGS. 11A-11I show methylation of candidates with bisulfite sequencing with the physical chromosome map with alignment (arrow), DNA sequence of interest, and bisulfite results presented, as described in Example II, infra (SEQ ID NOs:108-116).

FIG. 13 shows a summary of altered methylation changes by bisulfite sequencing analysis for each confirmed candidate, as described in Example II, infra. (Shaded box are statistically ($p<0.05$) different changes with all methylation percentages for each site presented.)

FIG. 15 shows (A) Microarray gene expression analysis of embryonic day 13, 14 and 16 (E13, E14, E16) testis from control and vinclozolin F1 and F2 generations and wildtype (Wt) controls. Relative hybridization signal, mean±SEM is presented. (B) shows that adult brain gene expression for NCAM1 in control and vinclozolin F3 generation individual animals using a semi-quantitative PCR as compared to a constitutively expressed gene L19. The PCR analysis presents the 351 bp NCAM1 product and 195 bp L19 with each lane representing a different animal. (C) The quantitation of relative brain expression levels of NCAM1 for the control and vinclozolin data, mean±SEM.

DETAILED DESCRIPTION OF THE INVENTION

Figure 3:
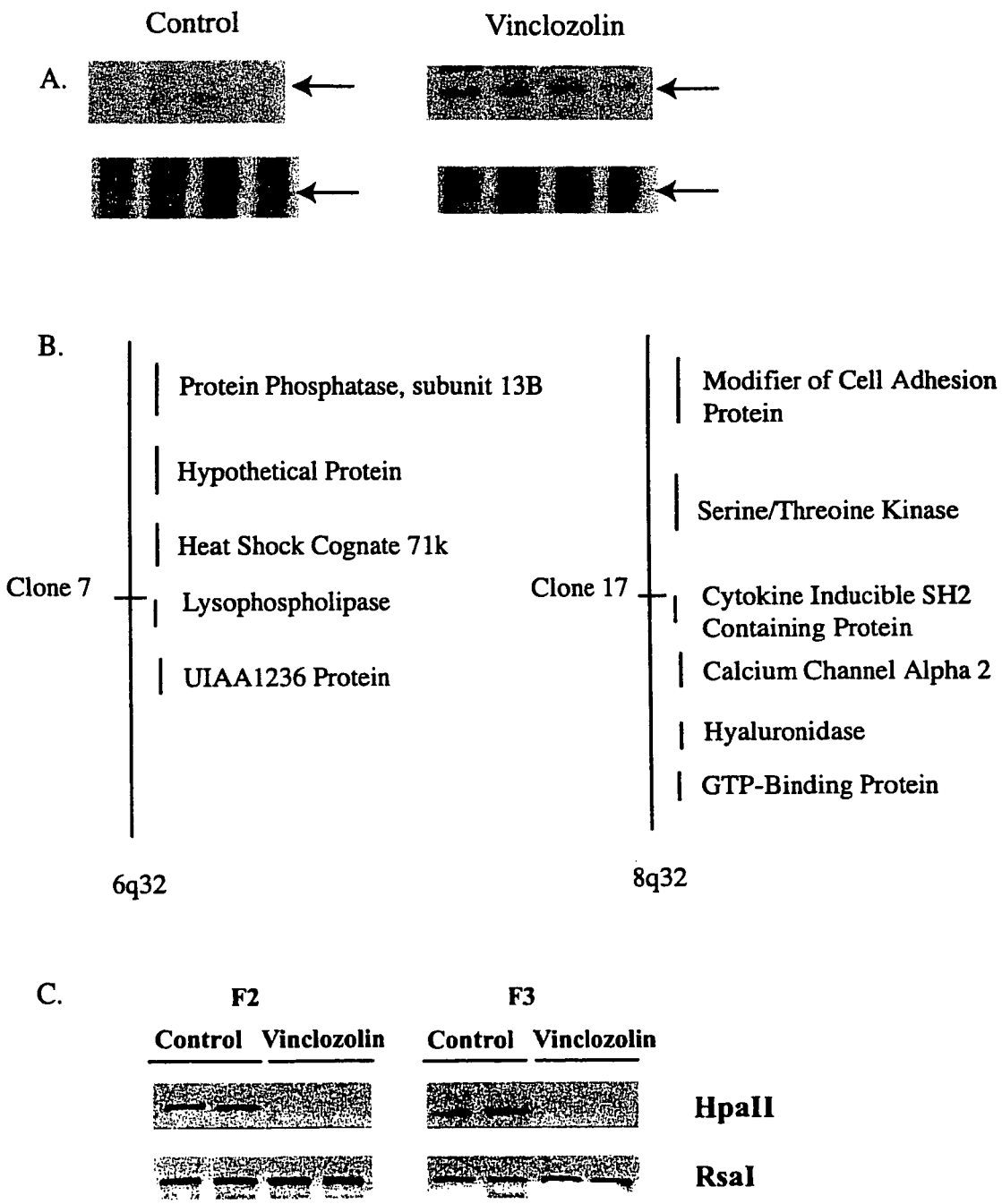
FIG. 3 shows the result of DNA methylation analysis from control and vinclozolin testis, as described in Example 1, infra. (A) Representative gel images of the PCR based methylation sensitive HpaII (H) restriction enzyme digest analysis with representative band (arrow) affected in postnatal day 6 (P6) testis from control (control) and vinclozolin (vinclozolin) treatment animals. Each lane represents a different individual animal (n=4). (B) Location of selected sequences on specific chromosomes for two representative DNA sequences termed clone 7 & 17 with altered DNA methylation patterns. (C) Methylation sensitive restriction enzyme PCR analysis of the methylation state of the clone 17, cytokine-inducible SH2 STAT-like protein gene in epididymal sperm, from F2 and F3 generations from control and vinclozolin treated animals. The bands presented are representative of sperm DNA collected from different animals, from different litters, and are consistent in 4 out of 8 F2 animals, and 2 out of 5 F3 animals, analyzed.

The present invention discloses the discovery that specific environmental toxicants, such as endocrine disruptors, after a transient embryonic exposure at the critical time of sex determination, can cause transgenerational epigenetic effects directly linked to primordial germ cell re-methylation. The epigenetic effect re-programs the germ-line through DNA methylation events, that likely involve, in part, imprinted genes. The ability of an environmental toxicant to act at this critical stage of development, and permanently re-program the germ-line to cause transgenerational effects, has not been previously appreciated. The impact this has on our understanding of the hazards of such compounds is significant. In addition to reproduction defects, such as male infertility, other clinical abnormalities and disease states such as prostate abnormalities, tumor development, abnormal immune system activation and premature aging, can be induced. Applications include novel methods for investigating these conditions, or for treatment and diagnosis of associated diseases.

All scientific and technical terms used in this application have meanings commonly used in the art unless otherwise specified. As used in this application, the following words or phrases have the meanings specified.

"Transgenerational," is defined as germ-line transmission of an abnormal disease phenotype for F1 to F2 to F3 to etc. generations, not simply involving the F1 generation of an F0 exposed pregnant female.

"Epigenetic," is defined as modified DNA state (i.e. DNA methylation), that does not involve an altered nucleotide sequence.

"Imprinted-like genes," are defined as genes with altered or abnormal DNA methylation sites (i.e. anywhere in the gene at CpG sites), where the altered methylation state, is transgenerational and passed through the germ-line.

METHODS OF THE INVENTION

The methods of the invention can be used to detect the impact of environmental toxicants, such as endocrine disruptors, on the mammalian genome and to develop diagnostic, preventative and therapeutic treatments.

The examples, infra, provide direct evidence that environmental factors can influence the epigenetic, DNA methylation programming, of the germ line in a subject, by inducing the presence of new imprinted genes or DNA sequences. The ability to associate these changes in DNA sequence methylation with diseases, suggests these specific genes and DNA sequence methylation patterns can provide diagnostic markers for disease, which can be used even before a disease develops.

For example, once specific genes, or DNA sequences, are identified as being influenced by the endocrine disruptors (i.e. have altered or abnormal methylation state) they can be used in a genomic based microarray approach or a methylation sensitive restriction enzyme digest procedure to determine risk assessment, and document previous endocrine disruptor exposure of the mammalian subject's predecessor's to the toxicants. For the affected genes identified, the expression levels of mRNA corresponding to the genes, can also be assessed, through a traditional expression microarray procedure. A microarray procedure can be used to assess methylation differences through bisulfite conversion sensitivity [124-126].

In one embodiment, the presence of an altered epigenetic diagnostic DNA methylation change in an individual's DNA, is detected with procedures such as 1) methylation restriction enzyme digest and PCR analysis for specific genes; or 2) microarray analysis with and without bisulfite treated DNA to assess changes in methylation of a group or large number of genes; or 3) direct bisulfite sequencing of DNA sequences of interest. Altered DNA sequence methylation is detected providing a diagnostic for a specific disease state, even prior to the development of the disease. This information in turn allows preventative therapeutics to be developed for therapies to prevent the disease, in addition to therapeutics to treat disease, after it develops. For example, if several DNA sequences are found to have a difference in methylation after toxicant exposure, a DNA sample is collected, and then analyzed for epigenetic changes (i.e. DNA methylation), and, if identified, a diagnosis of toxicant exposure is made, with the susceptibility to acquire a disease state at a later time. Different tissues are expected to have different epigenetic markers, and different toxicants may induce different epigenetic markers.

The microassay is used to assess toxic exposure risk assessment in a subject, and the potential of the subject to develop a disease, such as infertility. The bisulfite converts cytosine (C) residues to thymine (T) residues and if cytosines are methylated, can not convert the residue. The microarray to assess methylated changes involves arrays of oligonucleotides with various sequences having C and T conversions, to assess alterations in methylation. DNA is isolated and incubated in the absence or presence of bisulfite. and then polymerase chain reaction (PCR) amplified. The sample is then exposed to the microarray, and methylation states determined by corresponding microarray hybridization. Alternatively, a multiplex PCR with different sets of primers can be used, followed by methylation sensitive restriction enzyme digestion and analysis.

After identifying an abnormal methylation state, appropriate preventative or therapeutic procedures are instituted. For example, if a subject was expected to have lowered fertility or prostate disease a hormone treatment to elevate testis or prostate function to prevent onset of sub-fertility or disease can be used.

An embodiment of the invention is a method to induce an epigenetic, transgenerational alteration in the germline DNA of male neonatal progeny, comprising administering to a gestating female parental subject, at least one endocrine disruptor agent wherein said female parental subject gives birth to a male progeny subject, which has the epigenetic, transgenerational alteration, in its germline DNA. The epigenetic, transgenerational alteration is methylation of DNA in the germline DNA of the male progeny. The alteration in the germline DNA of male progeny is associated with a disease and/or dysfunction. Male progeny of the femal parental subject have an epigenetic, transgenerational alteration, in their germ line DNA, and are of the F1, F2, F3 or F4 generation.

The epigenetic, transgenerational alteration in the germ line DNA of the male progeny results in reduced fertility or sterility of the male progeny associated with abnormal testicular development, abnormal spermatogenesis, decreased sperm mobility and/or decreased forward sperm movement.

In another embodiment of the invention, a method of detecting an epigenetic, transgenerational alteration, in the germ-line DNA of a male progeny subject from a female parental subject administered at least one endocrine disruptor, comprises identifying methylated DNA in the germ line of the male progeny subject. The method can use a microarray assay, a methylation sensitive restriction enzyme digest analysis followed by PCR, to identify alterations in DNA methylation.

The method disease or dysfunction is selected from, but not limited to, pre-eclampsia, prostate disease, male infertility, immune cell activation and cancer.

The invention also includes an embodiment that is a method for identifying a disease and/or dysfunction in a male progeny subject, or identifying the propensity of the subject to develop that disease and/or dysfunction, where the disease and/or dysfunction is associated with epigenetic, transgenerational DNA alterations resulting from contact of the germline DNA of the progeny male subject during gestation, with at least one endocrine disrupter agent, the method comprising identifying a profile of methylated DNA in the male progeny subject, where the profile is previously associated with a disease and/or dysfunction, whereby the presence of a substantially similar methylated DNA profile, indicates the presence of disease and/or dysfunction, or indicates the propensity of the subject to develop that disease and/or dysfunction.

The invention further is a method for preventing or delaying the onset of a disease and/or dysfunction in the germ-line DNA of an affected transgenerational subject, where the disease and/or dysfunction is associated with epigenetic, transgenerational DNA alterations resulting from contact of the germline DNA of an affected transgenerational subject carrying the epigenetic alteration, during gestation of the female parental subject, with at least one disruptor agent, comprising 1) identifying the presence of an altered methylated DNA profile associated with a disease and/or dysfunction in a subject; and 2) modifying the methylation state of the subjects' germline DNA, such that the disease and/or dysfunction is prevented or delayed in the subject. The transgenerational genes with altered methylated DNA can be identified using a methylation sensitive restriction enzyme analysis, followed by PCR.

The invention also includes a method of determining whether a first test agent induces epigenetic, transgenerational reduction in male fertility, or sterility, by contacting a testicular organ culture with the first test agent, under conditions suitable to alter cord formation in the testicular organ culture, and detecting any abnormal cord formation. In addition, a second test agent may be evaluated to determine whether it inhibits epigenetic, transgenerational reduction in male fertility or sterility, by contacting an animal testicular organ culture with the second test agent, after first contacting the organ culture with the first test agent that induces epigenetic, transgenerational reduction in male fertility, or sterility, and determining whether the actions of the first agent are reversed, or prevented in the testicular organ culture, after administration of the second test agent.

In an additional embodiment, a method of identifying methylation defects in the progeny of a male subject exposed to a disruptor agent, comprises preparing a testicular or sperm DNA sample from the subject, and observing whether abnormal methylation or gene expression is altered in the testicular or sperm DNA sample.

In another embodiment, a method for identifying genes associated with a disease or dysfunction in the germ-line DNA of an affected transgenerational subject, where the disease and/or dysfunction associated with epigenetic transgenerational DNA alterations, comprises 1) identifying the presence of an altered methylated DNA profile associated with a disease and/or dysfunction in a subject; and 2) identifying genes within the altered methylation DNA profile. The step of identifying the presence of an altered methylated DNA sequence, is selected from the group consisting of, but not limited to, methylation restriction enzyme digestion, microarray analysis with and without bisulfite treated DNA and direct bisulfite sequencing of DNA, and said step of identifying genes is conducted by PCR analysis.

In still another embodiment, a method for developing therapeutic agents for treating a disease or dysfunction in the germ-line DNA of an affected transgenerational subject, where the disease and/or dysfunction associated with epigenetic transgenerational DNA alterations, comprises 1) identifying the presence of an altered methylated DNA profile associated with a disease and/or dysfunction in a subject; 2) identifying genes within the altered methylation DNA profile; and 3) identifying agents that alter the expression of the identified genes.

The Examples, infra, demonstrate the effects of endocrine disruptors on testis development, with delayed effects on adult spermatogenic cell viability and development (i.e. spermatogenesis).

The following Examples are presented to illustrate the present invention and to assist one of ordinary skill in making and using the same. The methodology and results may vary depending on the intended goal of treatment and the procedures employed. The examples are not intended in any way to otherwise limit the scope of the invention.

Example I

This example demonstrates the transgenerational effects of model endocrine disruptors (methoxychlor and vinclozolin), on the testis transcriptome during development, to determine the effects on testis development.

In Vivo Procedures: Gestating outbred Sprague-Dawley and inbred Fisher mother rats from timed, pregnant colonies housed at the Washington State University Vivarium, were given intraperitoneal injections of vinclozolin (100 mg/kg/day) and methoxychlor (200 mg/kg/day) from embryonic day 8-15 (E8-E15, sperm positive vaginal smear date=E0) of gestation (F0 generation) as previously described [123]. Gestating mothers administered vehicle, sesame oil or DMSO, served as controls. At least 6 lines (individual F0 injected females) were generated for controls and treated groups for these analyses. Male rats from control and treated groups were collected at P60-P180 for analyses. F1 treated males were bred to F1 treated females to generate the F2 treated generation and F2 treated males were bred to F2 treated females to generate the F3 generation and the F3 were bred in the same manner to generate the F4 generation. Rats for the control groups were bred in the same manner for all the generations. No inbreeding or sibling crosses were generated. The outcross group (VOC) were generated by breeding the F2 treated males with wild-type females (total of 6 litters) and reverse outcross group (RVOC) was generated by breeding F2 treated females with wild-type males (total of 3 litters). Control (n=4) and treated (n=4) male offspring from the F1 generation from Fisher strain rats were collected at P6 for DNA methylation analysis, see below. All procedures have been approved by the Washington State University Animal Care Committee. The number of animals used for replicates in the experiments (i.e. n value) are as follows for vinclozolin treatment: F1 (control 11, treated 12); F2 (control 19, treated 30); F3 (control 19, treated 26); F4 (control 10, treated 17); VOC (18); and RVOC (6). For methoxychlor treatment animal number was for F1 (control 6, treated 9) and F2 (control 16, treated 22).

Sperm Motility and Concentration Analysis: Animals were sacrificed and cauda epididymal sperm motility was determined using cauda epididymal sperm. Briefly, the epididymis dissected free of connective tissue and a small cut made to the cauda. The tissue as placed in 5 ml of culture medium containing 0.1% BSA for 10 minute at 37° C. An aliquot was placed on a warm slide and gently cover-slipped. The specimen was immediately examined using phase contrast microscopy with 100× magnification. All the motile sperm including rapid progressive, slow progressive and non-progressive were counted according to WHO category [127]. Percent ratio of the motile sperm to the total number of sperm including immotile sperm was calculated. Epididymal sperm count was determined using the same epididymis sample according to a previously described method with some modifications [128].

Histology: Tissues were fixed in Bouin's (Amresco, Solon Ohio) and embedded in paraffin, and then sections stained with hematoxylin and eosin, according to standard procedures. The n=50 treated vinclozolin, n=42 controls.

Detection of Cell Apoptosis: To detect apoptotic cells in testis sections, the Fluorescien In Situ Cell Death Detection Kit (Roche Applied Science, Indianapolis, Ind.) was utilized [123]. This system measures the fragmented DNA from apoptotic cells by enzymatically incorporating fluorecein-12-dUTP at the 3'-OH DNA ends using the enzyme terminal deoxynucleotidyl transferase which forms a polymeric tail using the principle of the TUNEL assay. Fluorescent apoptotic cells were imaged on a confocal microscope and quantitation of number of apoptotic cells per testis cross section. A minimum of n=8 for vinclozolin and n=6 for controls for each generation was used. All cross sections used for TUNEL analysis had normal testis morphology.

DNA Methylation Assays: The methylation status of DNA, isolated from control and endocrine disruptor treated P6 testis, or epididymal sperm, used a combination of methylation sensitive restriction enzymes, and a PCR approach, previously described [129, 131]. Briefly, isolated genomic DNA was incubated and digested with RsaI, with either methylation sensitive (HpaII), or insensitive (MspI) restriction enzymes, followed by PCR, with 10 primer sets designed to amplify methylation sites. PCR products were electrophoretically separated, and visualized by Sybr green staining (Molecular Probes, Eugene, Oreg.), and effects of endocrine disruptors, were determined by the presence or absence of specific bands. The PCR products of interest were isolated, cloned and sequenced to determine chromosomal location by BLAST Genbank analysis [51, 52]. P6 testis analysis was repeated using 4 animals from different litters.

Bisulfite Sequencing: Genomic DNA was isolated from F1 and F4 sperm samples using the DNeasy Tissue Kit (Qiagen, Valencia, Calif.) and digested with Rsa I. Genomic DNA was then treated with sodium bisulfite, following methods previously established [126, 132, 133]. Briefly, 5 μg of digested DNA was denatured in NaOH, then treated with 4.0 M, pH 5.0 sodium metabisulfite for 16 hours at 55° C. Following desalting, DNA was desulfonated with NaOH, neutralized and precipitated with ammonium acetate and ethanol. DNA samples were resuspended in 30 μL, of 1 mM Tris buffer, pH 8.0. Sequence specific primers were generated to amplify the region of interest. PCR products were cloned into pGemT Easy vector (Promega Corporation) and sequenced. Approximately 35 clones from each PCR product were sequenced for analysis of methylation state of the CpG sites. Confirming altered methylation states involved comparisons of the sequence following the bisulfite treatment. The primers for the lysophospholipase PCR bisulfite analysis were 5'GGT ATA TAT AGA GGA AGG TAG GTA GG3' (SEQ ID NO:1) and 5'TAA AAA CCT CCA AAA AAC AAA CAC T3' (SEQ ID NO:2).

Statistical Analysis: The data from apoptotic cell numbers, sperm motility and sperm count were analyzed using a SAS program. The values were expressed as the mean SEM. Statistical analysis was performed, and the difference between the means of treatments and respective controls were determined, using a paired Students t-test. Data from one experiment was averaged and used as one replicate for analysis. In vivo experiments were repeated with 6-30 individuals for each data point. A statistically significant difference was confirmed at $P<0.05$.

Experiment 1

To address potential toxic effects of the endocrine disruptors and identify the optimal timing, previous studies with only the F1 generation have been described [120, 121]. These studies with the use of methoxychlor and vinclozolin (i.e. anti-androgenic endocrine disruptor) in gestating mother animals, have shown no major effect on sex determination, or gross testis histology, throughout development. Animals were exposed in utero E8-E15 then spermatogenic defects were observed in the pubertal and adult F1 generation, [120, 121]. Treated animals had an increase in spermatogenic cell apoptosis. Similar results were observed at postnatal day 20 or day 60, for both endocrine disruptors. In addition to this decreased spermatogenic cell survival, sperm motility and morphology were also found to be impaired, [120, 121], FIG. 1. Interestingly, animals exposed in utero at E15-E20 (i.e. E20 around birth) to the same dose of endocrine disruptor had no spermatogenic cell defects, [120, 121]. Therefore, only exposure in the E8-E15 period of development, had the affects on later adult spermatogenesis, and if exposure was past E15 of testis development, no effect was observed. This correlates with the critical processes such as germ cell re-methylation, cord formation and sex determination during the E10-E15 period, compared to the growth phase after E15. Previous studies of endocrine disruptor actions on the testis that used rats after E15, to be exposed likely did not see effects, due to missing the important E10-E15 period.

Due to the observation that neither a methoxychlor nor vinclozolin transient exposure between E15-E20 had any effect on postnatal/adult spermatogenesis, the effects observed from E8-E15 are not due to artifacts such as postnatal exposure from milk transfer from exposed mothers during weaning, or bedding contamination from the exposed mother, since either E8-E15 or E15-E20 would have the same potential transfer. In addition, no effect on total body weight was observed from either endocrine disruptor treatment, indicating that the effects observed, are not due to effects on growth rates. Therefore, the endocrine disruptor effects observed on the F1 generation, are due to local effects on testis development and germ cell maturation during the E8-E15 period, and not a toxic effect later in development.

None of the transgenerational effects described in this Example, were due to endocrine disruptor toxicity, since none of the subsequent gestating mothers or pups were ever exposed, only the F0 gestating mother. Therefore, the spermatogenic defect observed appears due to the effect of the endocrine disruptor on transient embryonic testis development at the time of sex determination, and not from exposure artifacts or toxicity.

Experiment 2

Vinclozolin was used, and F1 generation male animals were bred to F1 generation females, from different litters, to obtain an F2 progeny. Subsequent breeding continued out four generations with sufficient numbers of animals to avoid any sibling inbreeding artifacts. Adult males from F1, F2, F3, and F4 generations between postnatal days 60 through 180 were collected, and testis isolated for histological examination. Caudal epididymal sperm was collected for sperm counts and motility measurements. Only the original gestating mother (F0) of the F1 generation received a transient endocrine disruptor treatment (E8-E15). A control group of animals were bred in a similar manner for analysis, following vehicle treatment, of the F0 gestating mother. Analysis of cellular apoptosis demonstrated a 2-3 fold increase in spermatogenic cell apoptosis, in the vinclozolin treated animals, for all F1, F2, F3 and F4 generations (FIG. 1A). Sperm numbers were reduced approximately 20%, and sperm forward motility approximately 20%, for all generations (F1-F4) of the vinclozolin treated animals (FIGS. 1B and 1C). Greater than 90% of all males analyzed had the increased spermatogenic cell apoptosis, so nearly all males of all generations were affected.

A similar experiment was performed, using a different endocrine disruptor, methoxychlor. After transient embryonic methoxychlor exposure (E8-E15), a similar phenotype was observed in both the F1 and F2 animals (FIG. 4). Therefore, both vinclozolin and methoxychlor induced transgenerational defects in spermatogenic capacity and sperm viability.

An outcross experiment was performed to determine if the transgenerational phenotype was transmitted through the male germ-line. A vinclozolin F2 generation male (i.e. male progeny from F0 treated mother) was crossed with a wild-type untreated control female, and the offspring analyzed. The vinclozolin outcross (VOC) male also had an increase in spermatogenic cell apoptosis and decrease in sperm number and motility (FIG. 1). The reverse vinclozolin outcross (RVOC) with a treated F0 mother F2 generation female progeny and wild-type male demonstrated no effect on the spermatogenic cells (FIG. 1). Therefore, the endocrine disruptor induced transgenerational phenotype appears to be transmitted through the male germ-line.

The histology of the testis from control and treated animals was similar, for all the 60-day postnatal animals examined, in all F1-F4 vinclozolin generations. Periodically, male rats older than 90 days of age developed infertility associated with small testis and severely reduced spermatogenesis. This occurred in 4 out of a total of 50 F1, F2, F3 and F4 generation animals. Therefore, 8% of the vinclozolin transgenerational animals developed complete infertility. None of the 42 control F1-F4 generation animals developed infertility. The testis histology for a selected infertile vinclozolin F3 generation animal is shown in FIG. 2, and demonstrates a loss of normal spermatogenesis and abnormal seminiferous tubule histology. The control F3 male showed normal histology with normal spermatogenesis, FIG. 2. Although, most of the animals older than 90 days of age were fertile, approximately 20% developed a dramatic decrease in spermatogenic capacity, while 8% developed complete infertility in all the generations examined. The vinclozolin outcrossed (VOC) males also had increased infertility, but the reverse outcross (RVOC) with treated females showed no infertility. Those treated males that were fertile, showed no change in litter size, newborn pup weights or testis weight per body weight when compared to the control animals at any of the F1-F4 generations examined. Nearly all the treated male progeny had the minimal phenotype shown in FIG. 1.

Figure 5:
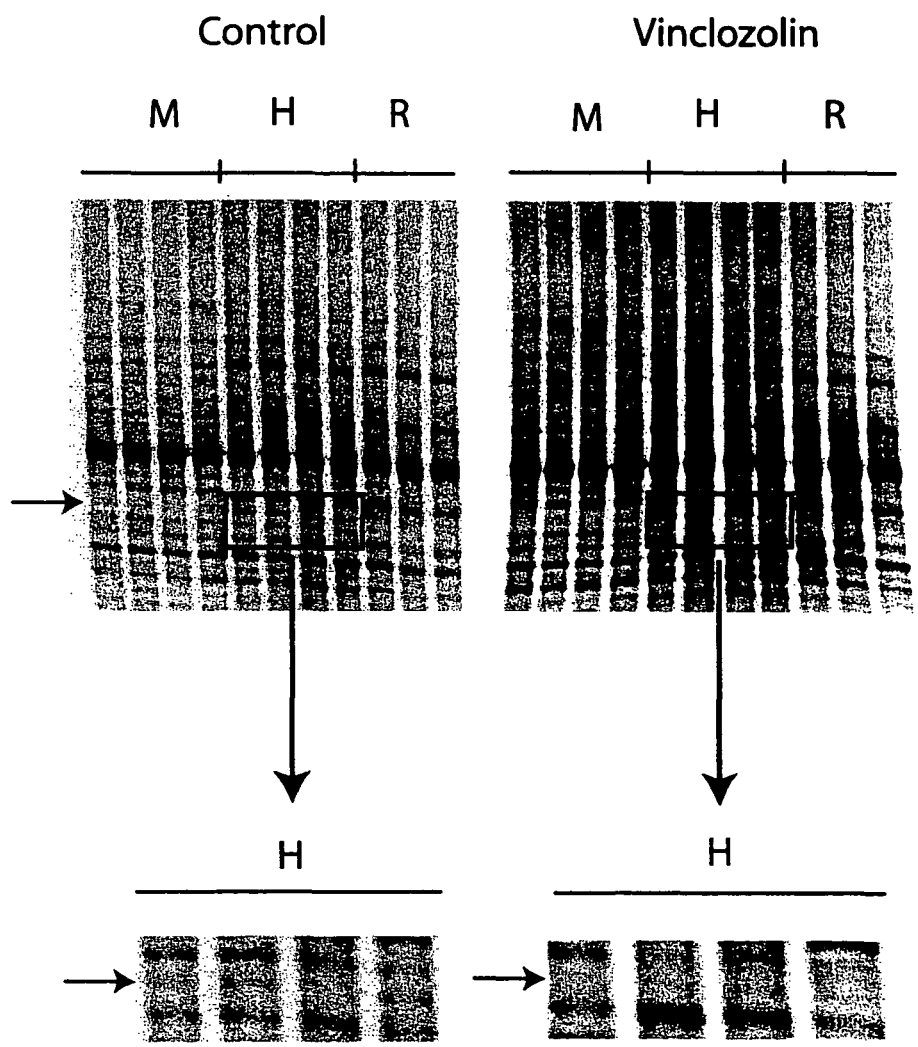
FIG. 5 shows DNA methylation analysis from control and treated P6 testis. Representative gel images are of the PCR based methylation sensitive H-HpaII+RsaI(H) and insensitive MspI+Rsa1 (M), and Rsa1 (R) as control, restriction enzyme digest analysis with representative band (arrow) (200 bp) affected by in vivo exposure to vinclozolin. Postnatal day 6 (P6) testis from control (control) and vinclozolin (treated) treatment is presented. Each lane represents the analysis of a different animal P6 testis (n=4).

The transmission of the endocrine disruptor-induced testis phenotype, in a transgenerational manner, requires an epigenetic alteration of the male germ-line. The only mechanism currently known to influence germ-line transmission, involves the methylation pattern of imprinted genes. The current experiment examined the effects of the endocrine disruptor on the total genome. To determine whether an endocrine disruptor could promote an alteration in methylation, the postnatal day 6 (P6) testis was collected from male F1 progeny of a vinclozolin treated F0 mother, and from males of control animals. Fisher rats were used, because reduced polymorphisms make methylation studies more consistent and reproducible. A polymerase chain reaction (PCR) based methylation sensitive restriction enzyme digestion analysis was used as previously described, [129, 130] to assess changes in DNA methylation patterns (FIG. 5). Multiple animals (n=4) from different litters were analyzed from control and treated animals. The vinclozolin induced altered methylation patterns were similar in the replicate animals. Approximately 25 different PCR products were identified, that had apparent altered DNA methylation patterns from the endocrine disruptor treatment. A representative change in methylation pattern is shown in FIG. 3A.

The methylation experiments were extended, by isolating and cloning several of the DNA fragments, with apparent altered methylation, in response to vinclozolin treatment. Two of the DNA fragments were sequenced and mapped to CpG rich regions on chromosomes 6q32 and 8q32 (FIG. 3B). Clone 7 mapped to 6q32, and was within the lysophospholipase (LPLase) gene (GenBank Accession No. NM144750.1). LPLase is a critical enzyme in the synthesis of important bioactive lipids and associated signaling [134]. Clone 17 mapped to 8q32, and is within 1 kb of the start site of an uncharacterized protein, termed "cytokine inducible SH2 STAT-like containing protein" (GenBank Accession No. AJ243907). The epigenetic transgenerational transmission of the altered methylation pattern through the male germ-line was investigated. PCR primers were designed to the flanking regions of the clone 17 gene, cytokine inducible SH2 STAT-like protein, and used to investigate altered methylation with the methylation sensitive restriction enzyme digest. Epididymal sperm were isolated from F2 and F3 vinclozolin generation animals for analysis. As shown in FIG. 3C, the control animals had the PCR product while the vinclozolin F2 and F3 animals did not. The control RsaI digest had a PCR product in all samples. Therefore, the vinclozolin F2 and F3 generation selected sperm samples appeared to have altered methylation in this clone 17 gene compared to control animal sperm. To confirm the methylation changes an alternate bisulfite DNA sequence analysis was used [131-133]. Bisulfite treatment analysis confirmed the altered methylations of the lysophospholipase gene within the CpG island identified (FIG. 6). This bisulfite altered sequence was observed in approximately 25% of the vinclozolin treated sperm DNA samples analyzed. These results demonstrate that the endocrine disruptors induce an epigenetic transgenerational change in the DNA methylation pattern of the mammalian male germ-line.

These results show that at least two different endocrine disruptors, vinclozolin and methoxychlor, after a transient embryonic exposure, at a critical time during sex determination (E8-E15 in the rat), but not later (E15-20), promote an adult male testis phenotype of decreased spermatogenic capacity and male infertility. No gross abnormality was observed in any other tissues examined, and serum testosterone levels were found to be normal in all the animals. This phenotype was found to be transgenerational, and is associated with altered DNA methylation of the male germ-line. This phenotype was observed in nearly all males from all vinclozolin generations, such that a genetic mutation (e.g. segregation), is likely not a major factor. It is likely that this epigenetic transgenerational effect on the germ-line induces a variety of other diseases.

In female animals, preliminary data demonstrate no major effect on the female ovary, but a number of abnormal pregnancy outcomes were observed in vinclozolin generations (F1, F2 and F3) pregnant females, but not controls. The abnormal phenotype has similarities to pre-eclampsia that include death, severe anemia and blood cell defects, occurring in approximately 15% of all pregnancies in vinclozolin-generation females. Other disease states, as such as prostate abnormalities, tumor development, abnormal immune system activation and premature aging, may be induced by the epigenetic transgenerational actions of the endocrine disruptors.

These results demonstrate that an environmental factor such as an endocrine disruptor, can induce an epigenetic transgenerational (i.e. multiple generations, F2) phenotype (male infertility) through an apparent reprogramming of the mammalian male germ-line. Specifically, the data showing epigenetic effects of endocrine disruptors on male germ cell DNA methylation, correlate with observations of the required re-methylation of germ cells, during the embryonic sex determination period, and provides a causal mechanism for the transgenerational effects observed.

Previous studies with F1 generation publication [120, 121], did not demonstrate the epigenetic transgeneration phenotype observed in the examples, herein, but simply addressed the lack of toxicology and clarified the phenotype to examine.

Example II

Transgenerational Epigenetic Imprinting of the Male Germ-Line by Endocrine Disruptor Exposure During Gonadal Sex Determination Sperm collections: Rats were treated using vinclozolin (100 mg/kg per day) from embryonic day 8-15 (E8-15) of gestation as described above in Example II. In brief, four lines (individual F0 treated females) were generated for control and four lines were generated for vinclozolin experimental groups. F1 vinclozolin generation males were bred to F1 vinclozolin generation females to generate the F2 vinclozolin generations and F2 vinclozolin generation animals bred to generate the F3 vinclozolin generation animals. Rats for the control groups were bred in the same way for all the generations. No sibling breeding occurred to avoid any inbreeding artifacts. Male rats from control and vinclozolin generation animals were collected at postnatal day 60-180 (P60-P180) for analyses. Animals were euthanized and cauda epididymal sperm was collected for further experiments. Briefly, the cauda epididymis was dissected and placed in pre-warmed F12 media containing 1% BSA for 30 min at 37° C. as previously described [121]. Sperm were collected from the media for DNA isolation. The inbred strain of Fisher (CDF) rat was used for the initial methylation screen to identify the candidate methylation sites due to the lack of DNA polymorphisms. To eliminate epigenetic effects from being masked by outbred polymorphism and confirm the methylation changes observed, the outbred strain of Sprauge-Dawley (SD) rats was used for the bisulfite analysis, to investigate altered methylation between F1-F3 generations, and for the microarray gene expression data.

DNA methylation assay: The methylation state of the DNA isolated from CDF control and vinclozolin generation epididymal sperm was determined using a combination of methylation sensitive restriction enzymes and PCR procedures (MSRE-PCR) described above in Example I. Briefly, genomic DNA was isolated from sperm samples using the DNeasy Tissue Kit (Quiagen, Valencia, Calif.). Two micrograms each of control and vinclozolin generation sperm DNA were separately digested with RsaI and either methylation-sensitive enzyme HpaII or insensitive MspI enzymes, followed by PCR with specific primer sets (Table 1). PCR products were electrophoretically separated on polyacrylamide gels and visualized by ethidium bromide staining. The PCR products (i.e. bands) that were reproducibly absent or present between control and vinclozolin generation sperm DNA were excised from stained gels, re-amplified with the same PCR primer set, and then cloned and sequenced. The DNA sequence and chromosomal location were determined using the NCBI Rat genomic databank BLAST system.

TABLE 1

Identification of 25 candidates isolated from methylation sensitive restriction enzymes-PCR (MSRE-PCR) screen.

| Candidate No. | Location | Identification (Rat Accession number) |
|---|---|---|
| 1 | Exon/Intron | Neural cell adhesion molecule 1 (NCAM1) (NM_031521)/Similar to phosphoglycerate mutase LOC503205 (XM_573155) |
| 2, 3, 24 | Non-coding region | Leucine-rich protein 157 (Lrpprc) (NM_001008519)/Protein phosphatase 1B (Ppm1b) (NM_033096) |
| 4, 19 | Intron | Calcium channel, voltage-dependent, L type, alpha 1E subunit (Cacna1e) (NM_019294) |
| 5, 6, 9 | Exon/Intron | Similar to FLJ22405 protein (XM_232266) |
| 7 | Non-coding region | Similar to ankyrin repeat domain protein 28 (Ankrd28) (LOC306264) (XW_224620.3)/Polypeptide N-acetylgalatosaminyl transferase (Galntl2-predicted) (NW_047469) |
| 8 | Non-coding region | Liprin-alpha 1 (Ppfia1) (XM_341856)/Fas (TNFRSF6)-associated via death domain (Fadd) (NW_047563) |
| 10 | Unknown | No significant similarity found |
| 11 | Non-coding region | 60S ribosomal protein L7a (LOC502773) (NW_047693)/RIKEN cDNA 1200009022 (LOC362364) (NM_001034010) |
| 12 | Promoter | Similar to importin 7 (LOC501910) (NC_005113) |
| 13 | Intron | Nuclear factor I/X (Nfix) (AB012234) |
| 14, 15 | Non-coding region | Leucine rich repeat neuronal 6A (Lrrn6a) (XM_236268) |
| 16 | Promoter/Exon/Intron | Optineurin (Optn) (NM_145081) |
| 17, 18 | Promoter | Nicastrin (Ncstn) (NM_174864)/Coatomer protein complex subunit alpha (Copa) (XM_222899) |
| 20 | Unknown | No significant similarity found |
| 21, 32 | Exon/Intron | Similar to phosphoglycerate mutase B chain (LOC503205) (XM_573155)/NCAM1 (NM_031521) |
| 22 | Intron | Similar to golgi autoantigen golgin subtype a4 (tGolgin-1) (LOC501069) (XM_236718) |
| 23 | Non-coding region | Similar to ribosomal protein (LOC503150) (XP_578671)/U1 small nuclear ribonucleoprotein subunit (snRP1c) (LOC503151) (XP_578672) |
| 25 | Non-coding region | Major urinary protein 4 (Mup4) (NM_198784)/similar to Major urinary protein precursor (MUP, alpha-2u-globulin) (LOC502951) (XM_578456) |
| 26 | Promoter | Acetyl-coenzyme A carboxylase alpha (Acaca) (NM_022193) |
| 27, 28 | Intron | Zinc finger protein 212 (Zpf212) (XM_231749) |
| 29 | Non-coding region | Runt related transcription factor 1 (Runx1) (NM_017325)/Similar to cell wall protein Awa1p (LOC501772) (XP_577171) |
| 30 | Unknown | No significant similarity found |
| 31 | Non-coding region | Wiskott-Aldrich syndrome protein interacting protein (Waspip) (NM_057192)/hypothetical protein (LOC499811) (XP_580019) |
| 33 | Non-coding region | Sine oculis homeobox homolog 3 (Six3) (NM_023990)/Six2 predicted (XP_345631) |
| 34 | Promoter | RAB12 (rat GTP-binding protein Rab12), member RAS oncogene family (XM_343639) |

Bisulfite sequencing: Bisulfite sequencing was used to characterize the DNA methylation patterns and changes. Genomic DNA was isolated from control and vinclozolin F2 and F3 generation epididymal sperm using the DNeasy Tissue Kit. Genomic DNA (10 µg) was digested with RsaI then treated with bisulfite as described above for Example I. After purification, the bisulfite converted DNA was used as a template for PCR. The bisulfite primers for each candidate were designed using MethPrimer (www.urogene.org/methprimer) system (Li and Dahiya, 2002) and are listed in Table 2. The sequence specific primers were generated to amplify the CpG region of interest to characterize the methylation pattern. PCR conditions for amplification were as follows: 30 cycles followed by another 30 cycles with nested primers (30 s at 95° C., 45 s at 50° C., and 50 s at 72° C.) and then 5 min at 72° C. with modified 1× buffer [10×: 166 mM $(NH_4)_2.SO_4$; 670 mM Tris pH 8.8; 67 mM $MgCl_2$; 100 mM β-mercaptoethanol]. PCR products were cloned into pGEM-T easy vector (Promega) and sequenced using Big-Dye Terminator (Applied BioSystems). Approximately 50 different clones from each PCR product were sequenced to characterize the methylation state of the CpG sites identified. A mixture of a minimum of 3 different F2 or F3 generation control and vinclozolin animals were used to generate approximately 50 clones per candidate analyzed. Statistical differences between methylation states were determined with a Fisher's Exact Test.

TABLE 2

Primers for PCR Procedures

| Candidate Primer # | Seq (5' → 3') | Purpose | Tm. (° C.) | Cycle number | Product size, bp |
|---|---|---|---|---|---|
| Consensus MSRE-PCR Primers | | | | | |
| MSAPPCR1 | AACCCTCACCCTAACCCCGG (SEQ ID NO: 3) | MSAPPCR | 40, 55 | 35 | <1000 |
| MSAPPCR2 | AACCCTCACCCTAACCGCGG (SEQ ID NO: 4) | MSAPPCR | 40, 55 | 35 | |
| MSAPPCR3 | AACCCTCACCCTAACCCGCG (SEQ ID NO: 5) | MSAPPCR | 40, 55 | 35 | |
| MSAPPCR4 | AACCCTCACCCTAACCGGCC (SEQ ID NO: 6) | MSAPPCR | 40, 55 | 35 | |

TABLE 2-continued

Primers for PCR Procedures

| Candidate Primer # | Seq (5' → 3') | Purpose | Tm. (° C.) | Cycle number | Product size, bp |
|---|---|---|---|---|---|
| Bisulfite Analysis Primers | | | | | |
| 01-bsF1 | AGGAGTGGAAGGAGTTTGGTAATAT (SEQ ID NO: 7) | 1st PCR | 44 | 40 | 237 |
| 01-bsR1 | TACCCCCTAATCAAAACCTAATAAAA (SEQ ID NO: 8) | 1st PCR | 44 | 40 | |
| 01-bsF2 | GGTAATATTGGTTGTTTGGAATGT (SEQ ID NO: 9) | 2nd PCR | 44 | 40 | |
| 01-bsR2 | ACCCCCTAATCAAAACCTAATAAAA (SEQ ID NO: 10) | 2nd PCR | 44 | 40 | |
| 02-bsF1 | TTTAAATTTTAGTATTTATTAATTGGGTAA (SEQ ID NO: 11) | 1st PCR | 44 | 40 | 400 |
| 02-bsF2 | TTATTAATTGGGTAATTGATTATTT (SEQ ID NO: 12) | 2nd PCR | 44 | 40 | |
| 02-bsR1 & 2 | TCTCCTAACACCATCTAACATACCTAAC (SEQ ID NO: 13) | 1st & 2nd PCR | 44 | 40 | |
| 04-bsF1 | GTATTTATTAATTGGGTAATTGATTATTTT (SEQ ID NO: 14) | 1st PCR | 44 | 40 | 338 |
| 04-bsR1 | TCTCCTAACACCATCTAACATACCTAAC (SEQ ID NO: 15) | 1st PCR | 44 | 40 | |
| 04-bsF2 | ATTAATTGGGTAATTGATTATTTTATATTT (SEQ ID NO: 16) | 2nd PCR | 44 | 40 | |
| 04-bsR2 | ACCAAAACCTAATACTATTAAAACT (SEQ ID NO: 17) | 2nd PCR | 44 | 40 | |
| 05-bsF1 | TTTGAGGGGATTTGAGGTTG (SEQ ID NO: 18) | 1st PCR | 44 | 40 | 226 |
| 05-bsF2 | GGGTTTTATTGTTTTTTTAGGTAGTT (SEQ ID NO: 19) | 2nd PCR | 44 | 40 | |
| 05-bsR1 & 2 | TACAAAAAAATCTCCTTCCAACTCT (SEQ ID NO: 20) | 1st & 2nd PCR | 44 | 40 | |
| 07-bsF1 | TTATTTAGTTTTTTTTGTTTTTTTT (SEQ ID NO: 21) | 1st PCR | 44 | 40 | 302 |
| 07-bsR1 | TTAATCTTAAAATACCCCCTTTATATC (SEQ ID NO: 22) | 1st PCR | 44 | 40 | |
| 07-bsF2 | TTTTTAGTGTTTTTAGTGTTTTTTTT (SEQ ID NO: 23) | 2nd PCR | 44 | 40 | |
| 07-bsR2 | CTATACAACCTCTCAATCTATCTACC (SEQ ID NO: 24) | 2nd PCR | 44 | 40 | |
| 08-bsF1 | AATAGTAAGGGTAGGGTGTTGGTTT (SEQ ID NO: 25) | 1st PCR | 44 | 40 | 398 |
| 08-bsF2 | GTTAAGTTAGAGGGTTTTTTATGGG (SEQ ID NO: 26) | 2nd PCR | 44 | 40 | |
| 08-bsR1 & 2 | AAAATTCAAACTAACCACCAACATT (SEQ ID NO: 27) | 1st & 2nd PCR | 44 | 40 | |
| 11-bsF1 | TGATAAAATAAGATTAAGAAGGTTGAGAG (SEQ ID NO: 28) | 1st PCR | 44 | 40 | 163 |
| 11-bsF2 | TTGAGAGGAAGGAAAGAGTTTTTAAG (SEQ ID NO: 29) | 2nd PCR | 44 | 40 | |
| 11-bsR1 & 2 | TATTCCTCACTTCTCAAAAAAACC (SEQ ID NO: 30) | 1st & 2nd PCR | 44 | 40 | |
| 12-bsF1 & 2 | TTATTGTGGCAATTATGAGGTTTTT (SEQ ID NO: 31) | 1st & 2nd PCR | 44 | 40 | 423 |
| 12-bsR1 | TCAATCTTCTTCTAAAATAATATATAAA (SEQ ID NO: 32) | 1st PCR | 44 | 40 | |
| 12-bsR2 | TTAAACTATACCCTATTAACTCAAATAAAT (SEQ ID NO: 33) | 2nd PCR | 44 | 40 | |
| 13-bsF1 & 2 | GGATTTTGAGAGAGAAAAGGAGTTATAA (SEQ ID NO: 34) | 1st & 2nd PCR | 44 | 40 | 376 |
| 13-bsR1 & 2 | AAACAAAACAAAAACCAAAAAAA (SEQ ID NO: 35) | 1st & 2nd PCR | 44 | 40 | |
| 14-bsF1 & 2 | GTGTAGGTGGAAGTTATTGTTTGGT (SEQ ID NO: 36) | 1st & 2nd PCR | 44 | 40 | 192 |
| 14-bsR1 | TCCTCAAAATCAAAACCATTCTA (SEQ ID NO: 37) | 1st PCR | 44 | 40 | |
| 14-bsR2 | CCTCAAAATCAAAACCATTCTAAA (SEQ ID NO: 38) | 2nd PCR | 44 | 40 | |
| 16-bsF1 & 2 | ATTGGAGGGAAAGTTAGTAATTTTG (SEQ ID NO: 39) | 1st & 2nd PCR | 44 | 40 | 447 |
| 16-bsR1 | AAAATACAACCCTACACCATCATAC (SEQ ID NO: 40) | 1st PCR | 44 | 40 | |
| 16-bsR2 | TATAAATAAACCCCTTAACCCTACC (SEQ ID NO: 41) | 2nd PCR | 44 | 40 | |
| 17-bsF1 & 2 | GGGGTGATTTTATTTGTTAGTATTA (SEQ ID NO: 42) | 1st & 2nd PCR | 44 | 40 | 333 |

TABLE 2-continued

Primers for PCR Procedures

| Candidate Primer # | Seq (5' → 3') | Purpose | Tm. (° C.) | Cycle number | Product size, bp |
|---|---|---|---|---|---|
| 17-bsR1 | TAAACTCTTCCAATAAACCCAATTC (SEQ ID NO: 43) | 1st PCR | 44 | 40 | |
| 17-bsR2 | TTTAATTAACATCCTTCAAACCTTC (SEQ ID NO: 44) | 2nd PCR | 44 | 40 | |
| 21-bsF1 & 2 | AAAAATATATGTGTATAAAAGTAAAAATAA (SEQ ID NO: 45) | 1st & 2nd PCR | 44 | 40 | 296 |
| 21-bsR1 & 2 | ATCAATCTAATTCAAACAATTCCTC (SEQ ID NO: 46) | 1st & 2nd PCR | 44 | 40 | |
| 22-bsF1 | ATTTGTTGGTTGGAAGTATGAATTAG (SEQ ID NO: 47) | 1st PCR | 44 | 40 | 318 |
| 22-bsF2 | ATTTGTTGGTTGGAAGTATGAATTAG (SEQ ID NO: 48) | 2nd PCR | 44 | 40 | |
| 22-bsR1 & 2 | ACAACAACCTATAAATCCACCATATC (SEQ ID NO: 49) | 1st & 2nd PCR | 44 | 40 | |
| 23-bsF1 | GGGTAGTGTAGGAGAGATGGTTTTA (SEQ ID NO: 50) | 1st PCR | 44 | 40 | 260 |
| 23-bsF2 | AGGTTTAGGTTTAGAGTTTTGAGTTG (SEQ ID NO: 51) | 2nd PCR | 44 | 40 | |
| 23-bsR1 & 2 | TATACCCCACAATACACCCTTTTAC (SEQ ID NO: 52) | 1st & 2nd PCR | 44 | 40 | |
| 25-bsF1 & 2 | TTTTTAGGTGGTTAGTGAGGGTATG (SEQ ID NO: 53) | 1st & 2nd PCR | 44 | 40 | 209 |
| 25-bsR1 | AAAAAATCCTCAACCATAAACAAAA (SEQ ID NO: 54) | 1st PCR | 44 | 40 | |
| 25-bsR2 | AATCCTCAACCATAAACAAAAACTC (SEQ ID NO: 55) | 2nd PCR | 44 | 40 | |
| 26-bsF1 | GGTTATTGTTTATGATTTATTTTTTT (SEQ ID NO: 56) | 1st & 2nd PCR | 44 | 40 | 164 |
| 26-bsR1 | TCTCCTCTAAATCCAACTTTACCAA (SEQ ID NO: 57) | 1st PCR | 44 | 40 | |
| 26-bsR2 | TCATCTTCTAAATTATCTTCAAACAC (SEQ ID NO: 58) | 2nd PCR | 44 | 40 | |
| 27-bsF1 | TATTTTTATTTTGATAATTGTTTGTAAGT (SEQ ID NO: 59) | 1st PCR | 44 | 40 | 206 |
| 27-bsR1 | AAAACAACAACCTAAAAATTCAATCAT (SEQ ID NO: 60) | 1st PCR | 44 | 40 | |
| 27-bsF2 | ATTTTTATTTTGATAATTGTTTGTAAGTA (SEQ ID NO: 61) | 2nd PCR | 44 | 40 | |
| 27-bsR2 | ACATTTTCTAAATTTAAACCCTACACTC (SEQ ID NO: 62) | 2nd PCR | 44 | 40 | |
| 29-bsF1 | GGGTTAGAGAGGTTGTAGGAGGTAG (SEQ ID NO: 63) | 1st & 2nd PCR | 44 | 40 | 261 |
| 29-bsR1 | AAAACCACACCCTTAAAAAAAACTAA (SEQ ID NO: 64) | 1st & 2nd PCR | 44 | 40 | |
| 31-bsF1 | TGGTTTATGTTTATAGGGATTTTTTTT (SEQ ID NO: 65) | 1st PCR | 44 | 40 | 295 |
| 31-bsF2 | GGTTTATGTTTATAGGGATTTTTTTT (SEQ ID NO: 66) | 2nd PCR | 44 | 40 | |
| 31-bsR1 & 2 | AACACATACCTTTTATCTCAACACTCTAA (SEQ ID NO: 67) | 1st & 2nd PCR | 44 | 40 | |
| 33-bsF1 & 2 | GTAGAGTTTGGGGAAGGATTTTAG (SEQ ID NO: 68) | 1st & 2nd PCR | 44 | 40 | 264 |
| 33-bsR1 | ACCCAAAAATAAAAACAAAAACAAA (SEQ ID NO: 69) | 1st PCR | 44 | 40 | |
| 33-bsR2 | AAAAACAAAAACAAAACATAACCAC (SEQ ID NO: 70) | 2nd PCR | 44 | 40 | |
| 34-bsF1 & 2 | GTTTGTGATTATTGTTTGGAATTTAG (SEQ ID NO: 71) | 1st & 2nd PCR | 44 | 40 | 185 |
| 34-bsR1 | CAAAAATCTAAAAAAAACAACAACC (SEQ ID NO: 72) | 1st PCR | 44 | 40 | |
| 34-bsR2 | AACAACAACCCAATTAATTTAACC (SEQ ID NO: 73) | 2nd PCR | 44 | 40 | |
| H19-bsF1 | AGGATATATGTATTTTTAGGTTGGTT (SEQ ID NO: 74) | 1st PCR | 58 | 40 | 337 |
| H19-bsR1 | ACTAATAACCCCAAAACCCCATAT (SEQ ID NO: 75) | 1st PCR | 58 | 40 | |
| Gene Specific MSRE-PCR Primers | | | | | |
| 01-GRF1 | AGCCATCAGTCAGAGGGAGA (SEQ ID NO: 76) | Genomic-RE PCR | 55 | 25 | 535 |
| 01-GRR1 | GCCATTGATTCCCAGAAGTC (SEQ ID NO: 77) | Genomic-RE PCR | 55 | 25 | |

TABLE 2-continued

Primers for PCR Procedures

| Candidate Primer # | Seq (5' → 3') | Purpose | Tm. (° C.) | Cycle number | Product size, bp |
|---|---|---|---|---|---|
| 14-GRF1 | CTCCCTCTCTCCCTTTTGCT (SEQ ID NO: 78) | Genomic-RE PCR | 55 | 25 | 837 |
| 14-GRR1 | TGACAGAGGGCTGGTCTCTC (SEQ ID NO: 79) | Genomic-RE PCR | 55 | 25 | |
| 17-GRF1 | GGGTCCCTTCCAGTCTCTTAGC (SEQ ID NO: 80) | Genomic-RE PCR | 57 | 25 | 646 |
| 17-GRR1 | AGTGACTGACTCCGGAAAAAGC (SEQ ID NO: 81) | Genomic-RE PCR | 57 | 25 | |
| 27-GRF1 | ATCCCTGCATGAGGACTACGTT (SEQ ID NO: 82) | Genomic-RE POR | 57 | 25 | 615 |
| 27-GRR1 | CCGTGTTGATACAAGGTGCATT (SEQ ID NO: 83) | Genomic-RE PCR | 57 | 25 | |
| 33-GRF1 | TTGTCAGAGGTTGGCTAGGG (SEQ ID NO: 84) | Genomic-RE PCR | 55 | 25 | 612 |
| 33-GRR1 | CGCCACAGCATGAGTAAAGA (SEQ ID NO: 85) | Genomic-RE PCR | 55 | 25 | |
| RT PCR Primers | | | | | |
| Ncam1F | GTCTGTCACCCTGGTGTGTG (SEQ ID NO: 86) | RT-PCR | 56 | 25 | 351 |
| Ncam1R | GTGGACGTTCTCCAGGTGAT (SEQ ID NO: 87) | RT-PCR | 56 | 25 | |
| L19F | CTGAAGGTCAAAGGGAATGTG (SEQ ID NO: 88) | RT-PCR | 56 | 25 | 195 |
| L19R | GGACAGAGTCTTGATGATCTC (SEQ ID NO: 89) | RT-PCR | 56 | 25 | |

Genomic DNA and Methylation Sensitive Restriction Enzyme PCR: Genomic DNA was isolated from the different control and vinclozolin F1-F3 generation epididymal sperm samples. A total of 1 µg of genomic DNA was digested using methylation-sensitive HpaII or AciI enzymes (37° C., 6-12 hr). The digested DNA was precipitated and dissolved in 30 µl of dH$_2$O. Then, 3 µl aliquots were analyzed by PCR in 30 µl reactions with specific primers (Table 1), subjected to 25 cycles, and the PCR products electrophoretically separated on 1.5% agarose. The differences between the control and vinclozolin F1-F3 generation sperm samples were determined for selected genes found to have high optimal digestion capacity.

Microarray analysis: RNA was collected from embryonic day 13, 14 and 16 (E16) testis from control and E16 vinclozolin F1 and F2 generation animals as described above for Example I. RNA was hybridized to the Affymetrix (Affymetrix, Santa Clara, Calif.) rat 230A gene chip. The Genomics Core in the Center for Reproductive Biology at Washington State University, Pullman, Wash., performed the analysis as previously described, and incorporated by reference herein [149, 150]. Briefly, RNA from the cells was reverse transcribed into cDNA then was transcribed into biotin labeled RNA. Biotin labeled RNA was then hybridized to the Affymetrix rat 230A gene chips. Each gene set is composed of 16 pairs of 24-mer oligonucleotides, with one sense strand specific for the gene and one anti-sense strand with single point mutations for use as a comparative negative control. Biotinalated RNA was then visualized by labeling with phycoerythrin-coupled avidin. The microarray was scanned on a Hewlett-Packard Gene Array Scanner (Hewlett-Packard Co., Palo Alto, Calif.).

Bioinformatics: The majority of the data analysis was performed using the Affymetrix Microarray Suite Software (Affymetrix, Santa Clara, Calif.). Most of this study uses the comparison analysis software offered and analysis parameters described above in Example I [150]. Two repeats for each control and vinclozolin F1 and F2 generation E16 testis, were performed and allowed four comparisons in the experiment. Only genes that displayed a consistent expression over all four comparisons and had a relative hybridization intensity of at least 50 were included in the analysis. Basic expression analysis was determined by accessing the Affymetrix database through the Microarray Suite Software. A pathway analysis was performed by the Pathway Assist Gene Spring Software (Silicon Genetics).

Gestating rats were transiently exposed to the anti-androgenic endocrine disruptor vinclozolin during embryonic gonadal sex determination (E8-E14), as described above for Example I. Subsequent F1, F2 and F3 generation progeny from control and vinclozolin treated F0 mothers were produced. The F0 mothers used for the control (vehicle treatment, n=4) and vinclozolin treatment (n=4) were littermate sisters, such that the genetic background of the control and vinclozolin generations were similar. The control and vinclozolin generation animals were maintained in the same conditions (i.e. room, rack, feed), but kept in different cages. The control and vinclozolin (F1-F3) generation males were euthanized as adults (i.e. 90-180 days of age), and then epididymal sperm collected and DNA isolated. These sperm DNA samples were used to investigate the potential epigenetic changes (i.e. DNA methylation) between the control and vinclozolin generation male germ-line.

Figure 7:
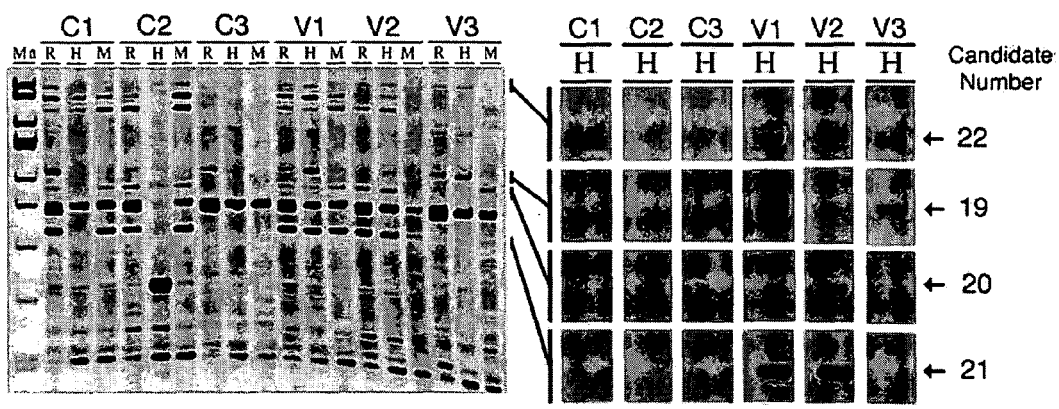
FIG. 7 shows DNA methylation analysis from control (C) and vinclozolin (V) F3 caudal epididymal sperm. Representative gel image of the PCR based methylation sensitive HpaII+RsaI (H lanes), insensitive MspI+RsaI (M lanes) and control RsaI (R lanes) as digests. Bands that appeared to be differentially methylated between matched control and vinclozolin samples are enlarged for H bands and indicated by arrows for the specific candidates #19, 20, 21, 22. The size DNA 100 bp ladder is in the left lane (Ma).
Figure 8:
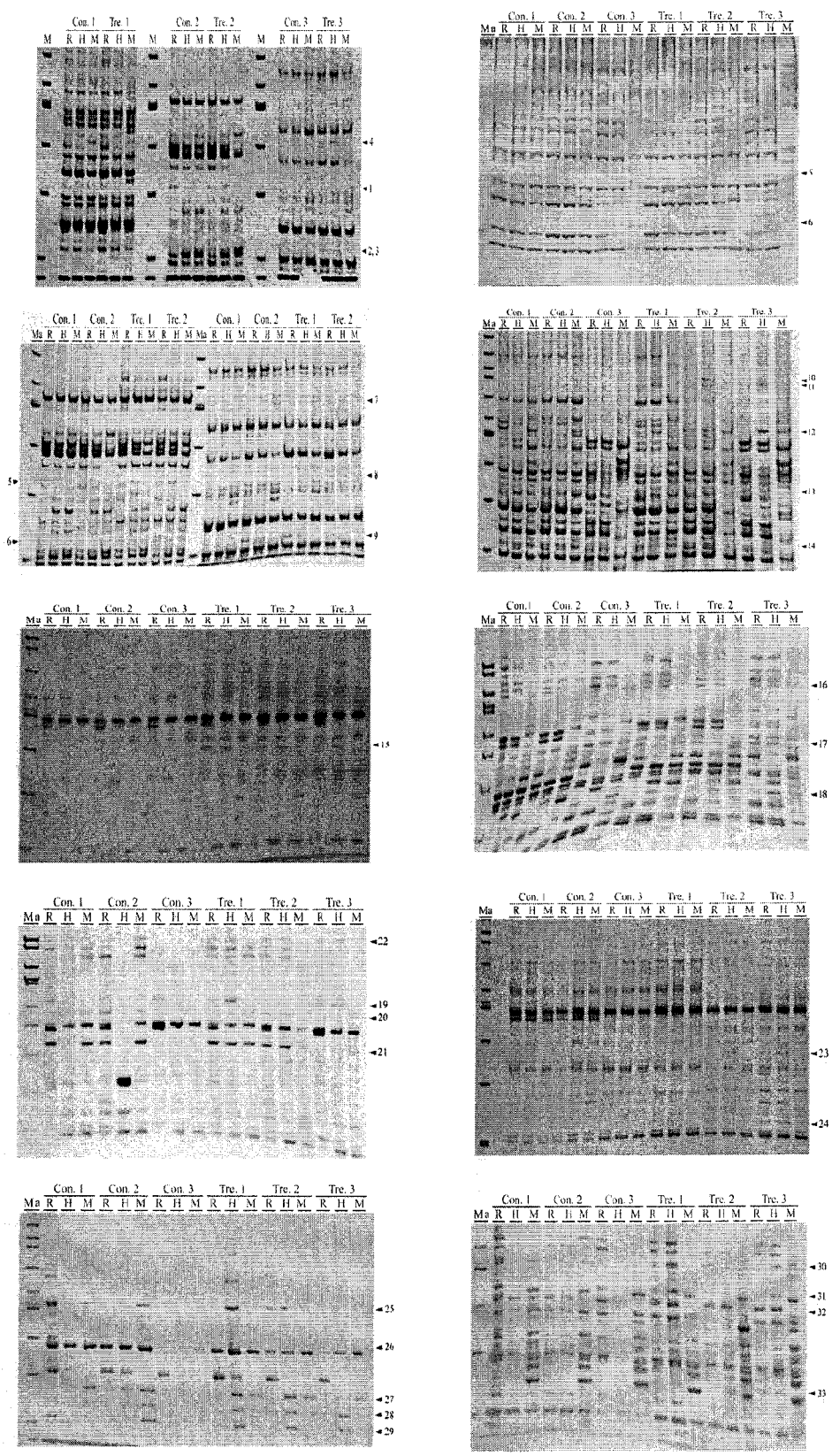
FIG. 8 shows DNA methylation analysis of F3 generation control (Con) and vinclozolin (Tre) caudal epidermal sperm. Gel images of PCR based methylation sensitive restriction analysis screen as described in detail in Example II, infra. All candidates are listed on the right margin.
Figure 9:
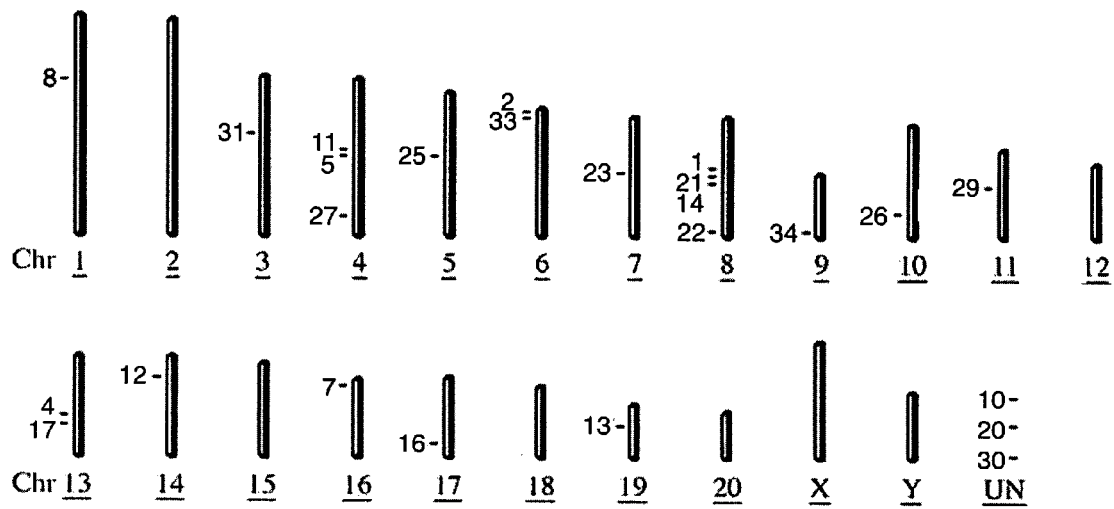
FIG. 9 shows the chromosome location and physical-mapping of each candidate (numbers) is indicated for each chromosome (Chr), with those unknown (UN) sequences not mapped, indicated.

The F3 generation samples were used to identify alterations in DNA methylation between control and vinclozolin generation sperm. This analysis assures that the changes observed are due to a transgenerational epigenetic, and not due to toxicology, that could be present in the F1 generation. The analysis of methylation used a methylation sensitive restriction enzyme (MSRE) procedure that involved the use of 10 different sets of PCR primers to consensus CpG methylation sites (MSRE-PCR). Sperm DNA from control and vinclozolin F3 generation animals (i.e. Fisher rats), from three different preparations, containing a minimum of three different animals, were analyzed. A representative gel for one set of PCR primers is shown in FIG. 7A-7C, with the 3 control and vinclozolin samples shown. Differences in the methylation sensitive restriction enzyme Hpa-II (H) digest demonstrated the presence of PCR products (bands) in the vinclozolin samples, but not control samples, FIG. 7. If differences in the PCR products (bands) occurred in a minimum of two of the three replicate animals they were selected for further analyses. This analysis generated 34 candidates with potential altered DNA methylation between control and vinclozolin sperm samples and were numbered 1-34, Table 1. The representative differences for candidates #19-22 are shown in FIG. 7, and for the other gels and candidates in FIG. 8. Interestingly, all candidates selected were present in the vinlcozolin samples, but not in the control samples. There were no candidates that were present in the control sample and absent in the vinclozolin samples. The PCR product (i.e. band) for all the candidates were excised from the gels, subcloned and then sequenced. The characterization of the candidates is shown in Table 1. The presence of more than one candidate number together (e.g. 2, 3, 24) indicates similar sequences being present in the different candidates. The gene(s) nearest the candidate sequences are listed with GenBank accession numbers. The physical map (i.e. location) of the candidate DNA methylation site is shown as being in the promoter, exon, intron or distal non-coding region of DNA, Table 1. The sequence was considered in the promoter of a gene if it was within 1000 bp upstream of the transcriptional start site of the gene of interest. The chromosomal location of all the candidate DNA methylation sequences is shown in FIG. 9A-9B. The candidate altered methylation sites are present on various autosomes with no major hot spot regions and none present on the sex chromosomes. The rat genome is not complete, so several candidate sequences could not be localized and appear to be on uncharacterized chromosomal regions, FIG. 9A-9B. Therefore, the MSRE-PCR screen identified 25 individual candidate DNA sequences with potential altered methylation sites, that are different between control and vinclozolin generation F3 sperm DNA samples, Table 1. As discussed below, some of these candidates fall within the promoters, exons or introns of specific genes, while others are non-coding regions distal to a gene and the nearest gene(s) are listed, Table 1.

Figure 12:
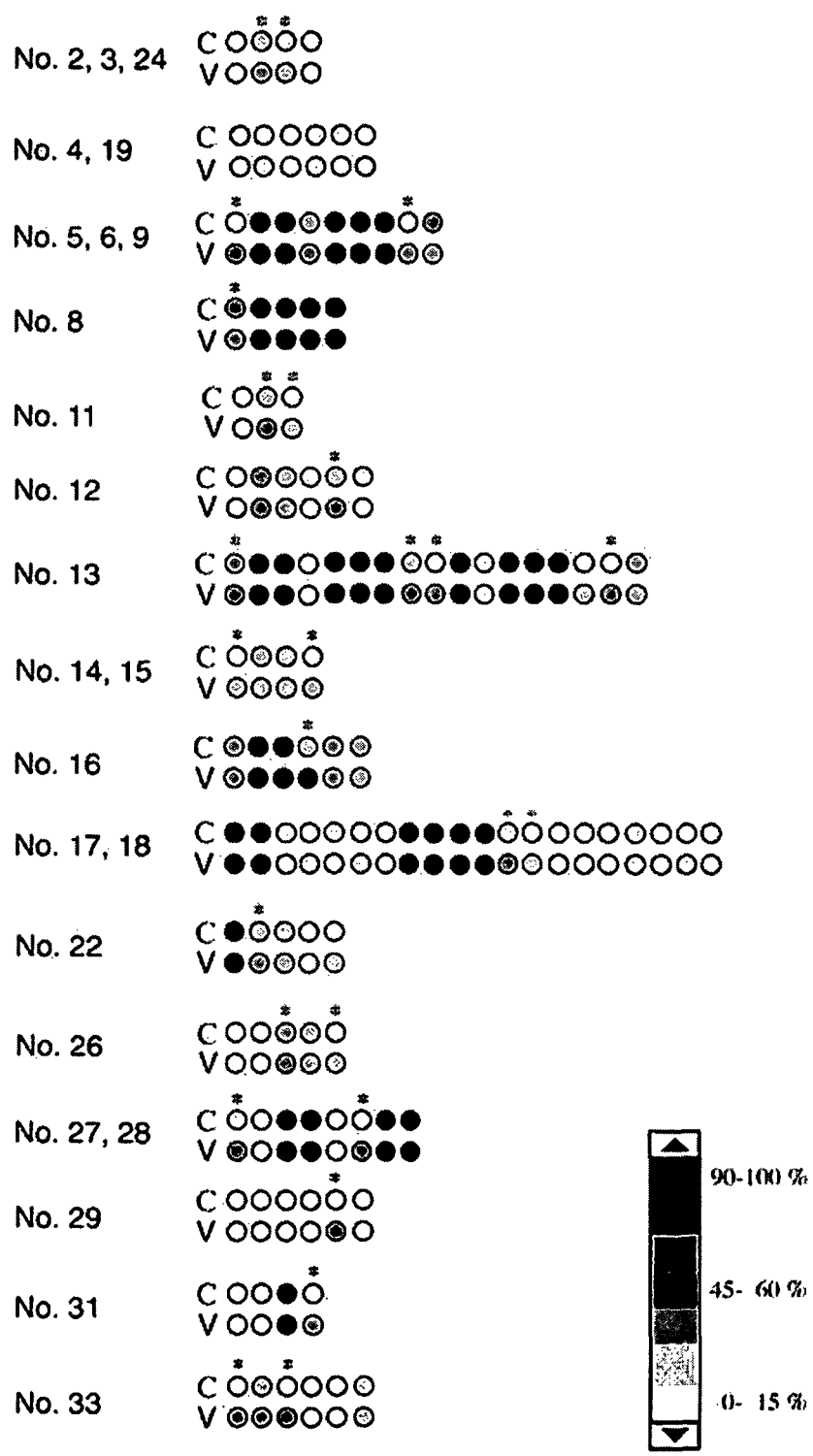
FIG. 12 shows a summary of altered methylation changes determined by bisulfite sequencing for each confirmed candidate. The percent methylation is presented as color in the circle for control or vinclozolin F2/F3 generation sperm DNA. The asterisks (*) denote statistically significant different methylation changes and each circle represents the specific CpG sites in the DNA sequence.

Verification that these candidates, Table 1, have specific alterations in DNA methylation required bisulfite sequencing analysis. Bisulfite converts cytosine (C) residues to thymine (T) residues unless the CpG is methylated at the 5' position on the cytosine, which inhibits the conversion. Specific bisulfite primers were used to amplify the bisulfite converted DNA followed by sequencing of individual clones to assess CpG sites for their methylation state. The bisulfite primers used for each candidate are listed in Table 2, and the analysis of each of the candidates is described below. Each candidate analysis involved a minimum of 3 different individual control and vinclozolin F2 and F3 animals with approximately 50 different sub-cloned DNA samples sequenced. The bisulfite analysis for each individual candidate containing a statistically significant change in methylation is shown in FIG. 10A-10Q. The chromosomal location of the methylation site and nearest genes are presented, along with the DNA sequence of the candidate site with potential methylated CpG sites underlined, and the asterisks (*) denote specific CpG with different methylation states between control and vinclozolin generation samples. The methylation analysis for all bisulfite sequence analysis for the different clones is represented as a closed circle for methylated and as an open circle for unmethylated CpG sites. Candidate #1 mapped to 8q23 and is in the exon/intron region of the recently annotated hypothetical gene LOC503205, similar to phosphoglycerate mutase chain B, with the nearest known gene being neural cell adhesion molecule 1 (NCAM1), FIG. 11A. Although 4 potential CpG sites exist, the high GC content of this DNA sequence prevents the design of specific bisulfite primers such that bisulfite methylation analysis was not possible, FIG. 11A. Candidate #2, 3, 24 mapped to 6q12 and is in a non-coding distal region with the nearest genes being leucine rich protein 157 (Lrpprc) and protein phosphatase 1B (Ppm1b), FIG. 10A. The bisulfite methylation analysis revealed 4 potential CpG and 2 are hypermethylated to 44% and 20%, FIG. 12 and FIG. 13. Candidate #4, 19 mapped to 13q21 and is in the intron of calcium channel, voltage-dependent L type α 1E subunit (Cacnale), FIG. 10B. The bisulfite methylation analysis revealed 6 potential CpG that did not have any detectable differences in methylation, FIG. 12 and FIG. 13. Candidate #5, 6, 9 mapped to 4q42 and is in the exon/intron to the uncharacterized gene FLJ22405 protein, FIG. 10C. The bisulfite methylation analysis revealed 9 potential CpG and 2 were hypermethylated to 50% and 35%, FIG. 12 and FIG. 13. Candidate #7 mapped to 16q16 and is in a non-coding region distal to ankyrin repeat protein 28 (Ankrd28) and polypeptide N-acetylgalactosaminyl transferase (Galnt12), FIG. 11B, and did not have any detectable differences after bisulfite analysis. Candidate #8 mapped to 1q42 and is in a non-coding region distal to liprin-α1 and Fas (TNFRSF6) associated via death domain (Fadd), FIG. 10D. The bisulfite methylation analysis revealed 5 potential CpG sites and one was hypermethylated to 65%, FIG. 12 and FIG. 13. Candidate #10 did not map to a specific chromosome and is uncharacterized, FIG. 9, so methylation with bisulfite analysis was not possible, FIG. 11C. Candidate #11 mapped to 4q24 and is in the non-coding region distal to 60S ribosomal protein L7a and uncharacterized RIKEN cDNA 1200009022, FIG. 10E. The bisulfite methylation analysis revealed 3 potential CpG and 2 were hypermethyylated to 49% and 21%, FIG. 12 and FIG. 13. Candidate #12 mapped to 14q11 and is in the promoter to the hypothetical gene similar to importin 7, LOC501910, FIG. 10F. The bisulfite methylation analysis revealed 6 potential CpG sites and one was hypermethylated to 51%, FIG. 12 and FIG. 13. Candidate #13 mapped to 19q11 and is in the intron to Nfix protein, FIG. 10G. The bisulfite methylation analysis revealed 17 potential CpG sites and 4 were hypermethylated to 50-60%, FIG. 12 and FIG. 13. Candidate #14, 15 mapped to 8q24 and is in the non-coding region distal to leucine rich repeat neuronal 6A (Lrrn6a), FIG. 10H. The bisulfite methylation analysis revealed 4 potential CpG and 2 were hypermethylated to 27%, FIG. 12 and FIG. 13. Candidate #16 mapped to 17q12 and is in the promoter/exon/intron of optineurin, FIG. 10I. The bisulfite methylation analysis revealed 6 potential CpG sites and one was hypermethylated to 79%, FIG. 12 and FIG. 13. Candidate #17, 18 mapped to 13q24 and is in the bi-directional promoter to nicastrin and coatomer protein complex subunit alpha, FIG. 10J. The bisulfite methylation analysis revealed 20 potential CpG sites and 2 were hypermethylated to 55% and 30%, FIG. 12 and FIG. 13. Candidate #20 did not map to a chromosome and is uncharacterized, FIG. 9, so methylation with bisulfite analysis was not possible, FIG. 11D. Candidate #21, 32 mapped to 8q23 and is in the exon/intron region of the recently annotated hypothetical gene similar to phosphoglycerate mutase B chain, LOC503205, FIG. 11E, with no differences in methylation after bisulfite analysis. The nearest known gene is neural cell adhesion molecule 1 (NCAM1). This potential methylation site is distinct from candidate No. 1, but in the same hypothetical gene. Candidate #22 mapped to 8q32 and is in the intron to tgolgin-1, FIG. 10K. The bisulfite methylation analysis revealed 5 potential CpG sites and one was hypermethylated to 67%, FIG. 12 and FIG. 13. Candidate #23 mapped to 7q22 and is in the non-coding region distal to a hypothetical gene similar to ribosomal protein, LOC503150, and U1 small nuclear ribonucleoprotein subunit (snRP1c), FIG. 11F, with no differences in methylation after bisulfite sequencing. Candidate #25 mapped to 5q24 and is in the non-coding region distal to major urinary protein (Mup4) and hypothetical gene major urinary precursor (MUP), LOC502951, FIG. 11G, with no differences in methylation detected with bisulfite analysis. However, the candidate 25 sequence is a repetitive sequence present in 12 different locations in chromosome 5q24. Potential methylation changes in the other locations remains to be investigated. Candidate #26 mapped to 10q26 and is in the promoter to acetyl-co-enzyme A carboxylase alpha (Acaca), FIG. 10L. The bisulfite methylation analysis revealed 5 potential CpG sites and 2 were hypermethylated to 50% and 28%, FIG. 12 and FIG. 13. Candidate #27, 28 mapped to 4q24 and is in the intron to zinc finger protein 212, FIG. 10M. The bisulfite methylation analysis revealed 8 potential CpG sites and 2 are hypermethylated to 45% and 48%, FIG. 12 and FIG. 13. Candidate #29 mapped to 11q11 and is in the non-coding region distal to Runx1 and similar to cell wall protein Awa1p (LOC501772), FIG. 10N. The bisulfite methylation analysis revealed 6 potential CpG sites and 1 was hypermethylated to 48%, FIG. 12 and FIG. 13. Candidate #30 did not map to a chromosome and is uncharacterized, FIG. 9, so methylation with bisulfite analysis was not possible, FIG. 11H. Candidate #31 mapped to 3q23 and is in the non-coding region distal to Wiskott-Aldrich syndrome protein interacting protein (Waspip) and hypothetical protein, LOC499811, FIG. 10O. The bisulfite methylation analysis revealed 4 potential CpG sites and one was hypermethylated to 42%, FIG. 12 and FIG. 13. Candidate #33 mapped to 6q12 and is in the non-coding region distal to sine oculis homeobox homolog 3 (Six3) and predicted Six2, FIG. 10P. The bisulfite methylation analysis revealed 6 potential CpG sites and 2 were hypermethylated to 31% and 57%, FIG. 12 and FIG. 13. Candidate #34 mapped to 9q37 and is in the promoter to the GTP-binding protein RAB12 and member of the Ras oncogene family, FIG. 11I. Due to the high GC content of this DNA sequence, bisulfite PCR primers could not be designed to analyze the entire sequence such that methylation analysis was not possible except for a partial region, which showed no change in methylation, FIG. 11I. Therefore, of the 25 candidate DNA sequences with altered methylation in vinclozolin generation sperm, 15 were confirmed to have specific hypermethylation, as summarized in FIG. 12 and FIG. 13. Six of the candidates were characterized, but no alterations in DNA methylation were detected, FIG. 12 and FIG. 13. Whether methylation occurred in the regions proximal to those analyzed can be confirmed with bisulfite analysis. Two candidates No. 1 (NCAM1/similar to phosphoglycerate mutase) and No. 34 (RAB12) could not be fully analyzed due to high GC content. As a control, a known imprinted gene H19 [151] was analyzed to determine if methylation changes were induced. No change in H19 methylation was detected between control and vinclozolin F2/F3 sperm DNA samples, FIG. 10Q.

Figure 14:
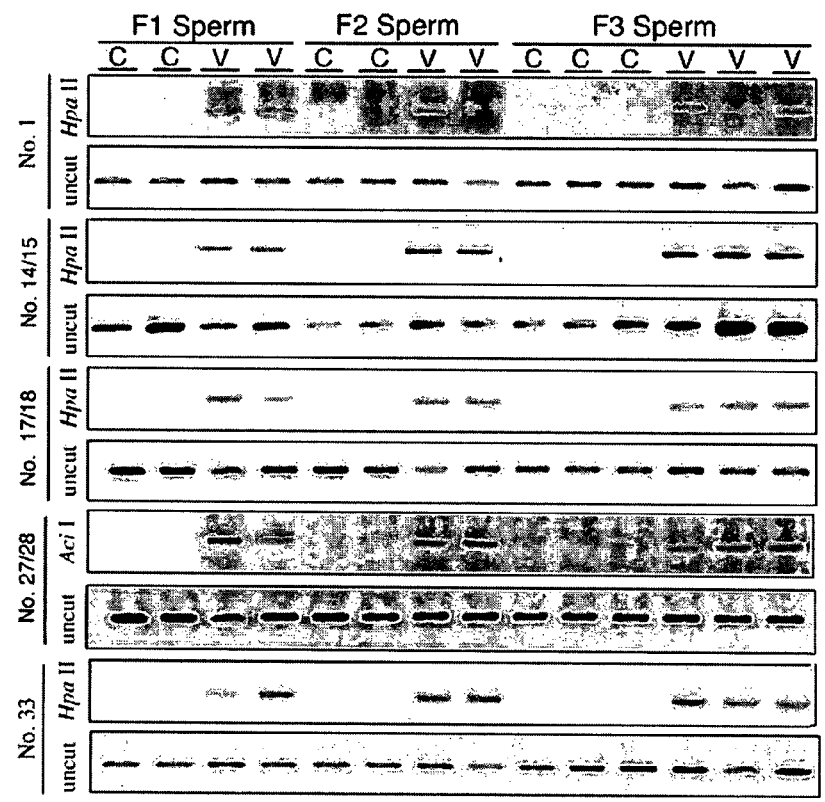
FIG. 14 shows DNA methylation states in epididymal sperms from control (C) and vinclozolin (V) F1, F2 and F3 generations using methylation sensitive (HpaII or Aci I) restriction enzyme PCR analysis. Candidates No 1, 14, 17, 27 and 33 digests are presented. The bands presented are representative of sperm DNA from different animals from each generation. PCR primers are provided in Table 2.

The control and vinclozolin generation sperm DNA, used in the initial MSRE-PCR, and in the bisulfite analysis, were from F2 and F3 generation males. Therefore, the epigenetic changes observed in the male germ-line appear transgenerational and permanently programmed into the sperm DNA. Methylation sensitive restriction enzyme analysis for specific candidate DNA sequences was developed, FIG. 14. The MSRE analysis involved gene specific PCR primers to the candidates to obtain a PCR product with the vinclozolin generation sperm DNA versus control. Analysis of sperm DNA from F1, F2 and F3 control and vinclozolin generation animals demonstrated candidates #1, #14, #17/18, #27/28, and #33 all show similar PCR results for F1-F3 sperm, FIG. 14. PCR products were observed in all the vinclozolin generation sperm DNA samples, but not in the controls. Therefore, the methylation changes identified are transgenerational, and appear imprinted-like in the male germ-line. Due to the variability in methylation shown in FIGS. 10 and 12, many of the candidates and DNA sequences analyzed could not be used to develop a specific MSRE analysis. One of the candidates (No. 33) did not have a consensus Hpa II digestion site, but did reproducibly digest the DNA (FIG. 14), and another candidate (No. 27/28) used an alternate methylation sensitive restriction enzyme Aci I.

These results demonstrate that the epigenetic changes in the male germ-line resulting from toxicant exposure, develop an imprinted-like characteristic and appear transgenerational.

The consequence of the epigenetic changes in the male germ-line induced by vinclozolin and present in subsequent generations, was investigated by examining the gene expression of the genes identified to be associated with the DNA methylation sites identified. Embryonic day 16 (E16) testes were isolated from control and vinclozolin F1 and F2 generation animals followed by RNA isolation and microarray analysis. The genes that were found to be expressed in the embryonic testis are shown in FIG. 15A-15C, and all others were either not present on the microarray chips or were below the detection limit demonstrating a lack of expression in the E16 testis. The gene expression profile between E13, E14 and E16 of testis development is presented in FIG. 15A. The E16, F1 and F2 controls are compared to the E16, F1 and F2 vinclozolin generation expression. A number of the genes had reduced expression in the vinclozolin F1 and F2 generation E16 testis, including ankyrin 28, Ncstn, Rab12, and Lrrn6a, FIG. 15A-15C.

The genes that had increased expression in the vinclozolin F1 and F2 generation E16 testis, compared to control, were Fadd, Pbm1b, Rps12 and Waspip, FIG. 15A. Therefore, the effects of the hypermethylation of the genes shown in FIGS. 10 and 12 caused both increases and decreases in gene expression in the developing embryonic testis. Analysis of the F3 generation will determine whether the changes in gene expression continue to be transgenerational.

The expression of one of the known genes nearest an altered methylation site identified candidate #1 (NCAM1), is primarily brain specific. An analysis of gene expression for NCAM in the brain was performed. Brains from adult control and vinclozolin F3 generation males were isolated, and RNA was prepared. Four control and five vinclozolin F3 generation animals were analyzed separately. A semi-quantitative PCR was developed for NCAM1, and demonstrated the NCAM1 mRNA levels were significantly reduced in vinclozolin generation animals, compared to controls, FIG. 15B. An internal constitutively expressed gene, ribosomal protein L19, demonstrated the integrity of the RNA and equal loading with control. This decreased expression of NCAM1 was quantitated, and over a 10-fold reduction in expression was observed between control and vinclozolin F3 generation males, FIG. 15C. Therefore, the hypermethylation of the candidate #1 site in sperm DNA was associated with a reduction in NCAM1 expression in the adult male brain, in vinclozolin F3 generation animals. Combined observations suggest the epigenetic alterations identified in the male germ-line appear to associate with alterations in gene expression in developing organs.

Figure 16:
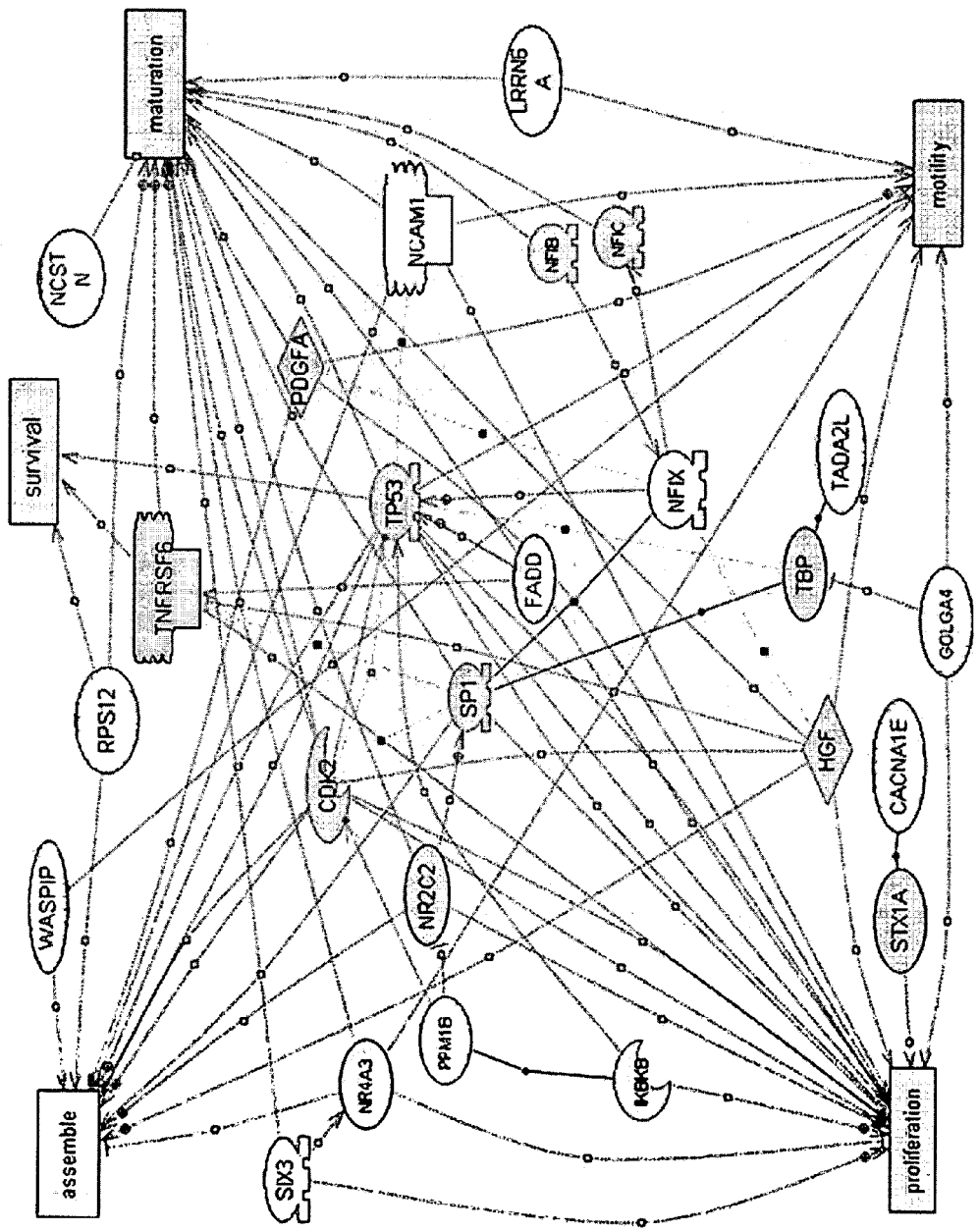
FIG. 16 shows pathway assist analysis of gene interactions with the candidates (open) and interacting genes (shaded) with cellular pathways (rectangles).

The specific genes associated with the epigenetic changes identified were examined for potential functional relationships. For the genes with known functions or homologs, a Pathway Assist bioinformatics program was used to identify functional links between the various genes, FIG. 16. A number of cellular functions and processes (e.g. proliferation, maturation, motility) are affected by the various genes, but no major clustering was observed between the different genes, FIG. 16.

A number of the genes associated with the methylation changes identified have a relationship with various disease states, Table 3. Interestingly, all of these genes have been shown to have an epigenetic component to the disease and/or gene identified, Table 3. Therefore, alterations in the epigenetic (DNA methylation) and/or expression of these genes is associated with a number of disease states. In addition to these correlations to previous literature, the vinclozolin generation animals develop a variety of disease states [153]. Vinclozolin (F1-F4) generation animals between 6-12 months of age develop a variety of disease states or abnormalities, Table 4 [153]. Therefore, the vinclozolin generational animals used develop a variety of diseases [153], and have the altered epigenetic programming of the male germ-line. Combined observations indicate that the epigenetic alterations in the germ-line DNA and associated genes identified in this Example, are associated with a number of disease states, Tables 3 and 4.

TABLE 3

Summaries of related diseases associated with the candidate genes.

| Candidate No. | Gene symbol | Related disease | Epigenetic Link | Reference |
|---|---|---|---|---|
| 1 | NCAM1 | Alzheimer<br>Synovial sarcoma<br>Schizophrenia<br>Mutant-Allele-Specific Amplification (MASA) syndrome<br>Neural tube defects<br>Various tumor | Yes | [153, 154, 155, 156, 157, 158] |
| 2, 3, 24 | Lrpprc | Nociceptor | Yes | [159] |
| 4, 19 | Cacna1e | Hyperglycemia<br>Arrhythmia<br>Familial hypokalemic periodic Paralysis<br>Male infertility | Yes | [160, 161, 162, 163] |
| 7 | Ankrd28 | Bare lymphocyte syndrome | Yes | [164] |
| 8 | Fadd | Cardiomycyte defect<br>Neimann-Pick type C disease | Yes | [165, 166] |
| 13 | Nfix | Hipocampal commissure detect | Yes | [167] |
| 16 | Optineurin | Open angle glaucoma | Yes | [168, 169] |
| 17, 18 | Nicastrin | Alzheimer | Yes | [170, 171, 172] |
| 21, 32 | Phosphoglycerate Mutase | Neuromuscular disorder | Yes | [173] |
| 23 | U1 snRNP | Systemic autoimmune diseases | Yes | [174, 175] |
| 25 | Mup4 | Renal Cysts | Yes | [176, 177] |
| 29 | Runx1 | Acute myeloid leukemia<br>Rheumatoid Arthritis<br>Myelodysplastic syndromes<br>Spenomegaly | Yes | [178] |
| 31 | Waspip | Wiskott-Aldrich syndrome | Yes | [179] |
| 33 | Six3 | Holoprosencephaly<br>Extraskeletal myxoid chondrosaromas | Yes | [180, 181, 182, 183] |

TABLE 4

Vinclozolin Inducted (F1–F4) Transgenerational Disease States

| Disease or Abnormality | Prevalence |
|---|---|
| Testis Defect | 30% |
| Prostate Disease | 50% |
| Kidney Disease | 40% |
| Tumor Development (e.g. breast) | 17% |
| Immune Abnormalities | 27% |

The results presented herein demonstrate that exposure to two different endocrine disruptors (i.e. anti-androgenic vinclozolin and estrogenic methoxychlor) at the time of gonadal sex determination, promotes adult onset disease for four (F1-F4) generations.

The ability to promote transgenerational disease states at the high frequencies observed cannot be explained by DNA sequence mutations. Hot spot DNA sequence mutations generally occur at less than 0.01% frequencies and decline with each generation [4, 184]. An epigenetic transgenerational mechanism would require the involvement of the germ-line. Interestingly, the primordial germ cell undergoes a de-methylation and re-methylation during gonadal sex determination [185, 186]. Therefore, an environmental factor such as the endocrine disruptor vinclozolin could alter gonadal development and influence the DNA methylation programming of the germ-line. These examples demonstrate that exposure to vinclozolin during embryonic gonadal sex determination promotes an epigenetic imprinting of the male germ-line (i.e. sperm) that is associated with the transgenerational disease phenotypes observed.

Methylation of DNA is a critical epigenetic factor in the regulation of gene expression [187], mammalian development [188] and disease (e.g. tumorgenesis) [10, 189, 1903]. Specific DNA methylation patterns can have a role in regulating the ability of promoter regions of genes to respond to transcriptional activator complexes and/or influence chromatin structures that influence gene expression [191]. Although the vast majority of genomic DNA methylation is "reset" after fertilization [185], a small subset of imprinted genes maintain a defined DNA methylation pattern that is transmitted through the male or female germ-line, resulting in allelic expression differences [192-194]. Imprinted genes are monoallelically expressed in a parent-of-origin manner and recently a bioinformatics approach has identified as many as 600 candidate imprinted genes in the mouse genome [146]. Although the specific monoallelic expression pattern was not directly determined for all the genes identified in the current study, the involvement of the paternal allele was determined by examining sperm from multiple generations. None of the rat genes identified or mouse homologs are on the 600 candidate mouse list reported [146], but species differences could be an issue. One of the genes identified Runx1 was on the non-imprinted gene list used [146]. The current Examples present the novel observation that an environmental factor can reprogram the germ-line to promote the presence of new imprinted-like genes/DNA sequences. These new imprinted-like genes/DNA sequences acquire an altered DNA methylation pattern that is transferred through the male germ-line (i.e. paternal allele) to subsequent generations (F1-F3). Observations suggest an epigenetic reprogramming of the germ-line is possible. The ability of an environmental factor to alter the transgenerational epigenetic background of an individual and all subsequent progeny has significant impacts on disease etiology.

The caudal epidiymal sperm from control and vinclozolin F1-F3 generation males were collected to elucidate potential differences in DNA methylation. The procedure used in the current Examples use a methylation sensitive restriction enzyme analysis (MSRE), followed by PCR, to identify alterations in DNA methylation. This analysis provided 25 different candidate DNA sequences with potential altered methylation. Other procedures involving methylation binding proteins and microarrays [195], have recently been developed, and are incorporated by reference herein. Analysis of the 25 candidates, demonstrated 15 had confirmed changes in DNA methylation patterns, and that these patterns were transgenerational (i.e. imprinted-like). The 10 genes/DNA sequences that were not confirmed, are believed to be "imprinted-like," due to the procedure involved in their isolation. Further analysis of flanking DNA sequences can identify the specific methylation changes. A number of the altered DNA methylation sites were in non-coding regions distal to the nearest genes. These sites may be involved in chromatin structural changes (e.g. positioning) that influence the distal genes. The NCAM1 expression is an example of this potential regulation.

The expression analysis of several of the genes associated with the candidate methylation sites demonstrated altered gene expression in the F1 and F2 vinclozolin generations embryonic testis. Analysis of one brain specific gene NCAM1 demonstrated a dramatic reduction in NCAM1 expression in the adult brain of vinclozolin generation males. Therefore, the impact of the transgenerational epigenetic imprinting on the male germ-line is an influence on the gene expression of relevant genes, in specific organs. The environmental compound vinclozolin (i.e. fungicide) can induce an epigenetic reprogramming of the male germ-line, and the new imprinted-like genes/DNA sequences, influence the expression of associated genes in relevant organs.

The genes associated with the altered DNA methylation sites range from cell adhesion molecules, ion channels, signaling factors such as phosphatases and GTP binding proteins, transcription factors, translational control factors and membrane proteins, Table 1. A bioinformatics pathway analysis demonstrated no major cluster or direct relationships between the various genes, but cellular processes such as proliferation, maturation (i.e. differentiation), motility, and assembly (i.e. structural) are affected by the genes identified. All the imprinted-like DNA sequences identified were hypermethylated compared to control generation sperm DNA. This hypermethylation suggests potential mechanisms involved in the imprinting mechanism, The current Examples identified the induction of imprinted-like genes/DNA sequences in the male germ-line transgenerationally. A number of the associated genes have been shown to be correlated to known disease (Table 2) including Alzheimers (Nicastrin) [153-158], polymodal nociceptor (Lrppc) [159], bare lymphocyte syndrome (Ankrd 28) [165, 166], hyperglycemia (cacnale) [160-163], open angle glaucoma (optineurin) [168, 169], acute myloid leukemia (Runx1) [178], Wiskott-Aldrich syndrome (Waspip) [179], and holoprogencephaly (Six3) [180, 182, 183]. Therefore, a number of the epigenetic changes identified were associated with genes previously shown to have epigenetic links to human disease. As an example, neural cell adhesion molecule 1 (NCAM1) is critical in neural tube and brain development and abnormalities in NCAM1 causes a number of brain diseases and abnormalities, including Alzheimer's [153-158]. Observations demonstrate a dramatic reduction in NCAM expression transgenerationally in the vinclozolin generation adult males. In addition, nicastrin interacts with the gamma-secretase complex and is critical for normal secretase membrane function [196]. The inhibition of nicastrin alters gamma-secretase cleavage activity and has been linked as a factor in Alzheimer's disease [197]. Epidemiological studies have indicated that Alzheimer's has a potential paternal transmission and paternal age is a risk factor for this disease [198]. Combined observations suggest that an environmental factor can induce an imprinted-like epigenetic change in two different genes associated with brain disease and Alzheimer's that transmit their epigenetics through the male germ-line (paternal allele) as a potential factor in the disease.

As shown in the Examples herein, embryonic exposure to vinclozolin during sex determination promotes the development of adult disease transgenerationally. These transgenerational diseases include male fertility abnormalities, tumor development, kidney disease, prostate disease and immune abnormalities [152]. The vinclozolin generation animals used in the current study to identify the epigenetic imprinting in the sperm DNA, develop disease states at approximately an 85% frequency. Therefore the imprinted-like genes/DNA sequences identified, are associated with these disease states. Further investigation of these imprinted-like genes/DNA sequences and correlation to various diseases will identify novel epigenetic diagnostic and therapeutic targets not previously considered.

Although epigenetics is associated with a number of diseases and abnormalities, the current major paradigm for disease etiology involves classic genetics and DNA sequence mutations as a major factor. Clearly regional differences in disease frequencies and environmental influences have suggested additional factors in the development of disease. The observations presented in the current Examples demonstrate that environmental compounds (endocrine disruptors) can induce a reprogramming in the epigenetic imprinting of the germ-line. The ability of an environmental factor to promote a permanent epigenetic change in the germ-line suggests an epigenetic component in disease etiology and a molecular mechanism for the ability of environmental factors to influence disease. This "transgenerational epigenetic mutagenesis" involves the ability of an environmental factor (e.g. endocrine disrupter) to influence embryonic development at the time of sex determination to epigenetically reprogram the germ-line through the induction of new imprinted-like genes/DNA sequences that then lead to epigenetic alterations in gene expression to promote disease states transgenerationally. Further analysis of this epigenetic disease etiology will provide novel epigenetic diagnostics and therapeutic targets to advance disease therapy. In addition to disease etiology, this transgenerational epigenetic mutagenesis also impacts basic developmental biology and broader areas of biology such as evolution.

REFERENCES

1. Tsui, M. T. and Wang, W. X., Maternal transfer efficiency and transgenerational toxicity of methylmercury in Daphnia magna *Environ Toxicol Chem*, 2004. 23(6): p. 1504-11.
2. Shimada, A. and Shima, A., Transgenerational genomic instability as revealed by a somatic mutation assay using the medaka fish *Mutat Res*, 2004. 552(1-2): p. 119-24.
3. Nomura, T., Nakajima, H., Ryo, H., Li, L. Y., Fukudome, Y., Adachi, S., Gotoh, H., and Tanaka, H., Transgenerational transmission of radiation- and chemically induced tumors and congenital anomalies in mice: studies of their possible relationship to induced chromosomal and molecular changes *Cytogenet Genome Res*, 2004. 104(1-4): p. 252-60.
4. Barber, R., Plumb, M. A., Boulton, E., Roux, I., and Dubrova, Y. E., Elevated mutation rates in the germ line of first- and second-generation offspring of irradiated male mice *Proc Natl Acad Sci USA*, 2002. 99(10): p. 6877-82.
5. Hoyes, K. P., Lord, B. I., McCann, C., Hendry, J. H., and Morris, I. D., Transgenerational effects of preconception paternal contamination with (55)Fe *Radiat Res*, 2001. 156(5 Pt 1): p. 488-94.
6. Mohr, U., Dasenbrock, C., Tillmann, T., Kohler, M., Kamino, K., Hagemann, G., Morawietz, G., Campo, E., Cazorla, M., Fernandez, P., Hernandez, L., Cardesa, A., and Tomatis, L., Possible carcinogenic effects of X-rays in a transgenerational study with CBA mice *Carcinogenesis*, 1999. 20(2): p. 325-32.
7. Dubrova, Y. E., Radiation-induced transgenerational instability *Oncogene*, 2003. 22(45): p. 7087-93.
8. Fujii, T., Transgenerational effects of maternal exposure to chemicals on the functional development of the brain in the offspring *Cancer Causes Control*, 1997. 8(3): p. 524-8.
9. Foran, C. M., Peterson, B. N., and Benson, W. H., Transgenerational and developmental exposure of Japanese medaka (*Oryzias latipes*) to ethinylestradiol results in endocrine and reproductive differences in the response to ethinylestradiol as adults *Toxicol Sci*, 2002. 68(2): p. 389-402.
10. Cheng, R. Y., Hockman, T., Crawford, E., Anderson, L. M., and Shiao, Y. H., Epigenetic and gene expression changes related to transgenerational carcinogenesis *Mol Carcinog*, 2004. 40(1): p. 1-11.
11. Martin, R. M., Smith, G. D., Frankel, S., and Gunnell, D., Parents' growth in childhood and the birth weight of their offspring *Epidemiology*, 2004. 15(3): p. 308-16.
12. Kang, I. J., Yokota, H., Oshima, Y., Tsuruda, Y., Oe, T., Imada, N., Tadokoro, H., and Honjo, T., Effects of bisphenol a on the reproduction of Japanese medaka (*Oryzias latipes*) *Environ Toxicol Chem*, 2002. 21(11): p. 2394-400.
13. Schwaiger, J., Mallow, U., Ferling, H., Knoerr, S., Braunbeck, T., Kalbfus, W., and Negele, R. D., How estrogenic is nonylphenol? A transgenerational study using rainbow trout (Oncorhynchus mykiss) as a test organism *Aquat Toxicol*, 2002. 59(3-4): p. 177-89.
14. Parks, L. G., Ostby, J. S., Lambright, C. R., Abbott, B. D., Klinefelter, G. R., Barlow, N. J., and Gray, L. E., Jr., The plasticizer diethylhexyl phthalate induces malformations by decreasing fetal testosterone synthesis during sexual differentiation in the male rat *Toxicol Sci*, 2000. 58(2): p. 339-49.
15. DeRosa, C., Richter, P., Pohl, H., and Jones, D. E., Environmental exposures that affect the endocrine system: public health implications *J Toxicol Environ Health B Crit Rev*, 1998. 1(1): p. 3-26.
16. Roemer, I., Reik, W., Dean, W., and Klose, J., Epigenetic inheritance in the mouse *Curr Biol*, 1997. 7(4): p. 277-80.
17. Rakyan, V. and Whitelaw, E., Transgenerational epigenetic inheritance *Curr Biol*, 2003. 13(1): p. R6.
18. Rakyan, V. K., Chong, S., Champ, M. E., Cuthbert, P. C., Morgan, H. D., Luu, K. V., and Whitelaw, E., Transgenerational inheritance of epigenetic states at the murine Axin (Fu) allele occurs after maternal and paternal transmission *Proc Natl Acad Sci USA*, 2003. 100(5): p. 2538-43.
19. Lane, N., Dean, W., Erhardt, S., Hajkova, P., Surani, A., Walter, J., and Reik, W., Resistance of IAPs to methylation reprogramming may provide a mechanism for epigenetic inheritance in the mouse *Genesis*, 2003. 35(2): p. 88-93.
20. Lee, J., Inoue, K., Ono, R., Ogonuki, N., Kohda, T., Kaneko-Ishino, T., Ogura, A., and Ishino, F., Erasing genomic imprinting memory in mouse clone embryos produced from day 11.5 primordial germ cells *Development*, 2002. 129(8): p. 1807-17.
21. Sato, S., Yoshimizu, T., Sato, E., and Matsui, Y., Erasure of methylation imprinting of Igf2r during mouse primordial germ-cell development *Mol Reprod Dev*, 2003. 65(1): p. 41-50.
22. Hajkova, P., Erhardt, S., Lane, N., Haaf, T., El-Maarri, O., Reik, W., Walter, J., and Surani, M. A., Epigenetic reprogramming in mouse primordial germ cells *Mech Dev*, 2002. 117(1-2): p. 15-23.
23. Durcova-Hills, G., Ainscough, J., and McLaren, A., Pluripotential stem cells derived from migrating primordial germ cells *Differentiation*, 2001. 68(4-5): p. 220-6.
24. Carlsen, E., Giwercman, A., Keiding, N., and Skakkebaek, N. E., Evidence for decreasing quality of semen during past 50 years *Bmj*, 1992. 305(6854): p. 609-13.
25. Sharpe, R. M., Fisher, J. S., Millar, M. M., Jobling, S., and Sumpter, J. P., Gestational and lactational exposure of rats 26. Facemire, C. F., Gross, T. S., and Guillette, L. J., Jr., Reproductive impairment in the Florida panther: nature or nurture? *Environ Health Perspect*, 1995. 103 Suppl 4: p. 79-86.
27. Kelce, W. R., Lambright, C. R., Gray, L. E., Jr., and Roberts, K. P., Vinclozolin and p,p'-DDE alter androgen-dependent gene expression: in vivo confirmation of an androgen receptor-mediated mechanism *Toxicol Appl Pharmacol*, 1997. 142(1): p. 192-200.
28. Cummings, A. M., Methoxychlor as a model for environmental estrogens *Crit Rev Toxicol*, 1997. 27(4): p. 367-79.
29. Pettersson, K. and Gustafsson, J. A., Role of estrogen receptor beta in estrogen action *Annu Rev Physiol*, 2001. 63: p. 165-92.
30. Lee, K. H., Hess, R. A., Bahr, J. M., Lubahn, D. B., Taylor, J., and Bunick, D., Estrogen receptor alpha has a functional role in the mouse rete testis and efferent ductules *Biol Reprod*, 2000. 63(6): p. 1873-80.
31. Brandenberger, A. W., Tee, M. K., Lee, J. Y., Chao, V., and Jaffe, R. B., Tissue distribution of estrogen receptors alpha (ER-alpha) and beta (ER-beta) mRNA in the midgestational human fetus *J Clin Endocrinol Metab*, 1997. 82(10): p. 3509-12.
32. Saunders, P. T., Maguire, S. M., Gaughan, J., and Millar, M. R., Expression of oestrogen receptor beta (ER beta) in multiple rat tissues visualised by immunohistochemistry *J Endocrinol*, 1997. 154(3): p. R13-6.
33. Goyal, H. O., Bartol, F. F., Wiley, A. A., Khalil, M. K., Chiu, J., and Vig, M. M., Immunolocalization of androgen receptor and estrogen receptor in the developing testis and excurrent ducts of goats *Anat Rec*, 1997. 249(1): p. 54-62.
34. Li, H., Papadopoulos, V., Vidic, B., Dym, M., and Culty, M., Regulation of rat testis gonocyte proliferation by platelet-derived growth factor and estradiol: identification of signaling mechanisms involved *Endocrinology*, 1997. 138(3): p. 1289-98.
35. Eddy, E. M., Washburn, T. F., Bunch, D. O., Goulding, E. H., Gladen, B. C., Lubahn, D. B., and Korach, K. S., Targeted disruption of the estrogen receptor gene in male mice causes alteration of spermatogenesis and infertility *Endocrinology*, 1996. 137(11): p. 4796-805.
36. Smith, E. P., Boyd, J., Frank, G. R., Takahashi, H., Cohen, R. M., Specker, B., Williams, T. C., Lubahn, D. B., and Korach, K. S., Estrogen resistance caused by a mutation in the estrogen-receptor gene in a man *N Engl J Med*, 1994. 331(16): p. 1056-61.
37. Couse, J. F., Hewitt, S. C., Bunch, D. O., Sar, M., Walker, V. R., Davis, B. J., and Korach, K. S., Postnatal sex reversal of the ovaries in mice lacking estrogen receptors alpha and beta *Science*, 1999. 286(5448): p. 2328-31.
38. Tena-Sempere, M., Navarro, J., Pinilla, L., Gonzalez, L. C., Huhtaniemi, I., and Aguilar, E., Neonatal exposure to estrogen differentially alters estrogen receptor alpha and beta mRNA expression in rat testis during postnatal development *J Endocrinol*, 2000. 165(2): p. 345-57.
39. Tena-Sempere, M., Gonzalez, L. C., Pinilla, L., Huhtaniemi, I., and Aguilar, E., Neonatal imprinting and regulation of estrogen receptor alpha and beta mRNA expression by estrogen in the pituitary and hypothalamus of the male rat *Neuroendocrinology*, 2001. 73(1): p. 12-25.
40. Atanassova, N., McKinnell, C., Walker, M., Turner, K. J., Fisher, J. S., Morley, M., Millar, M. R., Groome, N. P., and Sharpe, R. M., Permanent effects of neonatal estrogen exposure in rats on reproductive hormone levels, Sertoli cell number, and the efficiency of spermatogenesis in adulthood *Endocrinology*, 1999. 140(11): p. 5364-73.
41. Nielsen, M., Bjornsdottir, S., Hoyer, P. E., and Byskov, A. G., Ontogeny of oestrogen receptor alpha in gonads and sex ducts of fetal and newborn mice *J Reprod Fertil*, 2000. 118(1): p. 195-204.
42. Ebling, F. J., Brooks, A. N., Cronin, A. S., Ford, H., and Kerr, J. B., Estrogenic induction of spermatogenesis in the hypogonadal mouse *Endocrinology*, 2000. 141(8): p. 2861-9.
43. Prins, G. S. and Birch, L., The developmental pattern of androgen receptor expression in rat prostate lobes is altered after neonatal exposure to estrogen *Endocrinology*, 1995. 136(3): p. 1303-14.
44. McKinnell, C., Atanassova, N., Williams, K., Fisher, J. S., Walker, M., Turner, K. J., Saunders, T. K., and Sharpe, R. M., Suppression of androgen action and the induction of gross abnormalities of the reproductive tract in male rats treated neonatally with diethylstilbestrol *J Androl*, 2001. 22(2): p. 323-38.
45. Wilson, C. M. and McPhaul, M. J., A and B forms of the androgen receptor are expressed in a variety of human tissues *Mol Cell Endocrinol*, 1996. 120(1): p. 51-7.
46. Majdic, G., Millar, M. R., and Saunders, P. T., Immunolocalisation of androgen receptor to interstitial cells in fetal rat testes and to mesenchymal and epithelial cells of associated ducts *J Endocrinol*, 1995. 147(2): p. 285-93.
47. Silversides, D. W., Price, C. A., and Cooke, G. M., Effects of short-term exposure to hydroxyflutamide in utero on the development of the reproductive tract in male mice *Can J Physiol Pharmacol*, 1995. 73(11): p. 1582-8.
48. Nambu, A. and Kumamoto, Y., [Studies of spermatogenic damages induced by anti-cancer agent and anti-androgenic agents in rat testes] *Nippon Hinyokika Gakkai Zasshi*, 1995. 86(7): p. 1221-30.
49. Gupta, C., Chandorkar, A., and Nguyen, A. P., Activation of androgen receptor in epidermal growth factor modulation of fetal mouse sexual differentiation *Mol Cell Endocrinol*, 1996. 123(1): p. 89-95.
50. Turner, K. J., Barlow, N. J., Struve, M. F., Wallace, D. G., Gaido, K. W., Dorman, D. C., and Foster, P. M., Effects of in utero exposure to the organophosphate insecticide fenitrothion on androgen-dependent reproductive development in the Crl: CD(SD)BR rat *Toxicol Sci*, 2002. 68(1): p. 174-83.
51. Hotchkiss, A. K., Ostby, J. S., Vandenburgh, J. G., and Gray, L. E., Jr., Androgens and environmental antiandrogens affect reproductive development and play behavior in the Sprague-Dawley rat *Environ Health Perspect*, 2002. 110 Suppl 3: p. 435-9.
52. Kapoor, I. P., Metcalf, R. L., Nystrom, R. F., and Sangha, G. K., Comparative metabolism of methoxychlor, methiochlor, and DDT in mouse, insects, and in a model ecosystem *J Agric Food Chem*, 1970. 18(6): p. 1145-52.
53. Dehal, S. S. and Kupfer, D., Metabolism of the proestrogenic pesticide methoxychlor by hepatic P450 monooxygenases in rats and humans. Dual pathways involving novel ortho ring-hydroxylation by CYP2B *Drug Metab Dispos*, 1994. 22(6): p. 937-46.
54. Kupfer, D., Bulger, W. H., and Theoharides, A. D., Metabolism of methoxychlor by hepatic P-450 monooxygenases in rat and human. 1. Characterization of a novel catechol metabolite *Chem Res Toxicol*, 1990. 3(1): p. 8-16.
55. Bulger, W. H. and Kupfer, D., *Estrogenic activity of pesticides and other xenobiotic on the uterus and male repro-*

*ductive tract.*, in *Endocrine Toxicology*, J. A. Thomas, K. S. Korach, and J. A. McLachlan, Editors. 1985, Raven Press: New York. p. 1-33.
56. Lamoureux, C. H. and Feil, V. J., Gas chromatographic and mass spectrometric characterization of impurities in technical methoxychlor. *Anal. Chem.*, 1980. 63: p. 1007-1037.
57. West, P. R., Chaudhary, S. K., Branton, G. R., and Mitchell, R. H., High performance liquid chromatographic analysis of impurities and degradation products of methoxychlor. *Anal. Chem.*, 1982. 65: p. 1457-1470.
58. Eroschenko, V. P., Rourke, A. W., and Sims, W. F., Estradiol or methoxychbor stimulates estrogen receptor (ER) expression in uteri *Reprod Toxicol*, 1996. 10(4): p. 265-71.
59. Gaido, K. W., Leonard, L. S., Maness, S. C., Hall, J. M., McDonnell, D. P., Saville, B., and Safe, S., Differential interaction of the methoxychlor metabolite 2,2-bis-(p-hydroxyphenyl)-1,1,1-trichloroethane with estrogen receptors alpha and beta *Endocrinology*, 1999. 140(12): p. 5746-53.
60. Gaido, K. W., Maness, S. C., McDonnell, D. P., Dehal, S. S., Kupfer, D., and Safe, S., Interaction of methoxychlor and related compounds with estrogen receptor alpha and beta, and androgen receptor: structure-activity studies *Mol Pharmacol*, 2000. 58(4): p. 852-8.
61. Matthews, J., Celius, T., Halgren, R., and Zacharewski, T., Differential estrogen receptor binding of estrogenic substances: a species comparison *J Steroid Biochem Mol Biol*, 2000. 74(4): p. 223-34.
62. Chapin, R. E., Harris, M. W., Davis, B. J., Ward, S. M., Wilson, R. E., Mauney, M. A., Lockhart, A. C., Smialowicz, R. J., Moser, V. C., Burka, L. T., and Collins, B. J., The effects of perinatal/juvenile methoxychlor exposure on adult rat nervous, immune, and reproductive system function *Fundam Appl Toxicol*, 1997. 40(1): p. 138-57.
63. Cooke, P. S. and Eroschenko, V. P., Inhibitory effects of technical grade methoxychlor on development of neonatal male mouse reproductive organs *Biol Reprod*, 1990. 42(3): p. 585-96.
64. Suzuki, M., Lee, H. C., Chiba, S., Yonezawa, T., and Nishihara, M., Effects of methoxychlor exposure during perinatal period on reproductive function after maturation in rats *J Reprod Dev*, 2004. 50(4): p. 455-61.
65. Swartz, W. J. and Eroschenko, V. P., Neonatal exposure to technical methoxychlor alters pregnancy outcome in female mice *Reprod Toxicol*, 1998. 12(6): p. 565-73.
66. Alworth, L. C., Howdeshell, K. L., Ruhlen, R. L., Day, J. K., Lubahn, D. B., Huang, T. H., Besch-Williford, C. L., and vom Saal, F. S., Uterine responsiveness to estradiol and DNA methylation are altered by fetal exposure to diethylstilbestrol and methoxychlor in CD-1 mice: effects of low versus high doses *Toxicol Appl Pharmacol*, 2002. 183(1): p. 10-22.
67. Eroschenko, V. P., Abuel-Atta, A. A., and Grober, M. S., Neonatal exposures to technical methoxychlor alters ovaries in adult mice *Reprod Toxicol*, 1995. 9(4): p. 379-87.
68. Borgeest, C., Symonds, D., Mayer, L. P., Hoyer, P. B., and Flaws, J. A., Methoxychlor may cause ovarian follicular atresia and proliferation of the ovarian epithelium in the mouse *Toxicol Sci*, 2002. 68(2): p. 473-8.
69. Palanza, P., Morellini, F., Parmigiani, S., and vom Saal, F. S., Prenatal exposure to endocrine disrupting chemicals: effects on behavioral development *Neurosci Biobehav Rev*, 1999. 23(7): p. 1011-27.
70. Stoker, T. E., Robinette, C. L., and Cooper, R. L., Perinatal exposure to estrogenic compounds and the subsequent effects on the prostate of the adult rat: evaluation of inflammation in the ventral and lateral lobes *Reprod Toxicol*, 1999. 13(6): p. 463-72.
71. Takeuchi, Y., Kosaka, T., Hayashi, K., Takeda, M., Yoshida, T., Fujisawa, H., Teramoto, S., Maita, K., and Harada, T., Thymic atrophy induced by methoxychlor in rat pups *Toxicol Lett*, 2002. 135(3): p. 199-207.
72. Latchoumycandane, C. and Mathur, P. P., Effect of methoxychlor on the antioxidant system in mitochondrial and microsome-rich fractions of rat testis *Toxicology*, 2002. 176(1-2): p. 67-75.
73. Swartz, W. J. and Corkem, M., Effects of methoxychlor treatment of pregnant mice on female offspring of the treated and subsequent pregnancies *Reprod Toxicol*, 1992. 6(5): p. 431-7.
74. Pothuluri, J. V., Freeman, J. P., Heinze, T. M., Beger, R. D., and Cerniglia, C. E., Biotransformation of vinclozolin by the fungus *Cunninghamella elegans J Agric Food Chem*, 2000. 48(12): p. 6138-48.
75. Kelce, W. R., Monosson, E., Gamcsik, M. P., Laws, S. C., and Gray, L. E., Jr., Environmental hormone disruptors: evidence that vinclozolin developmental toxicity is mediated by antiandrogenic metabolites *Toxicol Appl Pharmacol*, 1994. 126(2): p. 276-85.
76. Kelce, W. R., Gray, L. E., and Wilson, E. M., Antiandrogens as environmental endocrine disruptors *Reprod Fertil Dev*, 1998. 10(1): p. 105-11.
77. Gray, L. E., Jr., Ostby, J., Monosson, E., and Kelce, W. R., Environmental antiandrogens: low doses of the fungicide vinclozolin alter sexual differentiation of the male rat *Toxicol Ind Health*, 1999. 15(1-2): p. 48-64.
78. Monosson, E., Kelce, W. R., Lambright, C., Ostby, J., and Gray, L. E., Jr., Peripubertal exposure to the antiandrogenic fungicide, vinclozolin, delays puberty, inhibits the development of androgen-dependent tissues, and alters androgen receptor function in the male rat *Toxicol Ind Health*, 1999. 15(1-2): p. 65-79.
79. Yu, W. J., Lee, B. J., Nam, S. Y., Ahn, B., Hong, J. T., Do, J. C., Kim, Y. C., Lee, Y. S., and Yun, Y. W., Reproductive disorders in pubertal and adult phase of the male rats exposed to vinclozolin during puberty *J Vet Med Sci*, 2004. 66(7): p. 847-53.
80. Gray, L. E., Jr., Wolf, C., Lambright, C., Mann, P., Price, M., Cooper, R. L., and Ostby, J., Administration of potentially antiandrogenic pesticides (procymidone, linuron, iprodione, chlozolinate, p,p'-DDE, and ketoconazole) and toxic substances (dibutyl- and diethylhexyl phthalate, PCB 169, and ethane dimethane sulphonate) during sexual differentiation produces diverse profiles of reproductive malformations in the male rat *Toxicol Ind Health*, 1999. 15(1-2): p. 94-118.
81. Hellwig, J., van Ravenzwaay, B., Mayer, M., and Gembardt, C., Pre- and postnatal oral toxicity of vinclozolin in Wistar and Long-Evans rats *Regul Toxicol Pharmacol*, 2000. 32(1): p. 42-50.
82. Moorman, W. J., Cheever, K. L., Skaggs, S. R., Clark, J. C., Turner, T. W., Marlow, K. L., and Schrader, S. M., Male adolescent exposure to endocrine-disrupting pesticides: vinclozolin exposure in peripubertal rabbits *Andrologia*, 2000. 32(4-5): p. 285-93.
83. Shono, T., Suita, S., Kai, H., and Yamaguchi, Y., The effect of a prenatal androgen disruptor, vinclozolin, on gubemacular migration and testicular descent in rats *J Pediatr Surg*, 2004. 39(2): p. 213-6.

84. Wolf, C. J., LeBlanc, G. A., Ostby, J. S., and Gray, L. E., Jr., Characterization of the period of sensitivity of fetal male sexual development to vinclozolin *Toxicol Sci*, 2000. 55(1): p. 152-61.

85. Kelce, W. R., Stone, C. R., Laws, S. C., Gray, L. E., Kemppainen, J. A., and Wilson, E. M., Persistent DDT metabolite p, p'-DDE is a potent androgen receptor antagonist *Nature*, 1995. 375(6532): p. 581-5.

86. Wolf, C. J., LeBlanc, G. A., and Gray, L. E., Jr., Interactive effects of vinclozolin and testosterone propionate on pregnancy and sexual differentiation of the male and female SD rat *Toxicol Sci*, 2004. 78(1): p. 135-43.

87. Sertoli, E., On the existence of special branched cells in the seminiferous tubule of the human testes. *Morgangni*, 1865. 7: p. 31-39.

88. Fawcett, D. W., *The ultrastructure and functions of the Sertoli cell.*, in Handbook of Physiology, R. O. Greep and E. W. Hamilton, Editors. 1975, Am Physiol Soc: Washington D.C. p. 22-55.

89. Setchell, B. P. and Waites, G. M. H., *Handbook of Physiology*, R. O. Greep and E. W. Hamilton, Editors. 1975, Am Physiol Soc: Washington D.C. p. 143-172.

90. Waites, G. M. and Gladwell, R. T., Physiological significance of fluid secretion in the testis and blood-testis barrier *Physiol Rev*, 1982. 62(2): p. 624-71.

91. Russell, L. D., Tallon-Doran, M., Weber, J. E., Wong, V., and Peterson, R. N., Three-dimensional reconstruction of a rat stage V Sertoli cell: III. A study of specific cellular relationships *Am J Anat*, 1983. 167(2): p. 181-92.

92. Dorrington, J. H., Fritz, I. B., and Armstrong, D. T., Control of testicular estrogen synthesis *Biol Reprod*, 1978. 18(1): p. 55-64.

93. Robinson, R. and Fritz, I. B., Metabolism of glucose by Sertoli cells in culture *Biol Reprod*, 1981. 24(5): p. 1032-41.

94. Lacroix, M., Smith, F. E., and Fritz, I. B., Secretion of plasminogen activator by Sertoli cell enriched cultures *Mol Cell Endocrinol*, 1977. 9(2): p. 227-36.

95. Skinner, M. K. and Griswold, M. D., Sertoli cells synthesize and secrete a ceruloplasmin-like protein *Biol Reprod*, 1983. 28(5): p. 1225-9.

96. Skinner, M. K. and Griswold, M. D., Sertoli cells synthesize and secrete transferrin-like protein *J Biol Chem*, 1980. 255(20): p. 9523-5.

97. Griswold, M. D., Protein secretions of Sertoli cells *Int Rev Cytol*, 1988. 110'-p. 133-56.

98. Tung, P. S., Skinner, M. K., and Fritz, I. B., Fibronectin synthesis is a marker for peritubular cell contaminants in Sertoli cell-enriched cultures *Biol Reprod*, 1984. 30(1): p. 199-211.

99. Skinner, M. K., Cosand, W. L., and Griswold, M. D., Purification and characterization of testicular transferrin secreted by rat Sertoli cells *Biochem J*, 1984. 218(2): p. 313-20.

100. Skinner, M. K., Cell-cell interactions in the testis *Endocr Rev*, 1991. 12(1): p. 45-77.

101. Akingbemi, B. T., Ge, R. S., Klinefelter, G. R., Gunsalus, G. L., and Hardy, M. P., A metabolite of methoxychlor, 2,2-bis(p-hydroxyphenyl)-1,1,1-trichloroethane, reduces testosterone biosynthesis in rat leydig cells through suppression of steady-state messenger ribonucleic acid levels of the cholesterol side-chain cleavage enzyme *Biol Reprod*, 2000. 62(3): p. 571-8.

102. Kierszenbaum, A. L., Mammalian spermatogenesis in vivo and in vitro: a partnership of spermatogenic and somatic cell lineages *Endocr Rev*, 1994. 15(1): p. 116-34.

103. Jost, A., Magre, S., and Agelopoulou, R., Early stages of testicular differentiation in the rat *Hum Genet*, 1981. 58(1): p. 59-63.

104. Magre, S. and Jost, A., The initial phases of testicular organogenesis in the rat. An electron microscopy study *Arch Anat Microsc Morphol Exp*, 1980. 69(4): p. 297-318.

105. Buehr, M., Gu, S., and McLaren, A., Mesonephric contribution to testis differentiation in the fetal mouse *Development*, 1993. 117(1): p. 273-81.

106. McLaren, A., Development of the mammalian gonad: the fate of the supporting cell lineage *Bioessays*, 1991. 13(4): p. 151-6.

107. Frojdman, K., Paranko, J., Virtanen, I., and Pelliniemi, L. J., Intermediate filaments and epithelial differentiation of male rat embryonic gonad *Differentiation*, 1992. 50(2): p. 113-23.

108. Fridmacher, V., Le Bert, M., Guillou, F., and Magre, S., Switch in the expression of the K19/K18 keratin genes as a very early evidence of testicular differentiation in the rat *Mech Dev*, 1995. 52(2-3): p. 199-207.

109. Blanchard, M. G. and Josso, N., Source of the anti-Mullerian hormone synthesized by the fetal testis: Mullerian-inhibiting activity of fetal bovine Sertoli cells in tissue culture *Pediatr Res*, 1974. 8(12): p. 968-71.

110. Greene, R. R., Embyology of sexual structure and hermaphroditism. *J. Clinical Endorcrinology*, 1944. 4: p. 335-348.

111. Magre, S. and Jost, A., Sertoli cells and testicular differentiation in the rat fetus *J Electron Microsc Tech*, 1991. 19(2): p. 172-88.

112. Orth, J. M., Weisz, J., Ward, O. B., and Ward, I. L., Environmental stress alters the developmental pattern of delta 5-3 beta-hydroxysteroid dehydrogenase activity in Leydig cells of fetal rats: a quantitative cytochemical study *Biol Reprod*, 1983. 28(3): p. 625-31.

113. Bloch, E., Lew, M., and Klein, M., Studies on the inhibition of fetal androgen formation. Inhibition of testosterone synthesis in rat and rabbit fetal testes with observations on reproductive tract development *Endocrinology*, 1971. 89(1): p. 16-31.

114. Gupta, C., The role of epidermal growth factor receptor (EGFR) in male reproductive tract differentiation: stimulation of EGFR expression and inhibition of Wolffian duct differentiation with anti-EGFR antibody *Endocrinology*, 1996. 137(3): p. 905-10.

115. Gupta, C., Siegel, S., and Ellis, D., The role of EGF in testosterone-induced reproductive tract differentiation *Dev Biol*, 1991. 146(1): p. 106-16.

116. Levine, E., Cupp, A. S., Miyashiro, L., and Skinner, M. K., Role of transforming growth factor-alpha and the epidermal growth factor receptor in embryonic rat testis development *Biol Reprod*, 2000. 62(3): p. 477-90.

117. Desai, K. V. and Kondaiah, P., Androgen ablation results in differential regulation of transforming growth factor-beta isoforms in rat male accessory sex organs and epididymis *J Mol Endocrinol*, 2000. 24(2): p. 253-60.

118. Levine, E., Cupp, A. S., and Skinner, M. K., Role of neurotropins in rat embryonic testis morphogenesis (cord formation) *Biol Reprod*, 2000. 62(1): p. 132-42.

119. Cupp, A. S., Tessarollo, L., and Skinner, M. K., Testis developmental phenotypes in neurotropin receptor trkA and trkc null mutations: role in formation of seminiferous cords and germ cell survival *Biol Reprod*, 2002. 66(6): p. 1838-45.

120. Cupp, A. S. and Skinner, M. K., Actions of the endocrine disruptor methoxychlor and its estrogenic metabolite on in 120. vitro embryonic rat seminiferous cord formation and perinatal testis growth *Reprod Toxicol,* 2001. 15(3): p. 317-326.
121. Uzumcu, M., Suzuki, H., and Skinner, M. K., Effect of the Anti-Androgenic Endocrine Disruptor Vinclozolin on Embryonic Testis Cord Formation and Postnatal Testis Development and Function *Reproductive Toxicology,* 2004 18: (765-774).
122. Fisher, J. S., Environmental anti-androgens and male reproductive health: focus on phthalates and testicular dysgenesis syndrome *Reproduction,* 2004. 127(3): p. 305-15.
123. Cupp, A. S., Uzumcu, M., Suzuki, H., Dirks, K., Phillips, B., and Skinner, M. K., Effect of transient embryonic in vivo exposure to the endocrine disruptor methoxychlor on embryonic and postnatal testis development *J Androl,* 2003. 24(5): p. 736-45.
124. Chen, D., Yan, Z., Cole, D. L., and Srivatsa, G. S., Analysis of internal (n-1)mer deletion sequences in synthetic oligodeoxyribonucleotides by hybridization to an immobilized probe array *Nucleic Acids Res,* 1999. 27(2): p. 389-95.
125. Christianini, N. and Shawe-Taylor, J., *An Introduction to Support Vector Machines and Other Kernel-Based Learning Methods.* 2000, Cambridge, UK: Cambridge University Press.
126. Frommer, M., McDonald, L. E., Millar, D. S., Collis, C. M., Watt, F., Grigg, G. W., Molloy, P. L., and Paul, C. L., A genomic sequencing protocol that yields a positive display of 5-methylcytosine residues in individual DNA strands *Proc Natl Acad Sci USA,* 1992. 89(5): p. 1827-31.
127. Kvist, U. and Bjomdah., L., *Manual on Basic Semen Analysis.* Rev. ed. ed. ESHRE monographs. 2002, Germany: ESHRE and Oxford University Press. 14-17.
128. Taylor, G. T., Weiss, J., Frechmann, T., and Haller, J., Copulation induces an acute increase in epididymal sperm numbers in rats *J Reprod Fertil,* 1985. 73(2): p. 323-7.
129. Zhong, C. X. and Mass, M. J., Both hypomethylation and hypermethylation of DNA associated with arsenite exposure in cultures of human cells identified by methylation-sensitive arbitrarily-primed PCR *Toxicol Lett,* 2001. 122 (3): p. 223-34.
130. Liang, G., Salem, C. E., Yu, M. C., Nguyen, H. D., Gonzales, F. A., Nguyen, T. T., Nichols, P. W., and Jones, P. A., DNA methylation differences associated with tumor tissues identified by genome scanning analysis *Genomics,* 1998. 53(3): p. 260-8.
131. Gonzalgo, M. L., Liang, G., Spruck, C. H., 3rd, Zingg, J. M., Rideout, W. M., 3rd, and Jones, P. A., Identification and characterization of differentially methylated regions of genomic DNA by methylation-sensitive arbitrarily primed PCR *Cancer Res,* 1997. 57(4): p. 594-9.
132. Olek, A., Oswald, J., and Walter, J., A modified and improved method for bisulphite based cytosine methylation analysis *Nucleic Acids Res,* 1996. 24(24): p. 5064-6.
133. Clark, S. J. and Frommer, M., *Bisulphite genomic sequencing of methylated cytosines.,* in *Laboratory Methods for the Detection of Mutations and Polymorphisms in DNA.,* G. R. Taylor, Editor. 1997, CRC Press: Boca Raton, Fla. p. 151-161.
134. Tokumura, A., Metabolic pathways and physiological and pathological significances of lysolipid phosphate mediators *J Cell Biochem,* 2004. 92(5): p. 869-81.
135. Akingbemi, B. T., and Hardy, M. P. (2001). Oestrogenic and antiandrogenic chemicals in the environment: effects on male reproductive health. Ann Med 33, 391-403.
136. Brucker-Davis, F., Pointis, G., Chevallier, D., and Fenichel, P. (2003). Update on cryptorchidism: endocrine, environmental and therapeutic aspects. J Endocrinol Invest 26, 575-587.
137. Nicolopoulou-Stamati, P., and Pitsos, M. A. (2001). The impact of endocrine disrupters on the female reproductive system. Hum Reprod Update 7, 323-330.
138. Takeuchi, T., Tsutsumi, O., Ikezuki, Y., Takai, Y., and Taketani, Y. (2004). Positive relationship between androgen and the endocrine disruptor, bisphenol A, in normal women and women with ovarian dysfunction. Endocr J 51, 165-169.
139. Pembrey, M. E., Bygren, L. O., Kaati, G., Edvinsson, S., Northstone, K., Sjostrom, M., and Golding, J. (2006). Sex-specific, male-line transgenerational responses in humans. Eur J Hum Genet 14, 159-166.
140. Zambrano, E., Martinez-Samayoa, P. M., Bautista, C. J., Deas, M., Guillen, L., Rodriguez-Gonzalez, G. L., Guzman, C., Larrea, F., and Nathanielsz, P. W. (2005). Sex differences in transgenerational alterations of growth and metabolism in progeny (F2) of female offspring (F1) of rats fed a low protein diet during pregnancy and lactation. J Physiol 566, 225-236.
141. Gluckman, P. D., and Hanson, M. A. (2004). Developmental origins of disease paradigm: a mechanistic and evolutionary perspective. Pediatr Res 56, 311-317.
142. Heindel, J. J. (2005). The fetal basis of adult disease: Role of environmental exposures—introduction. Birth Defects Res A Clin Mol Teratol 73, 131-132.
143. Clayton-Smith, J., and Laan, L. (2003). Angelman syndrome: a review of the clinical and genetic aspects. J Med Genet 40, 87-95.
144. Jiang, Y. H., Bressler, J., and Beaudet, A. L. (2004). Epigenetics and human disease. Annu Rev Genomics Hum Genet 5, 479-510.
145. Weksberg, R., Shuman, C., and Smith, A. C. (2005). Beckwith-Wiedemann syndrome. Am J Med Genet C Semin Med Genet 137, 12-23.
146. Luedi, P. P., Hartemink, A. J., and Jirtle, R. L. (2005). Genome-wide prediction of imprinted murine genes. Genome Res 15, 875-884.
147. Lucifero, D., Chaillet, J. R., and Trasler, J. M. (2004). Potential significance of genomic imprinting defects for reproduction and assisted reproductive technology. Hum Reprod Update 10, 3-18.
148. Fraga, M. F., Ballestar, E., Paz, M. F., Ropero, S., Setien, F., Ballestar, M. L., Heine-Suner, D., Cigudosa, J. C., Urioste, M., Benitez, J., et al. (2005). Epigenetic differences arise during the lifetime of monozygotic twins. Proc Natl Acad Sci USA 102, 10604-10609.
149. McLean, D. J., Friel, P. J., Pouchnik, D., and Griswold, M. D. (2002). Oligonucleotide microarray analysis of gene expression in follicle-stimulating hormone-treated rat Sertoli cells. Mol Endocrinol 16, 2780-2792.
150. Shima, J. E., McLean, D. J., McCarrey, J. R., and Griswold, M. D. (2004). The murine testicular transcriptome: characterizing gene expression in the testis during the progress of spermatogenesis. Biol Reprod 71, 319-330.
151. Bartolomei, M. S., Zemel, S., and Tilghman, S. M. (1991). Parental imprinting of the mouse H19 gene. Nature 351, 153-155.
152. Anway, M. D., Leathers, C., and Skinner, M. K. (2006). Endocrine Disruptor Vinclozolin Induced Epigenetic Transgenerational Adult Onset Diseases. Endocrinology (Submitted).
153. Deak, K. L., Boyles, A. L., Etchevers, H. C., Melvin, E. C., Siegel, D. G., Graham, F. L., Slifer, S. H., Enterline, D.

S., George, T. M., Vekemans, M., et al. (2005). SNPs in the neural cell adhesion molecule 1 gene (NCAM1) may be associated with human neural tube defects. Hum Genet 117, 133-142.
154. Femebro, J., Francis, P., Eden, P., Borg, A., Panagopoulos, I., Mertens, F., Vallon-Christersson, J., Akerman, M., Rydholm, A., Bauer, H. C., et al. (2005). Gene expression profiles relate to SS18/SSX fusion type in synovial sarcoma. Int J Cancer.
155. Hakansson, J., Xian, X., He, L., Stahlberg, A., Nelander, S., Samuelsson, T., Kubista, M., and Semb, H. (2005). Neural cell adhesion molecule-deficient beta-cell tumorigenesis results in diminished extracellular matrix molecule expression and tumour cell-matrix adhesion. Tumour Biol 26, 103-112.
156. Kanemura, Y., Takuma, Y., Kamiguchi, H., and Yamasaki, M. (2005). First case of LICAM gene mutation identified in MASA syndrome in Asia. Congenit Anom (Kyoto) 45, 67-69.
157. Plappert, C. F., Schachner, M., and Pilz, P. K. (2005). Neural cell adhesion molecule-null mice are not deficient in prepulse inhibition of the startle response. Neuroreport 16, 1009-1012.
158. Todaro, L., Puricelli, L., Gioseffi, H., Guadalupe Pallotta, M., Lastiri, J., Bal de Kier Joffe, E., Varela, M., and Sacerdote de Lustig, E. (2004). Neural cell adhesion molecule in human serum. Increased levels in dementia of the Alzheimer type. Neurobiol Dis 15, 387-393.
159. Eilers, H., Trilk, S. L., Lee, S. Y., Xue, Q., Jong, B. E., Moff, I., Levine, J. D., and Schumacher, M. A. (2004). Isolation of an mRNA binding protein homologue that is expressed in nociceptors. Eur J Neurosci 20, 2283-2293.
160. Kawamura, S., Ikeda, Y., Tomita, K., Watanabe, N., and Seki, K. (2004). A family of hypokalemic periodic paralysis with CACNA1 S gene mutation showing incomplete penetrance in women. Intern Med 43, 218-222.
161. Lu, Z. J., Pereverzev, A., Liu, H. L., Weiergraber, M., Henry, M., Krieger, A., Smyth, N., Hescheler, J., and Schneider, T. (2004). Arrhythmia in isolated prenatal hearts after ablation of the Cav2.3 (alpha1E) subunit of voltage-gated Ca2+ channels. Cell Physiol Biochem 14, 11-22.
162. Pereverzev, A., Mikhna, M., Vajna, R., Gissel, C., Henry, M., Weiergraber, M., Hescheler, J., Smyth, N., and Schneider, T. (2002). Disturbances in glucose-tolerance, insulin-release, and stress-induced hyperglycemia upon disruption of the Ca(v)2.3 (alpha 1E) subunit of voltage-gated Ca(2+) channels. Mol Endocrinol 16, 884-895.
163. Sakata, Y., Saegusa, H., Zong, S., Osanai, M., Murakoshi, T., Shimizu, Y., Noda, T., Aso, T., and Tanabe, T. (2002). Ca(v)2.3 (alpha1E) Ca2+ channel participates in the control of sperm function. FEBS Lett 516, 229-233.
164. Nekrep, N., Geyer, M., Jabrane-Ferrat, N., and Peterlin, B. M. (2001). Analysis of ankyrin repeats reveals how a single point mutation in RFXANK results in bare lymphocyte syndrome. Mol Cell Biol 21, 5566-5576. Nicolopoulou-Stamati, P., and Pitsos, M. A. (2001).
165. Chao, W., Shen, Y., Li, L., Zhao, H., Meiler, S. E., Cook, S. A., and Rosenzweig, A. (2005). Fas-associated death-domain protein inhibits TNF-alpha mediated NF-kappaB activation in cardiomyocytes. Am J Physiol Heart Circ Physiol 289, H2073-2080.
166. Wu, Y. P., Mizukami, H., Matsuda, J., Saito, Y., Proia, R. L., and Suzuki, K. (2005). Apoptosis accompanied by up-regulation of TNF-alpha death pathway genes in the brain of Niemann-Pick type C disease. Mol Genet Metab 84, 9-17.
167. Shu, T., Butz, K. G., Plachez, C., Gronostajski, R. M., and Richards, L. J. (2003). Abnormal development of forebrain midline glia and commissural projections in Nfia knock-out mice. J Neurosci 23, 203-212.
168. Gong, G., Kosoko-Lasaki, O., Haynatzki, G. R., and Wilson, M. R. (2004). Genetic dissection of myocilin glaucoma. Hum Mol Genet 13 Spec No 1, R91-102.
169. Sarfarazi, M., and Rezaie, T. (2003). Optineurin in primary open angle glaucoma. Ophthalmol Clin North Am 16, 529-541.
170. Confaloni, A., Terreni, L., Piscopo, P., Crestini, A., Campeggi, L. M., Frigerio, C. S., Blotta, I., Perri, M., Di Natale, M., Maletta, R., et al. (2003). Nicastrin gene in familial and sporadic Alzheimer's disease. Neurosci Lett 353, 61-65.
171. De Strooper, B. (2005). Nicastrin: gatekeeper of the gamma-secretase complex. Cell 122, 318-320.
172. Li, T., Ma, G., Cai, H., Price, D. L., and Wong, P. C. (2003). Nicastrin is required for assembly of presenilin/gamma-secretase complexes to mediate Notch signaling and for processing and trafficking of beta-amyloid precursor protein in mammals. J Neurosci 23, 3272-3277.
173. Vissing, J., Quistorff, B., and Haller, R. G. (2005). Effect of fuels on exercise capacity in muscle phosphoglycerate mutase deficiency. Arch Neurol 62, 1440-1443.
174. Hof, D., Raats, J. M., and Pruijn, G. J. (2005). Apoptotic modifications affect the autoreactivity of the U1 snRNP autoantigen. Autoimmun Rev 4, 380-388.
175. Hoffman, R. W., Gazitt, T., Foecking, M. F., Ortmann, R. A., Misfeldt, M., Jorgenson, R., Young, S. L., and Greidinger, E. L. (2004). U1 RNA induces innate immunity signaling. Arthritis Rheum 50, 2891-2896.
176. Langley-Evans, S. C. (2006). Developmental programming of health and disease. Proc Nutr Soc 65, 97-105.
177. Valkova, N., Yunis, R., Mak, S. K., Kang, K., and Kultz, D. (2005). Nek8 mutation causes overexpression of galectin-1, sorcin, and vimentin and accumulation of the major urinary protein in renal cysts of jck mice. Mol Cell Proteomics 4, 1009-1018.
178. Liu, S., Shen, T., Huynh, L., Klisovic, M. I., Rush, L. J., Ford, J. L., Yu, J., Becknell, B., Li, Y., Liu, C., et al. (2005). Interplay of RUNX1/MTG8 and DNA methyltransferase 1 in acute myeloid leukemia. Cancer Res 65, 1277-1284.
179. Fiorentino, F., Nuccitelli, A., and Biricik, A. (2005). Gene symbol: WAS. Disease: Wiskott-Aldrich syndrome. Hum Genet 116, 539.
180. Dubourg, C., Lazaro, L., Pasquier, L., Bendavid, C., Blayau, M., Le Duff, F., Durou, M. R., Odent, S., and David, V. (2004). Molecular screening of SHH, ZIC2, SIX3, and TGIF genes in patients with features of holoprosencephaly spectrum: Mutation review and genotype-phenotype correlations. Hum Mutat 24, 43-51.
181. Laflamme, C., Filion, C., Bridge, J. A., Ladanyi, M., Goldring, M. B., and Labelle, Y. (2003). The homeotic protein Six3 is a coactivator of the nuclear receptor NOR-1 and a corepressor of the fusion protein EWS/NOR-1 in human extraskeletal myxoid chondrosarcomas. Cancer Res 63, 449-454.
182. Lazaro, L., Dubourg, C., Pasquier, L., Le Duff, F., Blayau, M., Durou, M. R., de la Pintiere, A. T., Aguilella, C., David, V., and Odent, S. (2004). Phenotypic and molecular variability of the holoprosencephalic spectrum. Am J Med Genet A 129, 21-24.
183. Nanni, L., Croen, L. A., Lammer, E. J., and Muenke, M. (2000). Holoprosencephaly: molecular study of a California population. Am J Med Genet 90, 315-319.

184. Dong, H., Bonala, R. R., Suzuki, N., Johnson, F., Grollman, A. P., and Shibutani, S. (2004). Mutagenic potential of benzo[a]pyrene-derived DNA adducts positioned in codon 273 of the human P53 gene. Biochemistry 43, 15922-15928.
185. Li, J. Y., Lees-Murdock, D. J., Xu, G. L., and Walsh, C. P. (2004). Timing of establishment of paternal methylation imprints in the mouse. Genomics 84, 952-960.
186. Yamazaki, Y., Mann, M. R., Lee, S. S., Marh, J., McCarrey, J. R., Yanagimachi, R., and Bartolomei, M. S. (2003). Reprogramming of primordial germ cells begins before migration into the genital ridge, making these cells inadequate donors for reproductive cloning. Proc Natl Acad Sci USA 100, 12207-12212.
187. Pfeifer, K. (2000). Mechanisms of genomic imprinting. Am J Hum Genet 67, 777-787.
188. Monk, M., and Salpekar, A. (2001). Expression of imprinted genes in human preimplantation development. Mol Cell Endocrinol 183 Suppl 1, S35-40.
189. Scarano, M. I., Strazzullo, M., Matarazzo, M. R., and D'Esposito, M. (2005). DNA methylation 40 years later: Its role in human health and disease. J Cell Physiol 204, 21-35.
190. Wang, J., Kataoka, H., Suzuki, M., Sato, N., Nakamura, R., Tao, H., Maruyama, K., Isogaki, J., Kanaoka, S., Ihara, M., et al. (2005). Downregulation of EphA7 by hypermethylation in colorectal cancer. Oncogene 24, 5637-5647.
191. Li, E. (2002). Chromatin modification and epigenetic reprogramming in mammalian development. Nat Rev Genet 3, 662-673.
192. Allegrucci, C., Thurston, A., Lucas, E., and Young, L. (2005). Epigenetics and the germline. Reproduction 129, 137-149.
193. Morgan, H. D., Santos, F., Green, K., Dean, W., and Reik, W. (2005). Epigenetic reprogramming in mammals. Hum Mol Genet 14 Spec No 1, R47-58.
194. Morison, I. M., Ramsay, J. P., and Spencer, H. G. (2005). A census of mammalian imprinting. Trends Genet 21, 457-465.
195. Schumacher, A., Kapranov, P., Kaminsky, Z., Flanagan, J., Assadzadeh, A., Yau, P., Virtanen, C., Winegarden, N., Cheng, J., Gingeras, T., and Petronis, A. (2006). Microarray-based DNA methylation profiling: technology and applications. Nucleic Acids Res 34, 528-542.
196. Zhang, Y. W., Luo, W. J., Wang, H., Lin, P., Vetrivel, K. S., Liao, F., Li, F., Wong, P. C., Farquhar, M. G., Thinakaran, G., and Xu, H. (2005). Nicastrin is critical for stability and trafficking but not association of other presenilin/gamma-secretase components. J Biol Chem 280, 17020-17026.
197. Kimberly, W. T., and Wolfe, M. S. (2003). Identity and function of gamma-secretase. J Neurosci Res 74, 353-360.
198. Bertram, L., Busch, R., Spiegl, M., Lautenschlager, N. T., Muller, U., and Kurz, A. (1998). Paternal age is a risk factor for Alzheimer disease in the absence of a major gene. Neurogenetics 1, 277-280.

What is claimed is:

1. A method of detecting an epigenetic, transgenerational alteration, in the germ-line DNA of a male progeny subject from a female parental subject exposed to or administered at least one endocrine disruptor, comprising identifying methylated DNA in the germ line of the male progeny subsequent to the F1 generation subject, wherein the subsequent male progeny is not directly exposed to the endocrine disruptor and wherein the methylated DNA so identified is associated with epigenetic changes resulting from toxicant exposure of the female parental subject to the endocrine disruptor.

2. The method of claim 1, wherein said method comprises use of a microarray assay.

3. The method of claim 1, which said method comprises use of a methylation sensitive restriction enzyme digest analyis followed by PCR to identify alterations in DNA methylation.

4. The method of claim 1, wherein the male progeny not exposed to the endocrine disruptor is in the F3 generation or later generation.

5. The method of claim 4, wherein the later generation is an F4 generation.

6. The method of claim 1, wherein said epigenetic, transgenerational alteration is methylation of DNA in the germline DNA of the male progeny and is associated with a disease and/or dysfunction.

* * * * *